(12) United States Patent
Andres et al.

(10) Patent No.: US 9,643,956 B2
(45) Date of Patent: May 9, 2017

(54) SOLID FORMS OF AN ASK1 INHIBITOR

(71) Applicant: Gilead Sciences, Inc., Foster City, CA (US)

(72) Inventors: Mark Andres, West Lafayette, IN (US); Brenda J. Burke Chan, Foster City, CA (US); Ernest A. Carra, Foster City, CA (US); Anna Chiu, Burlingame, CA (US); Olga Viktorovna Lapina, Newark, CA (US); Stephen P. Lathrop, San Mateo, CA (US); Gregory Notte, Redwood City, CA (US); Valeriya Smolenskaya, West Lafayette, IN (US); Lok Him Yu, Sacramento, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/757,585

(22) Filed: Dec. 22, 2015

(65) Prior Publication Data
US 2016/0280683 A1 Sep. 29, 2016

Related U.S. Application Data

(60) Provisional application No. 62/269,066, filed on Dec. 17, 2015, provisional application No. 62/096,406, filed on Dec. 23, 2014.

(51) Int. Cl.
| | |
|---|---|
| *C07D 249/08* | (2006.01) |
| *C07D 401/14* | (2006.01) |
| *C07D 413/12* | (2006.01) |
| *A61K 31/422* | (2006.01) |
| *A61K 31/4439* | (2006.01) |
| *A61K 31/541* | (2006.01) |
| *C07C 55/07* | (2006.01) |
| *C07C 57/145* | (2006.01) |
| *C07C 57/15* | (2006.01) |
| *C07C 59/06* | (2006.01) |
| *C07C 309/04* | (2006.01) |

(52) U.S. Cl.
CPC .......... *C07D 401/14* (2013.01); *A61K 31/422* (2013.01); *A61K 31/4439* (2013.01); *A61K 31/541* (2013.01); *C07C 55/07* (2013.01); *C07C 57/145* (2013.01); *C07C 57/15* (2013.01); *C07C 59/06* (2013.01); *C07C 309/04* (2013.01); *C07D 413/12* (2013.01)

(58) Field of Classification Search
CPC .................................................... C07D 249/08
USPC ............ 548/262.2; 546/256, 272.4, 167, 113
See application file for complete search history.

(56) References Cited

U.S. PATENT DOCUMENTS 8,742,126 B2 * 6/2014 Notte .................... C07D 213/56
546/340

FOREIGN PATENT DOCUMENTS

| EP | 2545964 | 1/2013 |
| WO | WO 2013/112741 | 8/2013 |

OTHER PUBLICATIONS

Caira, "Crystalline Polymorphism of Organic Compounds," Topics in Current Chemistry, Springer, Berlin, DE, vol. 198, Jan. 1, 1998, pp. 168-208.
International Search Report and Written Opinion for PCT/US2015/000162, mailed Feb. 25, 2016 (12 pages).

* cited by examiner

*Primary Examiner* — Niloofar Rahmani
(74) *Attorney, Agent, or Firm* — Briana R. Barron

(57) ABSTRACT

Crystalline forms of 5-(4-cyclopropyl-1H-imidazol-1-yl)-N-(6-(4-isopropyl-4H-1,2,4-triazol-3-yl)pyridin-2-yl)-2-fluoro-4-methylbenzamide(Compound I) were prepared and characterized in the solid state:

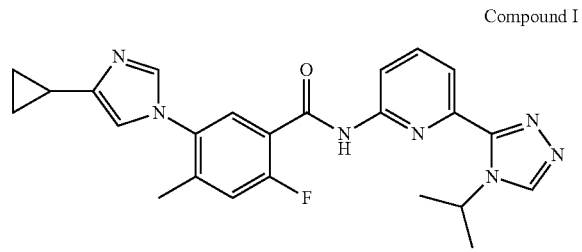

Compound I

Also provided are processes of manufacture and methods of using the crystalline forms.

81 Claims, 85 Drawing Sheets

SOLID FORMS OF AN ASK1 INHIBITOR

CROSS-REFERENCE TO RELATED APPLICATIONS

This application claims the benefit under of 35 U.S.C. §119(e) of U.S. Provisional Application 62/096,406, filed on Dec. 23, 2014, and U.S. Provisional Application 62/269,066, filed on Dec. 17, 2015, both of which are hereby incorporated by reference.

SEQUENCE LISTING

The instant application contains a Sequence Listing which has been submitted electronically in ASCII format and is hereby incorporated by reference in its entirety. Said ASCII copy, created on May 17, 2016, is named 37JD-198221-US_SL.txt and is 2,702 bytes in size.

FIELD

The present disclosure relates generally to crystalline forms of the compound 5-(4-cyclopropyl-1H-imidazol-1-yl)-N-(6-(4-isopropyl-4H-1,2,4-triazol-3-yl)pyridin-2-yl)-2-fluoro-4-methylbenzamide, designated herein as Compound I, pharmaceutical compositions thereof, their therapeutic use, and processes for making the forms.

BACKGROUND

Therapeutic agents that function as inhibitors of ASK1 signaling have the potential to remedy or improve the lives of patients in need of treatment for diseases or conditions such as neurodegenerative, cardiovascular, inflammatory, autoimmune, and metabolic disorders. In particular, ASK1 inhibitors have the potential to treat cardio-renal diseases, including kidney disease, diabetic kidney disease, chronic kidney disease, fibrotic diseases (including lung and kidney fibrosis), respiratory diseases (including chronic obstructive pulmonary disease (COPD) and acute lung injury), acute and chronic liver diseases. There is a need for high purity single polymorph forms of compounds that are efficacious and exhibit improved pharmacokinetic and/or pharmacodynamic profiles for the treatment of diseases related to ASK1 activation.

SUMMARY

Compound I is known to exhibit ASK1 inhibitory activity and is described in, for example, U.S. Pat. No. 8,742,126, which is hereby incorporated by reference in its entirety. Compound I has the Formula:

Compound I

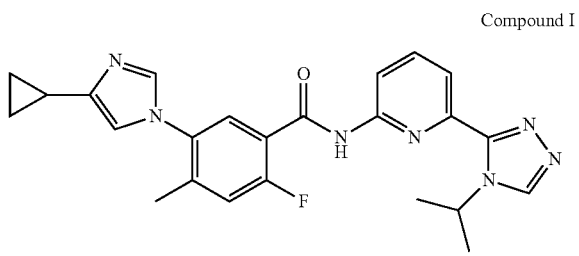 [SMILES: Cc1cc(F)c(C(=O)Nc2cccc(-c3nncn3C(C)C)n2)cc1-n1cnc(C2CC2)c1]

Compound I can be synthesized according to the methods described in U.S. Pat. No. 8,742,126 or U.S. Provisional Application Nos. 62/096,391, 62/269,064 and PCT Application PCT/US2015/067511 (filed on even date herewith and titled "Processes for Preparing ASK1 Inhibitors"), all of which are incorporated by reference in their entirety.

The present disclosure provides forms of Compound I and salts, co-crystals, hydrates, and solvates thereof. Also described herein are processes for making the forms of Compound I, pharmaceutical compositions comprising crystalline forms of Compound I and methods for using such forms and pharmaceutical compositions in the treatment of diseases mediated by ASK1 disregulation.

Thus, one embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form I) characterized by an X-ray powder diffractogram comprising the following peaks: 16.7, 21.3, and 22.8° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form II) characterized by an X-ray powder diffractogram comprising the following peaks: 11.2, 16.6, and 17.4° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form III) characterized by an X-ray powder diffractogram comprising the following peaks: 5.1, 10.2, and 25.3° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form IV) characterized by an X-ray powder diffractogram comprising the following peaks: 7.2, 12.6, and 19.3° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form V) characterized by an X-ray powder diffractogram comprising the following peaks: 9.7, 13.3, and 16.4° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form VI) characterized by an X-ray powder diffractogram comprising the following peaks: 8.8, 23.2, and 23.5° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form VII) characterized by an X-ray powder diffractogram comprising the following peaks: 8.2, 14.2, and 22.9° 2θ±0.2° 2θ as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form VIII) characterized by an X-ray powder diffractogram comprising the following peaks: 8.4, 19.3, and 24.3° 2θ±0.2° 2θ as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form IX) characterized by an X-ray powder diffractogram comprising the following peaks: 6.9, 14.3, 23.7, and 24.8° 2θ±0.2° 2θ as determined on a diffractometer using Cu-Kα radiation at a wavelength of 1.5406 Å.

Another embodiment is amorphous 5-(4-cyclopropyl-1H-imidazol-1-yl)-N-(6-(4-isopropyl-4H-1,2,4-triazol-3-yl)pyridin-2-yl)-2-fluoro-4-methylbenzamide.

Some embodiments provided herein relate to crystalline forms of salts or co-crystals of Compound I.

Thus, one embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide esylate (Compound I Esylate Form I) characterized by an X-ray powder diffractogram comprising the following peaks: 8.9, 23.6, and 25.9° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide fumarate (Compound I Fumarate Form I) characterized by an X-ray powder diffractogram comprising the following peaks: 18.9, 23.2, and 25.6° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide glycolate (Compound I Glycolate Form I) characterized by an X-ray powder diffractogram comprising the following peaks: 10.9, 15.1, and 25.2° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide hydrochloride (Compound I HCl Form I) characterized by an X-ray powder diffractogram comprising the following peaks: 8.2, 26.0, and 26.1° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide maleate (Compound I Maleate Form I) characterized by an X-ray powder diffractogram comprising the following peaks: 8.7, 25.7, and 26.5° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide mesylate (Compound I Mesylate Form I) characterized by an X-ray powder diffractogram comprising the following peaks: 8.9, 24.5, and 25.6° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide oxalate (Compound I Oxalate Form I) characterized by an X-ray powder diffractogram comprising the following peaks: 13.3, 13.5, and 26.0° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide sulfate (Compound I Sulfate Form I) characterized by an X-ray powder diffractogram comprising the following peaks: 7.1, 13.8, and 25.5° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide adipate (Compound I Adipate Form I) characterized by an X-ray powder diffractogram comprising the following peaks: 6.4, 14.6, and 24.5° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide besylate (Compound I Besylate Form I) characterized by an X-ray powder diffractogram comprising the following peaks: 6.9, 10.8, and 12.9° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide edisylate (Compound I Edisylate Form I) characterized by an X-ray powder diffractogram comprising the following peaks: 10.3, 16.9, 19.5, and 23.7° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide edisylate (Compound I Edisylate Form II) characterized by an X-ray powder diffractogram comprising the following peaks: 14.7, 20.6, and 22.7° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide gentisate (Compound I Gentisate Form I) characterized by an X-ray powder diffractogram comprising the following peaks: 9.7, 12.5, and 26.2° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide gentisate (Compound I Gentisate Form II) characterized by an X-ray powder diffractogram comprising the following peaks: 5.2, 10.7, and 12.1° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide glutarate (Compound I Glutarate Form I) characterized by an X-ray powder diffractogram comprising the following peaks: 7.5, 20.8, and 23.3° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide glutarate (Compound I Glutarate Form II) characterized by an X-ray powder diffractogram comprising the following peaks: 5.1, 13.1, and 16.4° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide L-tartrate (Compound I L-Tartrate Form I) characterized by an X-ray powder diffractogram comprising the following peaks: 4.3, 12.4, and 24.8° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl)

pyridin-2-yl)-2-fluoro-4-methylbenzamide L-tartrate (Compound I L-Tartrate Form II) characterized by an X-ray powder diffractogram comprising the following peaks: 4.7, 9.9, 11.4 and 22.0° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl) pyridin-2-yl)-2-fluoro-4-methylbenzamide propyl gallate (Compound I Propyl Gallate Form I) characterized by an X-ray powder diffractogram comprising the following peaks: 3.8, 7.6, and 24.9° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl) pyridin-2-yl)-2-fluoro-4-methylbenzamide succinate (Compound I Succinate Form I) characterized by an X-ray powder diffractogram comprising the following peaks: 12.7, 21.2, and 24.7° 2θ±0.2° 2θ, as determined on a diffractometer using Cu-Kα radiation at a wavelength of 1.5406 Å.

Another embodiment is crystalline 5-(4-cyclopropyl-1H-imidazol-1-yl)-N-(6-(4-isopropyl-4H-1,2,4-triazol-3-yl) pyridin-2-yl)-2-fluoro-4-methylbenzamide tosylate (Compound I Tosylate Form I) characterized by an X-ray powder diffractogram comprising the following peaks: 6.6, 12.1, and 12.8° 2θ±0.2° 2θ, as determined on a diffractometer using Cu-Kα radiation at a wavelength of 1.5406 Å.

Another embodiment is directed to pharmaceutical compositions comprising a form or forms of Compound I as described herein and one or more pharmaceutically acceptable carriers.

Another embodiment is directed to the use of a form of Compound I as described herein or a pharmaceutical composition as described herein in the treatment of a disease in a patient in need of treatment with an ASK1 inhibitor.

Another embodiment is directed to a method of treating a disease mediated, at least in part, by ASK1 in a patient in need thereof comprising administering a therapeutically effective amount of a form of Compound I as described herein or a pharmaceutical composition as described herein. In some embodiments, the disease is diabetes, diabetic nephropathy, kidney disease, kidney fibrosis, lung fibrosis, idiopathic pulmonary fibrosis (IPF), liver fibrosis, pulmonary hypertension, nonalcoholic steatohepatitis, liver disease, alcoholic liver disease, alcoholic hepatitis, an inflammatory condition, an autoimmune disease, a proliferative disease, a transplantation rejection, a disease involving impairment of cartilage turnover, a congenital cartilage malformation, or a disease associated with hypersecretion of IL6.

Another embodiment is directed to the method of treating diabetic nephropathy, or complications of diabetes, comprising administering a therapeutically effective amount of a form of Compound I as described herein or a pharmaceutical composition as described herein.

Another embodiment is directed to the method of treating kidney disease, or diabetic kidney disease comprising administering a therapeutically effective amount of a form of Compound I as described herein or a pharmaceutical composition as described herein.

Another embodiment is directed to the method of treating kidney fibrosis, lung fibrosis, or idiopathic pulmonary fibrosis (IPF) comprising administering a therapeutically effective amount of a form of Compound I as described herein or a pharmaceutical composition as described herein.

Another embodiment is directed to the method of treating diabetic kidney disease, diabetic nephropathy, kidney fibrosis, liver fibrosis, or lung fibrosis comprising administering a therapeutically effective amount of a crystalline form of Compound I as described herein or a pharmaceutical composition as described herein.

Another embodiment is directed to a method of treating pulmonary hypertension in a patient in need thereof, said method comprising administering to the patient a therapeutically effective amount of a form of Compound I as described herein or a pharmaceutical composition as described herein. The pulmonary hypertension, in one aspect, is pulmonary arterial hypertension (PAH) which may be selected from idiopathic PAH, familial PAH, pulmonary veno-occlusive disease (PVOD), pulmonary capillary hemangiomatosis (PCH), persistent pulmonary hypertension of the newborn, or PAH associated with another disease or condition. In some embodiments, the pulmonary hypertension is pulmonary arterial hypertension.

Another embodiment is directed to the method of treating nonalcoholic steatohepatitis (NASH) comprising administering a therapeutically effective amount of a form of Compound I as described herein or a pharmaceutical composition as described herein. Another embodiment is directed to the method of treating liver fibrosis comprising administering a therapeutically effective amount of a form of Compound I as described herein or a pharmaceutical composition as described herein.

Another embodiment is directed to the method of treating liver disease comprising administering a therapeutically effective amount of a form of Compound I as described herein or a pharmaceutical composition as described herein.

Another embodiment is directed to the method of treating alcoholic liver disease comprising administering a therapeutically effective amount of a form of Compound I as described herein or a pharmaceutical composition as described herein.

Another embodiment is directed to the method of treating alcoholic hepatitis comprising administering a therapeutically effective amount of a form of Compound I as described herein or a pharmaceutical composition as described herein.

Another embodiment is directed to the method of preventing and/or treating inflammatory conditions, autoimmune diseases, proliferative diseases, transplantation rejection, diseases involving impairment of cartilage turnover, congenital cartilage malformations, and diseases associated with hypersecretion of IL6 in mammals including humans comprising administering a therapeutically effective amount of a form of Compound I as described herein in combination with a therapeutically effective amount of filgotinib. In one embodiment, the inflammatory condition is rheumatoid arthritis. In one embodiment, the inflammatory condition is Crohn's disease.

Another embodiment is directed to the method of treating preventing and/or treating inflammatory conditions, autoimmune diseases, proliferative diseases, transplantation rejection, diseases involving impairment of cartilage turnover, congenital cartilage malformations, and diseases associated with hypersecretion of IL6 in mammals including humans comprising administering therapeutically effective amount of a pharmaceutical composition comprising a form of Compound I as described herein and filgotinib. In one embodiment, the inflammatory condition is rheumatoid arthritis. In one embodiment, the inflammatory condition is Crohn's disease. In one embodiment, the disease is inflammatory bowel disease.

Another embodiment is directed to the use of a form of Compound I as described herein or a pharmaceutical composition as described herein in the treatment of a disease mediated, at least in part, by ASK1 in a patient in need thereof.

Another embodiment is directed to the use of a form of Compound I as described herein or a pharmaceutical composition as described herein in the treatment of a chronic kidney disease.

Another embodiment is directed to the use of a form of Compound I as described herein or a pharmaceutical composition as described herein in the treatment of a diabetic kidney disease.

Another embodiment is directed to the use of a form of Compound I as described herein or a pharmaceutical composition as described herein in the manufacture of a medicament for the treatment of a chronic kidney disease.

Another embodiment is directed to the use of a form of Compound I as described herein or a pharmaceutical composition as described herein in the manufacture of a medicament for the treatment of a diabetic kidney disease.

Another embodiment is directed to the use of a form of Compound I as described herein or a pharmaceutical composition as described herein in the manufacture of a medicament for the treatment of pulmonary hypertension.

Another embodiment is directed to the use of a form of Compound I as described herein or a pharmaceutical composition as described herein in the manufacture of a medicament for the treatment of liver disease.

Another embodiment is directed to the use of a form of Compound I as described herein or a pharmaceutical composition as described herein in the manufacture of a medicament for the treatment of alcoholic liver disease.

Another embodiment is directed to the use of a form of Compound I as described herein or a pharmaceutical composition as described herein in the manufacture of a medicament for the treatment of alcoholic hepatitis.

Another embodiment is directed to the use of a form of Compound I as described herein in combination with filgotinib in the manufacture of a medicament for the prevention or treatment of inflammatory conditions, autoimmune diseases, proliferative diseases, transplantation rejection, diseases involving impairment of cartilage turnover, congenital cartilage malformations, and diseases associated with hypersecretion of IL6 in mammals including humans.

Another embodiment is directed to the use of a pharmaceutical composition comprising a form of Compound I as described herein in combination with filgotinib in the manufacture of a medicament for the prevention or treatment of inflammatory conditions, autoimmune diseases, proliferative diseases, transplantation rejection, diseases involving impairment of cartilage turnover, congenital cartilage malformations, and diseases associated with hypersecretion of IL6 in mammals including humans.

DETAILED DESCRIPTION

Figure 1:
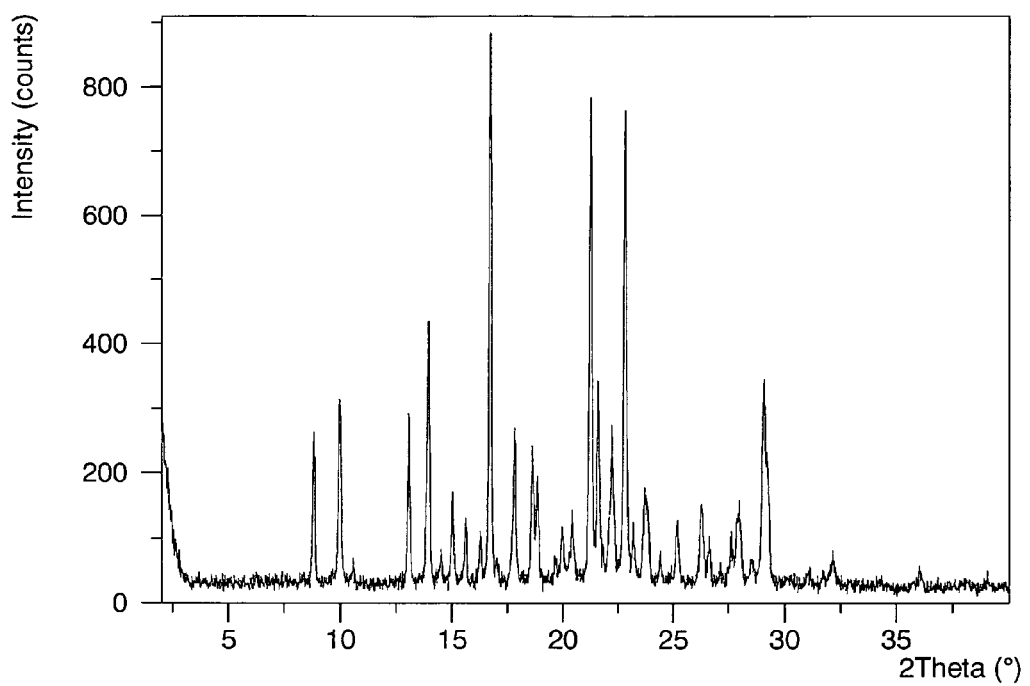
FIG. 1 shows an X-ray powder diffraction (XRPD) of Compound I Form I.

The compound, 5-(4-cyclopropyl-1H-imidazol-1-yl)-N-(6-(4-isopropyl-4H-1,2,4-triazol-3-yl)pyridin-2-yl)-2-fluoro-4-methylbenzamide (also known as 5-((4-cyclopropyl-1H-imidazol-1-yl)-2-fluoro-N-(6-(4-isopropyl-4H-1,2,4-triazole-3-yl)pyridine-2-yl)-4-methylbenzamide)) designated herein as Compound I, has the formula:

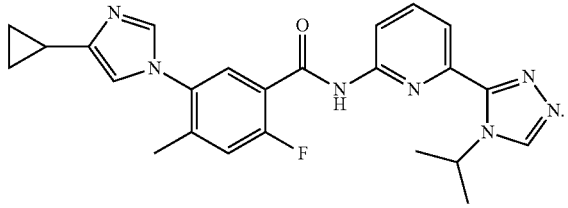 [SMILES: Cc1cc(F)c(C(=O)Nc2cccc(-c3nncn3C(C)C)n2)cc1-n1cnc(C2CC2)c1]

Compound I exhibits an $EC_{50}$ value of about 2 nanomolar in an ASK1 293 cell-based assay. The experimental protocol for this assay is known in the art and is described in U.S. Pat. No. 8,742,126, which is hereby incorporated by reference in its entirety.

The present disclosure relates to various crystalline forms of Compound I, and processes for making the crystalline forms. Compound I also provides forms further described herein as "Compound I Form I," "Compound I Form II," "Compound I Form III," "Compound I Form IV," "Compound I Form V," "Compound I Form VI," "Compound I Form VII," "Compound I Form VIII," "Compound I Form IX," and "amorphous Compound I." In some embodiments, such forms of Compound I may be a solvate or a hydrate.

Additional crystalline forms of Compound I are also further described herein. In some embodiments, crystalline forms of Compound I may include salts or co-crystals of Compound I. Salts or co-crystals of Compound I may have the following formula:

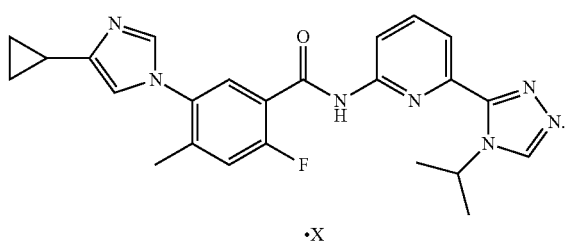 [SMILES: Cc1cc(F)c(C(=O)Nc2cccc(-c3nncn3C(C)C)n2)cc1-n1cnc(C2CC2)c1 ; "·X"]

·X

In some embodiments, X may be esylate, fumarate, glycolate, hydrochloride, maleate, mesylate, oxalate, sulfate, adipate, besylate, edisylate, gentisate, glutarate, L-tartrate, propyl gallate, succinate, and tosylate. The following exemplary forms are further described herein: "Compound I Esylate Form I," "Compound I Fumarate Form I," "Compound I Glycolate Form I," "Compound I HC1 Form I," "Compound I Maleate Form I," "Compound I Mesylate Form I," "Compound I Oxalate Form I," "Compound I Sulfate Form I," "Compound I Adipate Form I," "Compound I Besylate Form I," "Compound I Edisylate Form I," "Compound I Edisylate Form II," "Compound I Gentisate Form I," "Compound I Gentisate Form II," "Compound I Glutarate Form I," "Compound I Glutarate Form II," "Compound I L-tartrate Form I," "Compound I L-tartrate Form II," "Compound I Propyl Gallate Form I," "Compound I Succinate Form I," and "Compound I Tosylate Form I."

Definitions

As used in the present specification, the following words and phrases are generally intended to have the meanings as set forth below, except to the extent that the context in which they are used indicates otherwise.

As used herein, the term "about" used in the context of quantitative measurements means the indicated amount±10%, or alternatively the indicated amount±5% or ±1%.

The term "complex" refers to a formation resulting from the interaction between Compound I and another molecule.

The term "solvate" refers to a complex formed by combining Compound I and a solvent. As used herein, the term "solvate" includes a hydrate (i.e., a solvate when the solvent is water).

The term "co-crystal" refers to a molecular complex of an ionized or non-ionized Compound I (or any other compound disclosed herein) and one or more non-ionized co-crystal formers (such as a pharmaceutically acceptable salt) connected through non-covalent interactions. In certain embodiments, the co-crystal can have an improved property as compared to the free form (i.e., the free molecule, zwitter ion, hydrate, solvate, etc.) or a salt (which includes salt hydrates and solvates). In further embodiments, the improved property is selected from the group consisting of: increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like.

The term "co-crystal former" or "co-former" refers to one or more pharmaceutically acceptable bases and/or pharmaceutically acceptable acids disclosed herein in association with Compound I, or any other compound disclosed herein.

Any formula or structure given herein, including Compound I, is also intended to represent unlabeled forms as well as isotopically labeled forms of the compounds. Isotopically labeled compounds have structures depicted by the formulae given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which isotopes such as $^{3}H$, $^{13}C$ and $^{14}C$ are incorporated, may be prepared. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes Compound I in which from 1 to "n" hydrogens attached to a carbon atom is/are replaced by deuterium, in which n is the number of hydrogens in the molecule. Such compounds exhibit increased resistance to metabolism and may be thus useful for increasing the halflife of any Compound I when administered to a mammal. See, for example, Foster, "Deuterium Isotope Effects in Studies of Drug Metabolism", *Trends Pharmacol. Sci.* 5(12): 524-527 (1984). Such compounds are synthesized by means well known in the art, for example by employing starting materials in which one or more hydrogen atoms have been replaced by deuterium.

Deuterium labeled or substituted compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent in Compound I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

As used herein, "pharmaceutically acceptable carrier" includes excipients or agents such as solvents, diluents, dispersion media, coatings, antibacterial and antifungal agents, isotonic and absorption delaying agents and the like that are not deleterious to the compound of the invention or use thereof. The use of such carriers and agents to prepare compositions of pharmaceutically active substances is well known in the art (see, e.g., *Remington's Pharmaceutical Sciences*, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The term "therapeutically effective amount" refers to an amount of the compound as described herein that is sufficient to effect treatment as defined below, when administered to a patient (particularly a human) in need of such treatment in one or more doses. The therapeutically effective amount will vary, depending upon the patient, the disease being treated, the weight and/or age of the patient, the severity of the disease, or the manner of administration as determined by a qualified prescriber or care giver.

The term "treatment" or "treating" means administering a compound as described herein for the purpose of:
(i) delaying the onset of a disease, that is, causing the clinical symptoms of the disease not to develop or delaying the development thereof;
(ii) inhibiting the disease, that is, arresting the development of clinical symptoms; and/or
(iii) relieving the disease, that is, causing the regression of clinical symptoms or the severity thereof.

In addition, abbreviations as used herein have respective meanings as follows:

| | |
|---|---|
| % AN/% ES | % Area normalized versus % external standard |
| μL | Microliter |
| μm | Micrometer |
| 2-MeTHF | 2-methyl tetrahydrofuran |
| ACN | Acetonitrile |
| API | Active pharmaceutical ingredient |
| ASK 1 | Apoptosis signal-regulating kinase 1 |
| BE | Butyl ether |
| BN | Butyronitrile |
| DCM | Dichloromethane |
| DSC | Differential scanning calorimetry |
| DVS | Dynamic vapor sorption |
| eq. | Equivalents |
| EtOAc | Ethyl acetate |
| EtOH | Ethanol |
| g | Gram |
| h | Hour |
| IC | Ion chromatography |
| IPA | Isopropanol |
| IPE | Diisopropyl ether |
| IPAc/iPrOAc | Isopropyl acetate |
| KF | Karl Fischer titration |
| kV | kilovolts |
| MEK | Methyl ethyl ketone |
| MeOH | Methanol |
| MIBK | Methyl iso-butyl ketone |
| mA | Milliamps |
| mg | Milligram |
| min | Minute |
| mL/ml | Milliliter |
| MTBE | Methyl tert-butyl ether |
| NMR | Nuclear magnetic resonance |
| PLM | Polarized light microscopy |
| RH | Relative humidity |
| RT | Room temperature |
| s | Second |
| TGA | Thermogravimetric analysis |
| THF | Tetrahydrofuran |
| v/v | Volume to volume |
| wt | Weight |
| wt/wt | Weight to weight |
| XRPD | X-ray powder diffraction |

Forms of Compound I

As described generally above, the present disclosure provides crystalline forms of Compound I and Compound I salts/co-crystals, which are as designated herein. Additional forms are also discussed further herein.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form I) is characterized by an X-ray powder diffractogram comprising the following peaks: 16.7, 21.3, and 22.8° 2θ±0.2° 2θ, as determined on a diffractometer using Cu-Kα radiation at a wavelength of 1.5406 Å. The diffractogram comprises additional peaks at 8.9, 10.0, 13.9, and 29.0° 2θ±0.2° 2θ. Compound I Form I is also characterized by its full X-ray powder diffractogram as substantially shown in FIG. 1. In some embodiments, the diffractogram of Compound I Form I comprises the following peaks: 8.9, 10.0, 13.1, 13.9, 15.0, 16.7, 17.8, 18.6, 18.8, 21.3, 21.6, 22.2, 22.8, 23.7, and 29.0° 2θ±0.2° 2θ.

In some embodiments, Compound I Form I is characterized by a differential scanning calorimetry (DSC) curve that comprises an endotherm at about 202° C. Compound I Form I also is characterized by its full DSC curve as substantially shown in FIG. 2.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form II) is characterized by an X-ray powder diffractogram comprising the following peaks: 11.2, 16.6, and 17.4° 2θ±0.2° 2θ, as determined on a diffractometer using Cu-Kα radiation at a wavelength of 1.5406 Å. The diffractogram comprises additional peaks at 4.9, 23.7, and 27.4° 2θ±0.2° 2θ. Compound I Form II is also characterized by its full X-ray powder diffractogram as substantially shown in FIG. 4. In some embodiments, the diffractogram of Compound I Form II comprises the following peaks: 4.9, 10.0, 11.2, 11.7, 11.8, 12.6, 14.3, 15.6, 16.6, 17.4, 17.8, 18.3, 18.8, 22.5, 22.8, 23.7, 27.1, 27.4, 28.2, and 28.4° 2θ±0.2° 2θ.

In some embodiments, Compound I Form II is characterized by a differential scanning calorimetry (DSC) curve that comprises an endotherm at about 92° C., an endotherm at about 160° C., an exotherm at about 166° C., and endotherm at about 200° C. Compound I Form II also is characterized by its full DSC curve as substantially shown in FIG. 5.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form III) is characterized by an X-ray powder diffractogram comprising the following peaks: 5.1, 10.2, and 25.3° 2θ±0.2° 2θ, as determined on a diffractometer using Cu-Kα radiation at a wavelength of 1.5406 Å. The diffractogram comprises additional peaks at 11.4, 18.4, and 21.9° 2θ±0.2° 2θ. Compound I Form III is also characterized by its full X-ray powder diffractogram as substantially shown in FIG. 7. In some embodiments, the diffractogram of Compound I Form III comprises the following peaks: 5.1, 10.2, 11.4, 16.9, 18.4, 19.5, 21.1, 21.6, 21.9, 22.2, 23.9, 24.5, 25.3, 26.3, and 26.6° 2θ±0.2° 2θ.

In some embodiments, Compound I Form III is characterized by a differential scanning calorimetry (DSC) curve that comprises an endotherm at about 92° C., an exotherm at about 150° C., and an endotherm at about 203° C. Compound I Form III also is characterized by its full DSC curve as substantially shown in FIG. 8.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form IV) is characterized by an X-ray powder diffractogram comprising the following peaks: 7.2, 12.6, and 19.3° 2θ±0.2° 2θ, as determined on a diffractometer using Cu-Kα radiation at a wavelength of 1.5406 Å. The diffractogram comprises additional peaks at 13.8, 25.9, and 28.6° 2θ±0.2° 2θ. Compound I Form IV is also characterized by its full X-ray powder diffractogram as substantially shown in FIG. 10. In some embodiments, the diffractogram of Compound I Form IV comprises the following peaks: 7.2, 12.6, 13.8, 14.3, 14.8, 15.9, 17.7, 18.0, 18.4, 19.2, 19.3, 21.5, 23.4, 23.9, 25.2, 25.9, 27.3, and 28.6° 2θ±0.2° 2θ.

In some embodiments, Compound I Form IV is characterized by a differential scanning calorimetry (DSC) curve that comprises an endotherm at about 62° C., an endotherm at about 147° C., an exotherm at about 153° C., and endotherm at about 204° C. Compound I Form IV also is characterized by its full DSC curve as substantially shown in FIG. 11.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form V) is characterized by an X-ray powder diffractogram comprising the following peaks: 9.7, 13.3, and 16.4° 2θ±0.2° 2θ, as determined on a diffractometer using Cu-Kα radiation at a wavelength of 1.5406 Å. The diffractogram comprises additional peaks at 13.3, 17.2, 19.3, and 22.2° 2θ±0.2° 2θ. A mixture of Compound I Form V and Compound I Form II is also characterized by its full X-ray powder diffractogram as substantially shown in FIG. 13. In some embodiments, a diffractogram of Compound I Form V comprises the following peaks: 9.7, 12.4, 13.3, 16.4, 17.2, 19.3, 22.2, 24.9, and 27.9° 2θ±0.2° 2θ.

In some embodiments, a mixture of Compound I Form V and Compound I Form II is characterized by a differential scanning calorimetry (DSC) curve that comprises an endotherm at about 164° C. In another embodiment, a mixture of Compound I Form V and Compound I Form II is characterized by a differential scanning calorimetry (DSC) curve that further comprises an endotherm at about 91° C. A mixture of Compound I Form V and Compound I Form II also is characterized by its full DSC curve as substantially shown in FIG. 14.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form VI) is characterized by an X-ray powder diffractogram comprising the following peaks: 8.8, 23.2, and 23.5° 2θ±0.2° 2θ, as determined on a diffractometer using Cu-Kα radiation at a wavelength of 1.5406 Å. The diffractogram comprises additional peaks at 10.3, 15.2, 18.6, and 28.8° 2θ±0.2° 2θ. Compound I Form VI is also characterized by its full X-ray powder diffractogram as substantially shown in FIG. 16. In some embodiments, the diffractogram of Compound I Form VI comprises the following peaks: 8.8, 10.3, 10.9, 15.2, 16.1, 18.1, 18.3, 18.6, 23.2, 23.3, 23.5, 26.1, 28.5, and 28.8° 2θ±0.2° 2θ.

In some embodiments, Compound I Form VI is characterized by a differential scanning calorimetry (DSC) curve that comprises an endotherm at about 202° C. Compound I Form VI also is characterized by its DSC curve as substantially shown in FIG. 17.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form VII) is characterized by an X-ray powder diffractogram comprising the following peaks: 8.2, 14.2, and 22.9° 2θ±0.2° 2θ, as determined on a diffractometer using Cu-Kα radiation at a wavelength of 1.5406 Å. The diffractogram comprises additional peaks at 18.0 and 21.7° 2θ±0.2° 2θ. Compound I Form VII is also characterized by its full X-ray powder diffractogram as substantially shown in FIG. 41. In some embodiments, the diffractogram of Compound I Form VII comprises the following peaks: 8.2, 14.2, 18.0, 21.7, and 22.9° 2θ±0.2° 2θ.

In some embodiments, Compound I Form VII is characterized by a differential scanning calorimetry (DSC) curve that comprises an endotherm at about 202° C. In some embodiments, Compound I Form VII is characterized by a differential scanning calorimetry (DSC) curve that further comprises an endotherm at about 147° C. Compound I Form VII also is characterized by its full DSC curve as substantially shown in FIG. 42.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form VIII is characterized by an X-ray powder diffractogram comprising the following peaks: 8.4, 19.3, and 24.3° 2θ±0.2° 2θ, as determined on a diffractometer using Cu-Kα radiation at a wavelength of 1.5406 Å. The diffractogram comprises additional peaks at 14.6, 15.0, 16.8, and 20.4° 2θ±0.2° 2θ. Compound I Form VIII is also characterized by its full X-ray powder diffractogram as substantially shown in FIG. 44. In some embodiments, the diffractogram of Compound I Form VIII comprises the following peaks: 8.4, 14.6, 15.0, 16.8, 19.3, 20.4, and 24.3° 2θ±0.2° 2θ.

In some embodiments, Compound I Form VIII is characterized by a differential scanning calorimetry (DSC) curve that comprises an endotherm at about 203° C. In some embodiments, Compound I Form VIII is characterized by a differential scanning calorimetry (DSC) curve that further comprises a small endotherm at about 75° C. Compound I Form VIII also is characterized by its full DSC curve as substantially shown in FIG. 45.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form IX is characterized by an X-ray powder diffractogram comprising the following peaks: 6.9, 14.3, 23.7, and 24.8° 2θ±0.2° 2θ, as determined on a diffractometer using Cu-Kα radiation at a wavelength of 1.5406 Å. The diffractogram comprises additional peaks at 10.1, 21.0, and 26.9° 2θ±0.2° 2θ. Compound I Form IX is also characterized by its full X-ray powder diffractogram as substantially shown in FIG. 47. In some embodiments, the diffractogram of Compound I Form IX comprises the following peaks: 6.9, 10.1, 14.3, 21.0, 23.7, 24.8, and 26.9° 2θ±0.2° 2θ.

In some embodiments, Compound I Form IX is characterized by a differential scanning calorimetry (DSC) curve that comprises an endotherm at about 91° C. Compound I Form IX also is characterized by its full DSC curve as substantially shown in FIG. 48.

In some embodiments, Compound I is amorphous. In certain embodiments, amorphous Compound I is characterized by its full X-ray powder diffractogram as substantially shown in FIG. 50.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide esylate (Compound I Esylate Form I) is characterized by an X-ray powder diffractogram comprising the following peaks: 8.9, 23.6, and 25.9° 2θ±0.2° 2θ, as determined on a diffractometer using Cu-Kα radiation at a wavelength of 1.5406 Å. The diffractogram comprises additional peaks at 16.0 and 24.7° 2θ±0.2° 2θ. Compound I Esylate Form I is also characterized by its full X-ray diffractogram as substantially shown in FIG. 19. In some embodiments, the diffractogram of Compound I Esylate Form I comprises the following peaks: 8.9, 10.5, 10.6, 11.4, 12.9, 14.5, 16.0, 17.6, 18.6, 19.8, 20.9, 21.3, 23.6, 24.7, 25.9, and 29.3° 2θ±0.2° 2θ.

In some embodiments, Compound I Esylate Form I is characterized by a differential scanning calorimetry (DSC) curve that comprises an endotherm at about 221° C. Compound I Esylate Form I also is characterized by its full DSC curve as substantially shown in FIG. 20.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide fumarate (Compound I Fumarate Form I) is characterized by an X-ray powder diffractogram comprising the following peaks: 18.9, 23.2, and 25.6° 2θ±0.2° 2θ, as determined on a diffractometer using Cu-Kα radiation at a wavelength of 1.5406 Å. The diffractogram comprises additional peaks at 7.5 and 26.1° 2θ±0.2° 2θ. Compound I Fumarate Form I is also characterized by its full X-ray diffractogram as substantially shown in FIG. 22. In some embodiments, the diffractogram of Compound I Fumarate Form I comprises the following peaks: 7.5, 8.0, 10.2, 11.8, 12.1, 14.6, 16.0, 16.6, 16.8, 18.6, 18.9, 19.5, 20.1, 23.2, 23.6, 23.8, 24.3, 24.6, 25.6, 26.1, 27.8, and 30.3° 2θ±0.2° 2θ.

In some embodiments, Compound I Fumarate Form I is characterized by a differential scanning calorimetry (DSC) curve that comprises an endotherm at about 130° C. Compound I Fumarate Form I also is characterized by its full DSC curve as substantially shown in FIG. 23.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide glycolate (Compound I Glycolate Form I) is characterized by an X-ray powder diffractogram comprising the following peaks: 10.9, 15.1, and 25.2° 2θ±0.2° 2θ, as determined on a diffractometer using Cu-Kα radiation at a wavelength of 1.5406 Å. The diffractogram comprises additional peaks at 22.2 and 24.6° 2θ±0.2° 2θ. Compound I Glycolate Form I is also characterized by its full X-ray diffractogram as substantially shown in FIG. 25. In some embodiments, the diffractogram of Compound I Glycolate Form I comprises the following peaks: 7.5, 10.9, 14.8, 15.1, 17.1, 17.2, 20.4, 20.8, 21.6, 21.8, 22.0, 22.2, 23.1, 23.6, 24.6, 25.2, 25.5, and 28.6° 2θ±0.2° 2θ.

In some embodiments, Compound I Glycolate Form I is characterized by a differential scanning calorimetry (DSC) curve that comprises an endotherm at about 148° C. Compound I Glycolate Form I also is characterized by its full DSC curve as substantially shown in FIG. 26.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide hydrochloride (Compound I HCl Form I) is characterized by an X-ray powder diffractogram comprising the following peaks: 8.2, 26.0, and 26.1° 2θ±0.2° 2θ, as determined on a diffractometer using Cu-Kα radiation at a wavelength of 1.5406 Å. The diffractogram comprises additional peaks at 12.0 and 19.6° 2θ±0.2° 2θ. Compound I HCl Form I is also characterized by its full X-ray diffractogram as substantially shown in FIG. 28. In some embodiments, the diffractogram of Compound I HCl Form I comprises the following peaks: 8.2, 9.7, 12.0, 14.1, 14.4, 14.6, 15.3, 19.3, 19.6, 19.8, 21.6, 23.9, 26.0, 26.1, 26.3, and 28.8° 2θ±0.2° 2θ.

In some embodiments, Compound I HCl Form I is characterized by a differential scanning calorimetry (DSC) curve that comprises an endotherm at about 77° C. and an endotherm at about 191° C. Compound I HCl Form I also is characterized by its full DSC curve as substantially shown in FIG. 29.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide maleate (Compound I Maleate Form I) is characterized by an X-ray powder diffractogram comprising the following peaks: 8.7, 25.7, and 26.5° 2θ±0.2° 2θ, as determined on a diffractometer using Cu-Kα radiation at a wavelength of 1.5406 Å. The diffractogram comprises additional peaks at 17.9 and 26.6° 2θ±0.2° 2θ. Compound I Maleate Form I is also characterized by its full X-ray diffractogram as substantially shown in FIG. 31. In some embodiments, the diffractogram of Compound I Maleate Form I comprises the following peaks: 8.7, 9.0, 9.1, 10.4, 13.0, 13.5, 14.2, 14.9, 16.8, 17.9, 18.4, 19.7, 20.0, 23.2, 23.5, 25.5, 25.7, 26.5, and 26.6° 2θ±0.2° 2θ.

In some embodiments, Compound I Maleate Form I is characterized by a differential scanning calorimetry (DSC) curve that comprises an endotherm at about 152° C. Compound I Maleate Form I also is characterized by its full DSC curve as substantially shown in FIG. 32.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide mesylate (Compound I Mesylate Form I) is characterized by an X-ray powder diffractogram comprising the following peaks: 8.9, 24.5, and 25.6° 2θ±0.2° 2θ, as determined on a diffractometer using Cu-Kα radiation at a wavelength of 1.5406 Å. The diffractogram comprises additional peaks at 10.7 and 21.6° 2θ±0.2° 2θ. Compound I Mesylate Form I is also characterized by its full X-ray diffractogram as substantially shown in FIG. 34. In some embodiments, the diffractogram of Compound I Mesylate Form I comprises the following peaks: 8.9, 10.5, 10.7, 11.9, 12.8, 14.9, 16.3, 17.4, 18.4, 20.1, 20.9, 21.2, 21.6, 23.9, 24.5, 25.6, 25.8, 26.8, and 30.1° 2θ±0.2° 2θ.

In some embodiments, Compound I Mesylate Form I is characterized by a differential scanning calorimetry (DSC) curve that comprises an endotherm below 0° C., an endotherm below 100° C., and an endotherm at about 232° C. Compound I Mesylate Form I also is characterized by its full DSC curve as substantially shown in FIG. 35.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide oxalate (Compound I Oxalate Form I) is characterized by an X-ray powder diffractogram comprising the following peaks: 13.3, 13.5, and 26.0° 2θ±0.2° 2θ, as determined on a diffractometer using Cu-Kα radiation at a wavelength of 1.5406 Å. The diffractogram comprises additional peaks at 7.3 and 24.5° 2θ±0.2° 2θ. Compound I Oxalate Form I is also characterized by its full X-ray diffractogram as substantially shown in FIG. 37. In some embodiments, the diffractogram of Compound I Oxalate Form I comprises the following peaks: 7.3, 9.5, 12.1, 12.2, 13.3, 13.5, 13.9, 17.9, 19.9, 20.3, 20.8, 21.4, 21.6, 22.2, 23.9, 24.5, 25.5, 25.7, and 26.0° 2θ±0.2° 2θ.

In some embodiments, Compound I Oxalate Form I is characterized by a differential scanning calorimetry (DSC) curve that comprises an endotherm at about 216° C. Compound I Oxalate Form I also is characterized by its full DSC curve as substantially shown in FIG. 38.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide sulfate (Compound I Sulfate Form I) is characterized by an X-ray powder diffractogram comprising the following peaks: 7.1, 13.8, and 25.5° 2θ±0.2° 2θ, as determined on a diffractometer using Cu-Kα radiation at a wavelength of 1.5406 Å. The diffractogram comprises additional peaks at 17.0 and 21.2° 2θ±0.2° 2θ. Compound I Sulfate Form I is also characterized by its full X-ray powder diffractogram as substantially shown in FIG. 40. In some embodiments, the diffractogram of Compound I Sulfate Form I comprises the following peaks: 7.1, 9.1, 9.3, 10.8, 12.2, 13.1, 13.4, 13.8, 17.0, 18.1, 18.2, 20.4, 21.0, 21.2, 25.4, 25.5, 26.9, 27.8, and 26.9° 2θ±0.2° 2θ.

Figure 51:
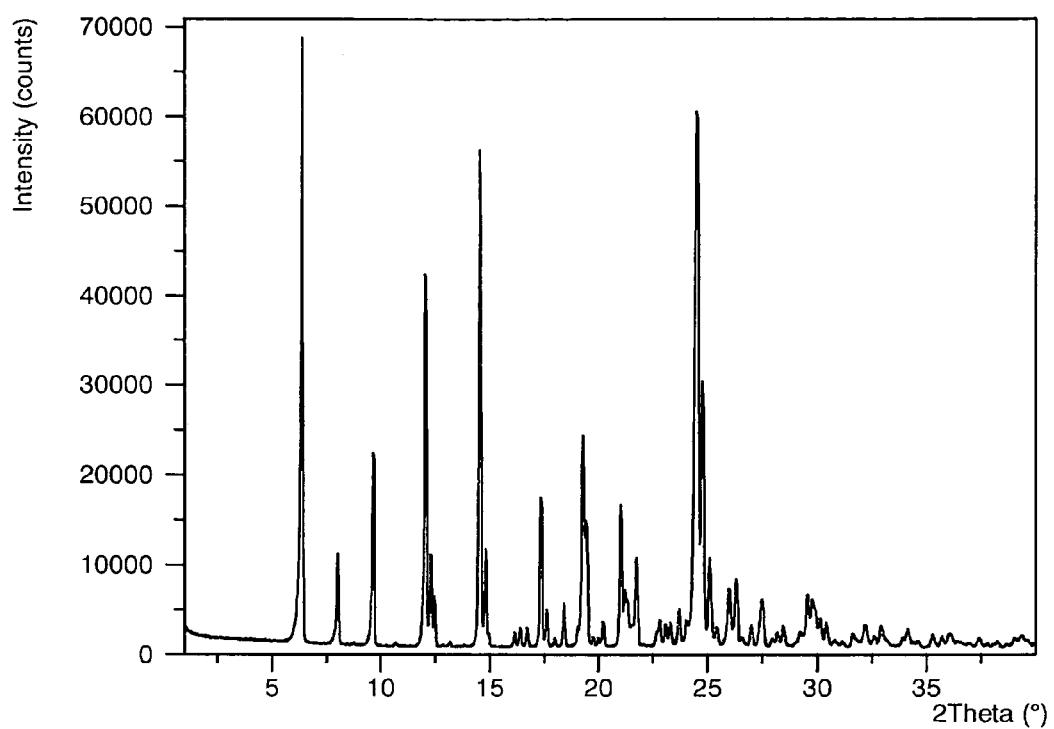
FIG. 51 shows an X-ray powder diffraction (XRPD) of Compound I Adipate Form I.

Crystalline 5-(4-cyclopropyl-1H-imidazol-1-yl)-N-(6-(4-isopropyl-4H-1,2,4-triazol-3-yl)pyridin-2-yl)-2-fluoro-4- methylbenzamide adipate (Compound I Adipate Form I) is characterized by an X-ray powder diffractogram comprising the following peaks: 6.4, 14.6, and 24.5° 2θ±0.2° 2θ, as determined on a diffractometer using Cu-Kα radiation at a wavelength of 1.5406 Å. The diffractogram comprises additional peaks at 9.7, 12.1, and 19.3° 2θ±0.2° 2θ. Compound I Adipate Form I is also characterized by its full X-ray diffractogram as substantially shown in FIG. 51. In some embodiments, the diffractogram of Compound I Adipate Form I comprises the following peaks: 6.4, 8.1, 9.7, 12.1, 14.6, 17.4, 19.3, and 24.5° 2θ±0.2° 2θ.

In some embodiments, Compound I Adipate Form I is characterized by a differential scanning calorimetry (DSC) curve that comprises an endotherm at about 151° C. Compound I Adipate Form I also is characterized by its full DSC curve as substantially shown in FIG. 52.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide besylate (Compound I Besylate Form I) is characterized by an X-ray powder diffractogram comprising the following peaks: 6.9, 10.8, and 12.9° 2θ±0.2° 2θ, as determined on a diffractometer using Cu-Kα radiation at a wavelength of 1.5406 Å. The diffractogram comprises additional peaks at 10.2, 20.9, and 25.4° 2θ±0.2° 2θ. Compound I Besylate Form I is also characterized by its full X-ray diffractogram as substantially shown in FIG. 54. In some embodiments, the diffractogram of Compound I Besylate Form I comprises the following peaks: 6.9, 10.2, 10.8, 12.9, 16.4, 20.9, 25.4, and 25.9° 2θ±0.2° 2θ.

Figure 55:
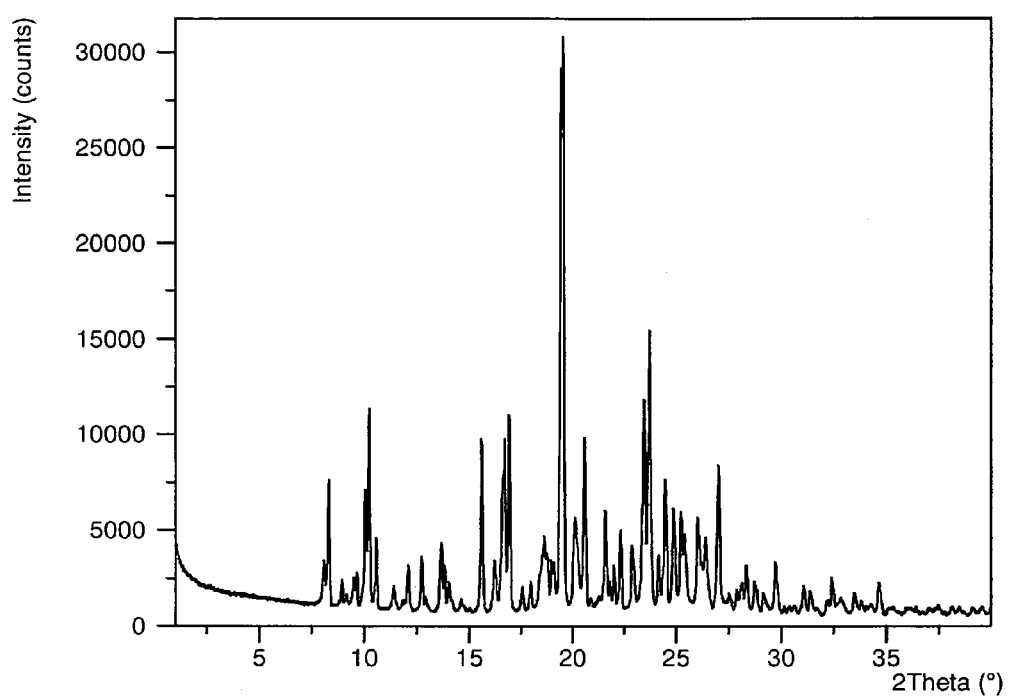
FIG. 55 shows an X-ray powder diffraction (XRPD) of Compound I Edisylate Form I.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide edisylate (Compound I Edisylate Form I) is characterized by an X-ray powder diffractogram comprising the following peaks: 10.3, 16.9, 19.5, and 23.7° 2θ±0.2° 2θ, as determined on a diffractometer using Cu-Kα radiation at a wavelength of 1.5406 Å. The diffractogram comprises additional peaks at 15.6 and 26.0° 2θ±0.2° 2θ. Compound I Edisylate Form I is also characterized by its full X-ray diffractogram as substantially shown in FIG. 55. In some embodiments, the diffractogram of Compound I Edisylate Form I comprises the following peaks: 8.3, 10.3, 15.6, 16.9, 19.5, 23.7, and 26.0° 2θ±0.2° 2θ.

In some embodiments, Compound I Edisylate Form I is characterized by a differential scanning calorimetry (DSC) curve that comprises an endotherm at about 240° C. In some embodiments, Compound I Edisylate Form I is characterized by a differential scanning calorimetry (DSC) curve that further comprises an endotherm below 100° C. Compound I Edisylate Form I also is characterized by its full DSC curve as substantially shown in FIG. 56.

Figure 58:
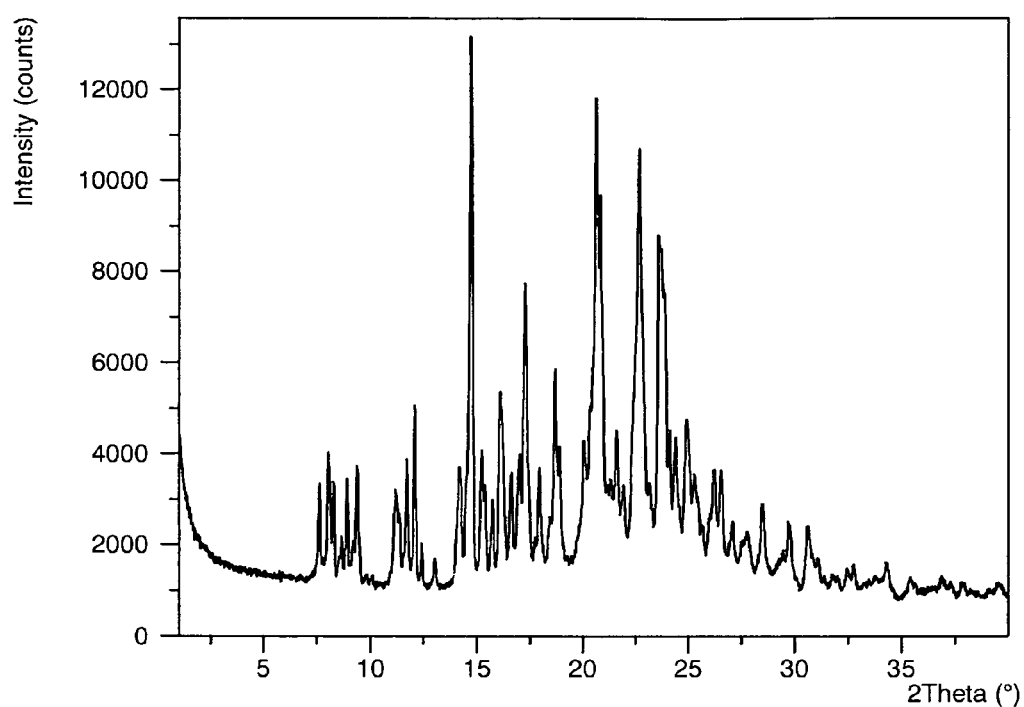
FIG. 58 shows an X-ray powder diffraction (XRPD) of Compound I Edisylate Form II.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide edisylate (Compound I Edisylate Form II) is characterized by an X-ray powder diffractogram comprising the following peaks: 14.7, 20.6, and 22.7° 2θ±0.2° 2θ, as determined on a diffractometer using Cu-Kα radiation at a wavelength of 1.5406 Å. The diffractogram comprises additional peaks at 12.1, 17.3, and 23.6° 2θ±0.2° 2θ. Compound I Edisylate Form II is also characterized by its full X-ray diffractogram as substantially shown in FIG. 58. In some embodiments, the diffractogram of Compound I Edisylate Form II comprises the following peaks: 8.1, 9.4, 12.1, 14.7, 17.3, 20.6, 22.7, and 23.6° 2θ±0.2° 2θ.

In some embodiments, Compound I Edisylate Form II is characterized by a differential scanning calorimetry (DSC) curve that comprises an endotherm at about 178° C. In some embodiments, Compound I Edisylate Form II is character-ized by a differential scanning calorimetry (DSC) curve that further comprises an endotherm at about 91° C. and about 150° C. Compound I Edisylate Form II also is characterized by its full DSC curve as substantially shown in FIG. 59.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide gentisate (Compound I Gentisate Form I) is characterized by an X-ray powder diffractogram comprising the following peaks: 9.7, 12.5, and 26.2° 2θ±0.2° 2θ, as determined on a diffractometer using Cu-Kα radiation at a wavelength of 1.5406 Å. The diffractogram comprises additional peaks at 18.9 and 20.4° 2θ±0.2° 2θ. Compound I Gentisate Form I is also characterized by its full X-ray diffractogram as substantially shown in FIG. 61. In some embodiments, the diffractogram of Compound I Gentisate Form I comprises the following peaks: 9.7, 12.5, 18.9, 20.4, and 26.2° 2θ±0.2° 2θ.

Figure 62:
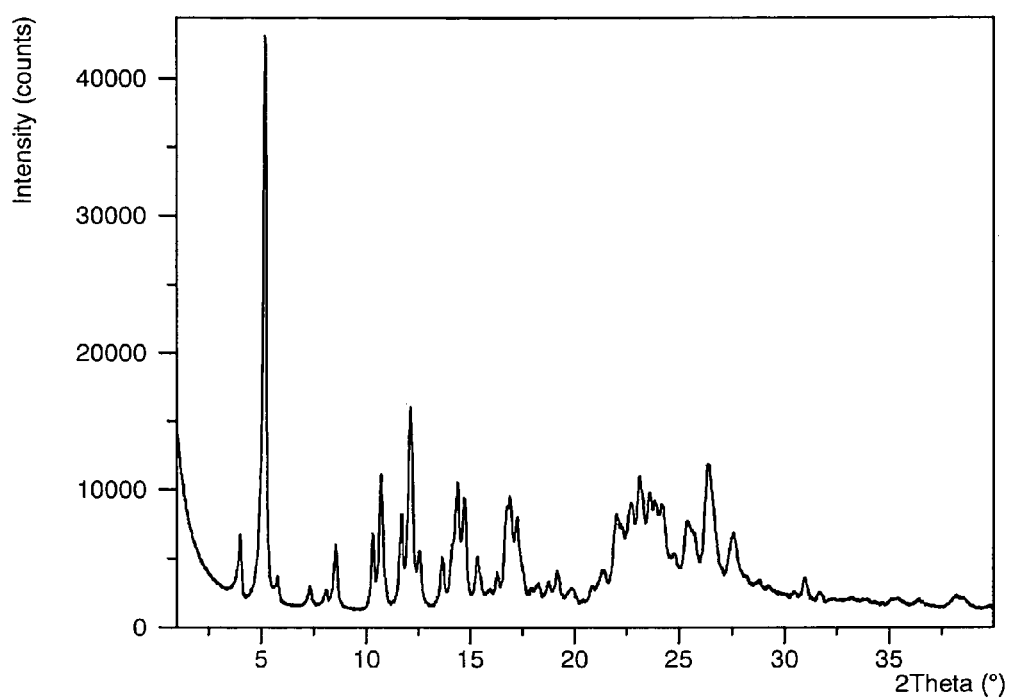
FIG. 62 shows an X-ray powder diffraction (XRPD) of Compound I Gentisate Form II.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide gentisate (Compound I Gentisate Form II) is characterized by an X-ray powder diffractogram comprising the following peaks: 5.2, 10.7, and 12.1° 2θ±0.2° 2θ, as determined on a diffractometer using Cu-Kα radiation at a wavelength of 1.5406 Å. The diffractogram comprises additional peaks at 14.4, 16.9, and 26.3° 2θ±0.2° 2θ. Compound I Gentisate Form II is also characterized by its full X-ray diffractogram as substantially shown in FIG. 62. In some embodiments, the diffractogram of Compound I Gentisate Form II comprises the following peaks: 5.2, 10.7, 12.1, 14.4, 16.9, and 26.3° 2θ±0.2° 2θ.

In some embodiments, Compound I Gentisate Form II is characterized by a differential scanning calorimetry (DSC) curve that comprises an endotherm at about 95° C. and about 134° C. Compound I Gentisate Form II also is characterized by its full DSC curve as substantially shown in FIG. 63.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide glutarate (Compound I Glutarate Form I) is characterized by an X-ray powder diffractogram comprising the following peaks: 7.5, 20.8, and 23.3° 2θ±0.2° 2θ, as determined on a diffractometer using Cu-Kα radiation at a wavelength of 1.5406 Å. The diffractogram comprises additional peaks at 14.7, 15.8, and 26.1° 2θ±0.2° 2θ. Compound I Glutarate Form I is also characterized by its full X-ray diffractogram as substantially shown in FIG. 65. In some embodiments, the diffractogram of Compound I Glutarate Form I comprises the following peaks: 7.5, 10.6, 14.7, 15.8, 18.0, 20.8, 23.3, and 26.1° 2θ±0.2° 2θ.

In some embodiments, Compound I Glutarate Form I is characterized by a differential scanning calorimetry (DSC) curve that comprises an endotherm at about 129° C. In some embodiments, Compound I Glutarate Form I is characterized by a differential scanning calorimetry (DSC) curve that further comprises an endotherm at about 66° C. and at about 89° C. Compound I Glutarate Form I also is characterized by its full DSC curve as substantially shown in FIG. 66.

Figure 68:
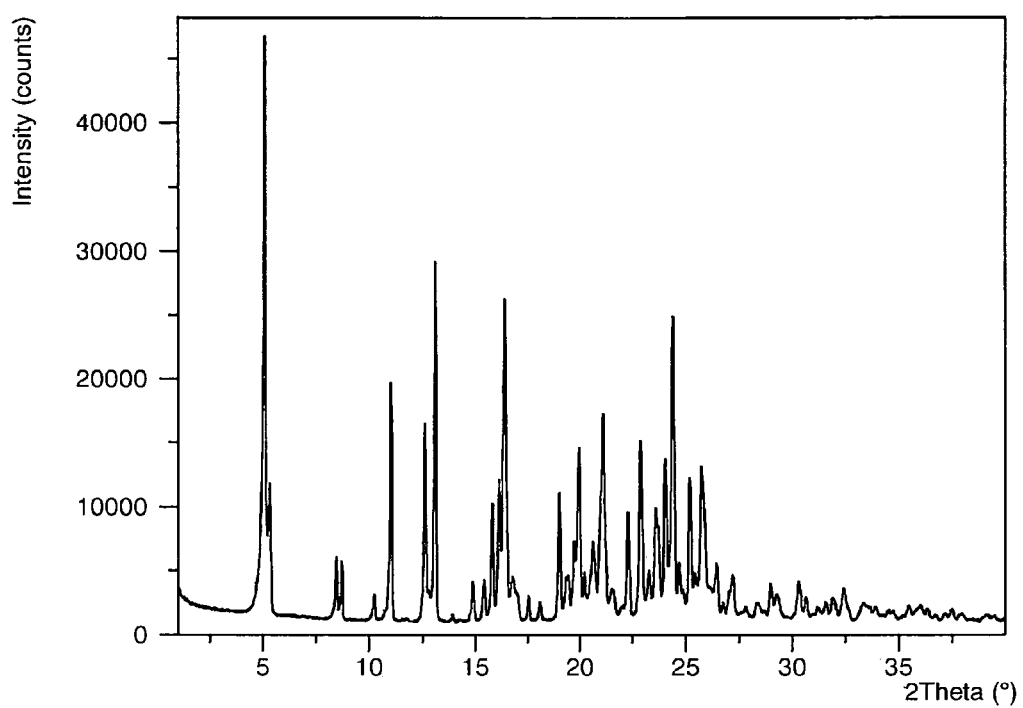
FIG. 68 shows an X-ray powder diffraction (XRPD) of Compound I Glutarate Form II.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide glutarate (Compound I Glutarate Form II) is characterized by an X-ray powder diffractogram comprising the following peaks: 5.1, 13.1, and 16.4° 2θ±0.2° 2θ, as determined on a diffractometer using Cu-Kα radiation at a wavelength of 1.5406 Å. The diffractogram comprises additional peaks at 11.0, 12.6, and 24.4° 2θ±0.2° 2θ. Compound I Glutarate Form II is also characterized by its full X-ray diffractogram as substantially shown in FIG. 68. In some embodiments, the diffractogram of Compound I Glutarate Form II comprises the following peaks: 5.1, 11.0, 12.6, 13.1, 16.4, 21.1, and 24.4° 2θ±0.2° 2θ.

In some embodiments, Compound I Glutarate Form II is characterized by a differential scanning calorimetry (DSC) curve that comprises an endotherm at about 106° C. and at about 127° C. Compound I Glutarate Form II also is characterized by its full DSC curve as substantially shown in FIG. 69.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide L-tartrate (Compound I L-Tartrate Form I) is characterized by an X-ray powder diffractogram comprising the following peaks: 4.3, 12.4, and 24.8° 2θ±0.2° 2θ, as determined on a diffractometer using Cu-Kα radiation at a wavelength of 1.5406 Å. The diffractogram comprises additional peaks at 9.1, 21.2, and 27.4° 2θ±0.2° 2θ.

Figure 71:
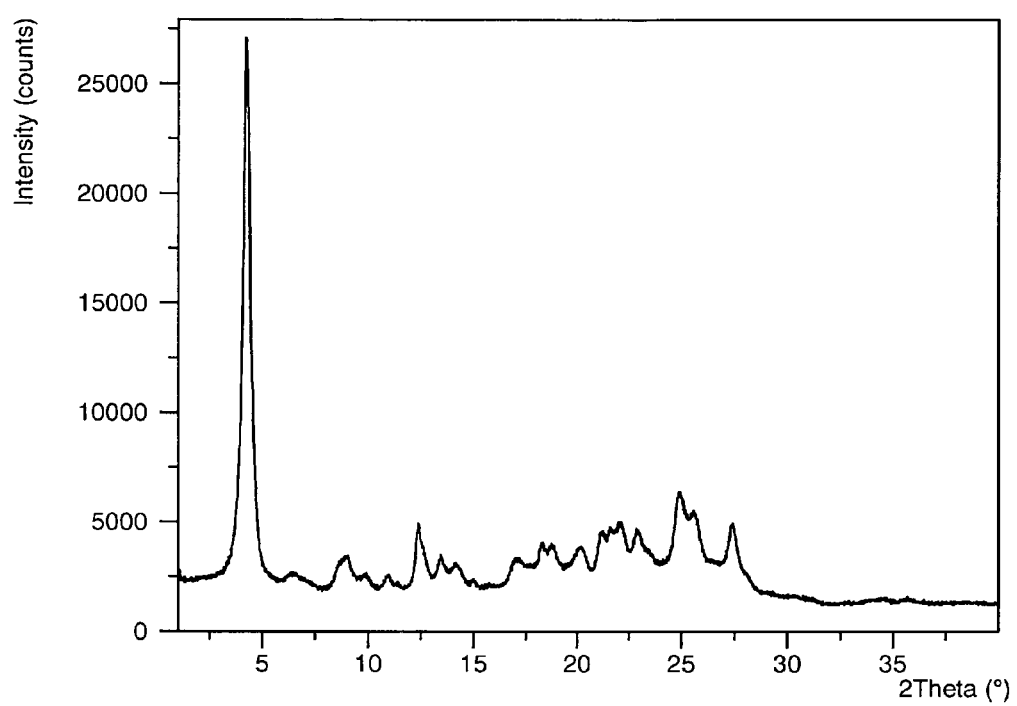
FIG. 71 shows an X-ray powder diffraction (XRPD) of Compound I L-Tartrate Form I.

Compound I L-Tartrate Form I is also characterized by its full X-ray diffractogram as substantially shown in FIG. 71. In some embodiments, the diffractogram of Compound I L-Tartrate Form I comprises the following peaks: 4.3, 9.1, 12.4, 18.3, 21.2, 24.8, and 27.4° 2θ±0.2° 2θ.

In some embodiments, Compound I L-Tartrate Form I is characterized by a differential scanning calorimetry (DSC) curve that comprises an endotherm at about 61° C. In some embodiments, Compound I L-Tartrate Form I is characterized by a differential scanning calorimetry (DSC) curve that further comprises an endotherm at about 128° C. Compound I L-Tartrate Form I also is characterized by its full DSC curve as substantially shown in FIG. 72.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide L-tartrate (Compound I L-Tartrate Form II) is characterized by an X-ray powder diffractogram comprising the following peaks: 4.7, 9.9, 11.4 and 22.0° 2θ±0.2° 2θ, as determined on a diffractometer using Cu-Kα radiation at a wavelength of 1.5406 Å. The diffractogram comprises additional peaks at 7.1, 24.2, and 25.2° 2θ±0.2° 2θ. Compound I L-Tartrate Form II is also characterized by its full X-ray diffractogram as substantially shown in FIG. 74. In some embodiments, the diffractogram of Compound I L-Tartrate Form II comprises the following peaks: 4.7, 7.1, 9.9, 11.4, 22.0, 24.2, and 25.2° 2θ±0.2° 2θ.

In some embodiments, Compound I L-Tartrate Form II is characterized by a differential scanning calorimetry (DSC) curve that comprises an endotherm at about 121° C. In some embodiments, Compound I L-Tartrate Form II is characterized by a differential scanning calorimetry (DSC) curve that further comprises an endotherm below 110° C. Compound I L-Tartrate Form II also is characterized by its full DSC curve as substantially shown in FIG. 75.

Figure 77:
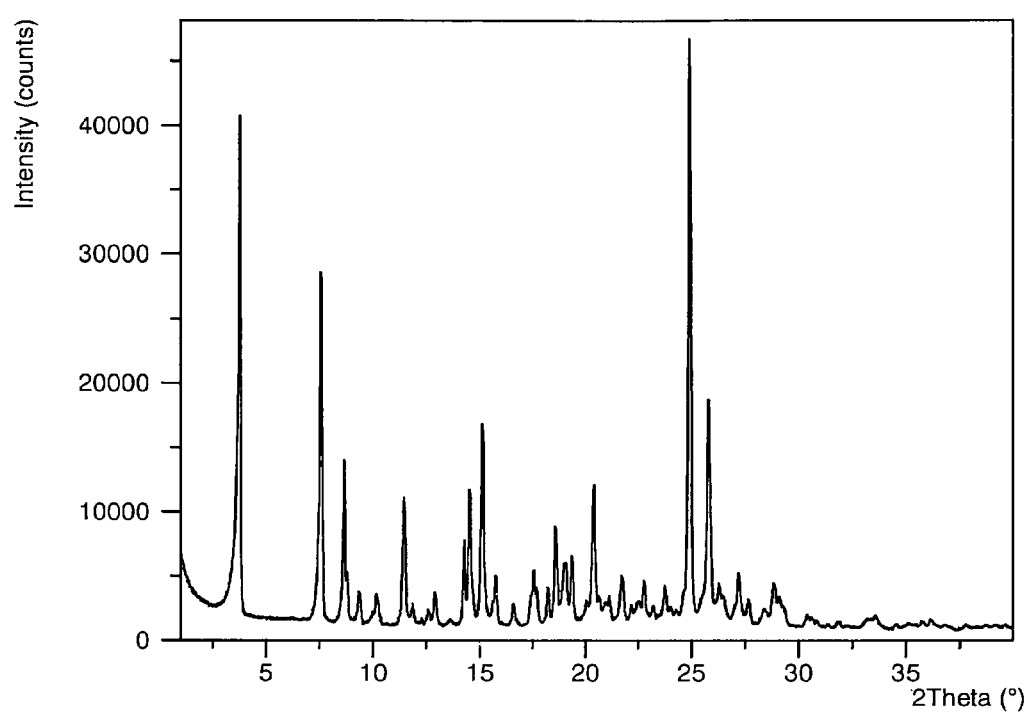
FIG. 77 shows an X-ray powder diffraction (XRPD) of Compound I Propyl Gallate Form I.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide propyl gallate (Compound I Propyl Gallate Form I) is characterized by an X-ray powder diffractogram comprising the following peaks: 3.8, 7.6, and 24.9° 2θ±0.2° 2θ, as determined on a diffractometer using Cu-Kα radiation at a wavelength of 1.5406 Å. The diffractogram comprises additional peaks at 8.7, 15.1, and 25.8° 2θ±0.2° 2θ. Compound I Propyl Gallate Form I is also characterized by its full X-ray diffractogram as substantially shown in FIG. 77. In some embodiments, the diffractogram of Compound I Propyl Gallate Form I comprises the following peaks: 3.8, 7.6, 8.7, 11.5, 15.1, 20.4, 24.9, and 25.8° 2θ±0.2° 2θ.

In some embodiments, Compound I Propyl Gallate Form I is characterized by a differential scanning calorimetry (DSC) curve that comprises an endotherm at about 164° C.

In some embodiments, Compound I Propyl Gallate Form I is characterized by a differential scanning calorimetry (DSC) curve that further comprises an endotherm below 100° C. Compound I Propyl Gallate Form I also is characterized by its full DSC curve as substantially shown in FIG. 78.

Figure 80:
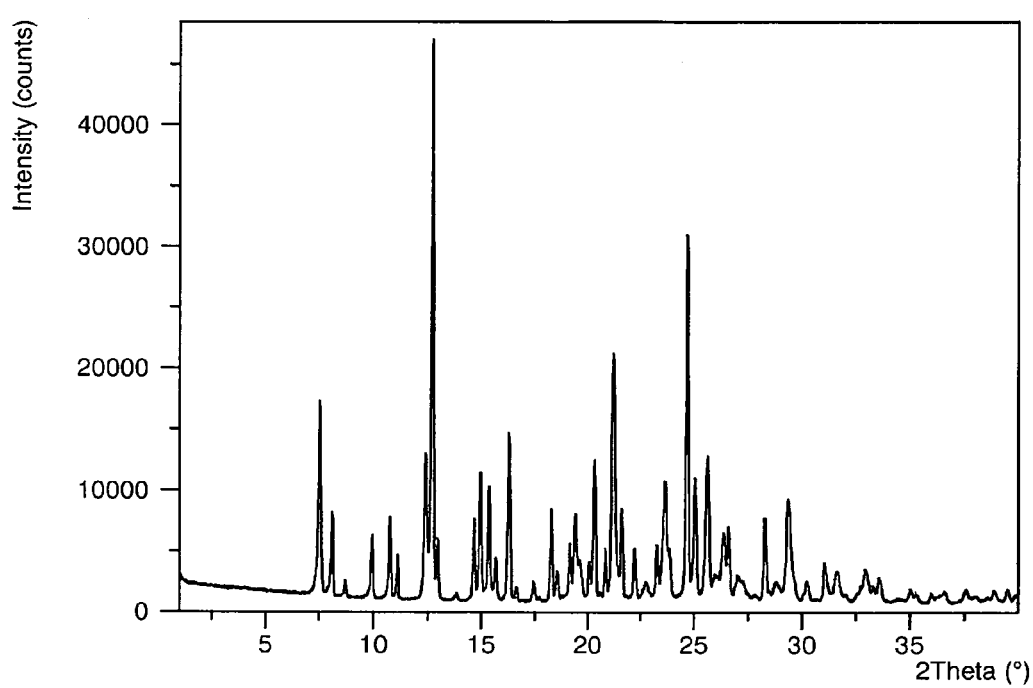
FIG. 80 shows an X-ray powder diffraction (XRPD) of Compound I Succinate Form I.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide succinate (Compound I Succinate Form I) is characterized by an X-ray powder diffractogram comprising the following peaks: 12.7, 21.2, and 24.7° 2θ±0.2° 2θ, as determined on a diffractometer using Cu-Kα radiation at a wavelength of 1.5406 Å. The diffractogram comprises additional peaks at 7.6, 12.4, and 16.3° 2θ±0.2° 2θ. Compound I Succinate Form I is also characterized by its full X-ray diffractogram as substantially shown in FIG. 80. In some embodiments, the diffractogram of Compound I Succinate Form I comprises the following peaks: 7.6, 12.4, 12.7, 16.3, 20.3, 21.2, and 24.7° 2θ±0.2° 2θ.

In some embodiments, Compound I Succinate Form I is characterized by a differential scanning calorimetry (DSC) curve that comprises an endotherm at about 152° C. In some embodiments, Compound I Succinate Form I is characterized by a differential scanning calorimetry (DSC) curve that further comprises an endotherm below 120° C. Compound I Succinate Form I also is characterized by its full DSC curve as substantially shown in FIG. 81.

Figure 83:
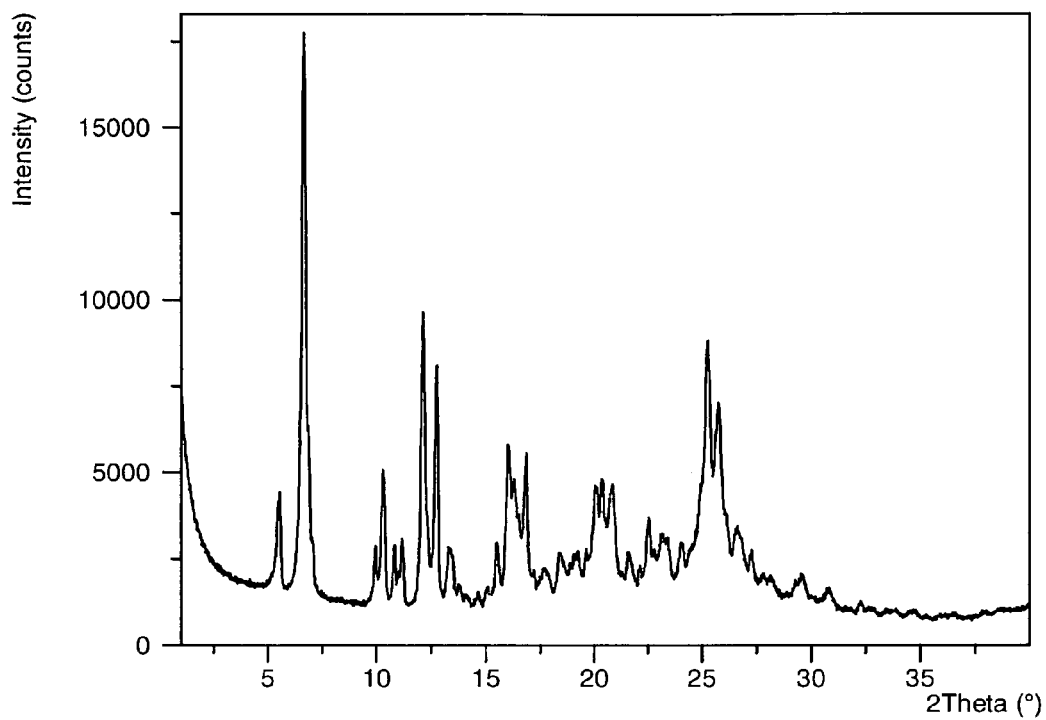
FIG. 83 shows an X-ray powder diffraction (XRPD) of Compound I Tosylate Form I.

Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide tosylate (Compound I Tosylate Form I) is characterized by an X-ray powder diffractogram comprising the following peaks: 6.6, 12.1, and 12.8° 2θ±0.2° 2θ, as determined on a diffractometer using Cu-Kα radiation at a wavelength of 1.5406 Å. The diffractogram comprises additional peaks at 10.3, 16.0, and 25.2° 2θ±0.2° 2θ. Compound I Tosylate Form I is also characterized by its full X-ray diffractogram as substantially shown in FIG. 83. In some embodiments, the diffractogram of Compound I Tosylate Form I comprises the following peaks: 5.6, 6.6, 10.3, 12.1, 12.8, 16.0, and 25.2° 2θ±0.2° 2θ.

In some embodiments, Compound I Tosylate Form I is characterized by a differential scanning calorimetry (DSC) curve that comprises an endotherm at about 131° C. In some embodiments, Compound I Tosylate Form I is characterized by a differential scanning calorimetry (DSC) curve that further comprises an endotherm below 120° C. Compound I Tosylate Form I also is characterized by its full DSC curve as substantially shown in FIG. 84.

Some embodiments are directed to compositions comprising a form of Compound I as described herein and remains free of any other forms of Compound I. In some embodiments, a composition comprises greater than 95% of a form of Compound I as described herein and remains free of any other forms of Compound I. In some embodiments, a composition comprises greater than 97% of a form of Compound I as described herein and remains free of any other forms of Compound I. In some embodiments, a composition comprises greater than 99% a form of Compound I as described herein and remains free of any other forms of Compound I.

Some embodiments are directed to compositions comprising a crystalline form of Compound I Form I as described herein and remains free of any other forms of Compound I. In some embodiments, a composition comprises greater than 95% of a crystalline form of Compound I Form I as described herein and remains free of any other forms of Compound I Form I. In some embodiments, a composition comprises greater than 97% of a crystalline form of Compound I Form I as described herein and remains free of any other forms of Compound I Form I. In some embodiments, a composition comprises greater than 99% a crystalline form of Compound I Form I as described herein and remains free of any other forms of Compound I.

Some embodiments are directed to processes for making forms of Compound I as described herein. In some embodiments, the processes are as described in the Examples provided herein.

In another embodiment, the disclosure provides a process for making Compound I Form I. The process comprises the step of contacting Compound I with a solvent selected from the group consisting of ethanol, a mixture of methanol and water, a mixture of methanol and methyl tert-butyl ether, a mixture of isopropyl acetate and n-heptane, a mixture of methyl tert-butyl ether and n-heptane, and a mixture of ethanol and n-heptane, whereby Compound I Form I is formed.

In another embodiment, the disclosure provides a process for making Compound I Form V. The process comprises the step of contacting Compound I with dichloromethane and n-heptane, whereby Compound I Form V is formed. Still another embodiment is a process for making Compound I Form II. The process comprises the step of desolvating Compound I Form V, whereby Compound I Form II is formed.

Another embodiment is a process for making Compound I Form III. The process comprises the step of contacting Compound I with a mixture of methanol and water, whereby Compound I Form III is formed. In some embodiments, the ratio of methanol to water may be about 1:4.

Another embodiment is a process for making Compound I Form IV. The process comprises the step of contacting Compound I with a mixture of methanol and water, whereby Compound I Form IV is formed. In some embodiments, the ratio of methanol to water may be about 4:3.

In another embodiment, the disclosure provides a process for making Compound I Form VI. The process comprises the step of evaporating Compound I from a solvent, whereby Compound I Form VI is formed. The solvent may be acetonitrile, ethanol, tetrahydrofuran, methanol/methyl isobutyl ketone, and MeOH/1-butanol. In some embodiments, the process further comprises heating. In some embodiments, the process for making Compound I Form VI comprises contacting Compound I in ethanol with heptane, whereby Compound I Form VI is formed.

Another embodiment is a process for making Compound I Form VII. The process comprises the step of dehydrating Compound I Form IV, whereby Compound I Form VII is formed.

Another embodiment is a process for making Compound I Form VII. The process comprises the step of dehydrating Compound I Form IV, whereby Compound I Form VII is formed.

Another embodiment is a process for making Compound I Form VIII. The process comprises the step of equilibrating Compound I Form VI under humid conditions, whereby Compound I Form VIII is formed. In other embodiments, the process comprises contacting Compound I Form VI with ethanol and water, whereby Compound I Form VIII is formed.

Another embodiment is a process for making Compound I Form IX. The process comprises the step of contacting Compound I with acetic acid, whereby Compound I Form IX is formed.

Another embodiment is a process for making amorphous Compound I. The process comprises the step of evaporating Compound I from dichloromethane or methanol.

Another embodiment is a process for making Compound I Esylate Form I. The process comprises the step of contacting Compound I with ethanol and ethanesulfonic acid, whereby Compound I Esylate Form I is formed.

Another embodiment is a process for making Compound I Fumarate Form I. The process comprises the step of contacting Compound I with ethanol and fumaric acid, whereby Compound I Fumarate Form I is formed.

Another embodiment is a process for making Compound I Glycolate Form I. The process comprises the step of contacting Compound I with ethanol and glycolic acid, whereby Compound I Glycolate Form I is formed.

Another embodiment is a process for making Compound I HCl Form I. The process comprises the step of contacting Compound I with ethanol and hydrochloric acid, whereby Compound I HCl Form I is formed.

Another embodiment is a process for making Compound I Maleate Form I. The process comprises the step of contacting Compound I with acetonitrile and maleic acid, whereby Compound I Maleate Form I is formed.

Another embodiment is a process for making Compound I Oxalate Form I. The process comprises the step of contacting Compound I with ethanol and oxalate acid, whereby Compound I Oxalate Form I is formed.

Another embodiment is a process for making Compound I Sulfate Form I. The process comprises the step of contacting Compound I with dichloromethane and sulfuric acid, whereby Compound I Sulfate Form I is formed.

Another embodiment is a process for making Compound I Adipate Form I. The process comprises the step of contacting Compound I with acetonitrile and adipic acid, whereby Compound I Adipate Form I is formed.

Another embodiment is a process for making Compound I Besylate Form I. The process comprises the step of contacting Compound I with ethanol and benzenesulfonic acid, whereby Compound I Besylate Form I is formed.

Another embodiment is a process for making Compound I Edisylate Form I. The process comprises the step of contacting Compound I with ethanol and ethanedisulfonic acid, whereby Compound I Edisylate Form I is formed.

Another embodiment is a process for making Compound I Edisylate Form II. The process comprises the step of contacting Compound I with ethanol and ethanedisulfonic acid, whereby Compound I Edisylate Form II is formed.

Another embodiment is a process for making Compound I Gentisate Form I. The process comprises the step of contacting Compound I with ethanol and gentisic acid, whereby Compound I Gentisate Form I is formed. Another embodiment is a process for making Compound I Gentisate Form II. The process comprises the step of contacting Compound I with ethanol and gentisic acid, whereby Compound I Gentisate Form II is formed.

Another embodiment is a process for making Compound I Glutarate Form I. The process comprises the step of contacting Compound I with dichloromethane and glutaric acid, whereby Compound I Glutarate Form I is formed.

Another embodiment is a process for making Compound I Glutarate Form II. The process comprises the step of contacting Compound I with ethanol and glutaric acid, whereby Compound I Glutarate Form II is formed.

Another embodiment is a process for making Compound I L-Tartrate Form I. The process comprises the step of contacting Compound I with ethanol and L-tartric acid, whereby Compound I L-Tartrate Form I is formed.

Another embodiment is a process for making Compound I L-Tartrate Form II. The process comprises the step of contacting Compound I with ethanol and L-tartric acid, whereby Compound I L-Tartrate Form II is formed.

Another embodiment is a process for making Compound I Propyl Gallate Form I. The process comprises the step of contacting Compound I with ethanol and propyl gallate, whereby Compound I Propyl Gallate Form I is formed.

Another embodiment is a process for making Compound I Succinate Form I. The process comprises the step of contacting Compound I with acetonitrile and succinic acid, whereby Compound I Succinate Form I is formed.

Another embodiment is a process for making Compound I Tosylate Form I. The process comprises the step of contacting Compound I with ethanol and p-toluenesulfonic acid, whereby Compound I Tosylate Form I is formed.

Pharmaceutical Compositions and Modes of Administration

The forms of Compound I as described herein may be administered in the form of a pharmaceutical composition. Thus, provided herein are also pharmaceutical compositions that contain one or more of the forms of Compound I described herein and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.). The pharmaceutical compositions may be administered alone or in combination with other therapeutic agents.

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of one or more of the forms of Compound I described herein. Administration may be via, for example, capsule or enteric coated tablets. In making the pharmaceutical compositions that include one or more of the forms of Compound I described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active ingredient, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include one or more of the forms of Compound I described herein can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the forms of Compound I described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of the forms of Compound I described herein. When referring to these preformulation compositions as homogeneous, the active ingredient may be dispersed evenly throughout the composition so that the composition may be readily subdivided into equally effective unit dosage forms such as tablets, pills and capsules.

The tablets or pills of the forms of Compound I described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

The forms of Compound I as described herein may be administered in a pharmaceutically effective amount. For oral administration, each dosage unit can contain from 1 mg to 2 gram, 1 mg to 1 gram, or 1 mg to 500 mg of Compound I. In some embodiments, the dose is from 1 mg to 250 mg of Compound I. In some embodiments, a dose of Compound I ranges from about 20 mg twice a day to about 50 mg twice a day. In some embodiments, the dose is 2 mg, 4 mg, 6 mg, 8 mg, 10 mg, 12 mg, 14 mg, 16 mg, 18 mg, 20 mg, 25 mg, 25 mg, 30 mg, 35 mg, 40 mg, 45 mg, 50 mg, 75 mg, 100 mg, 200 mg, or 500 mg of Compound I. It will be understood, however, that the amount of the compound actually administered usually will be determined by a physician in light of the relevant circumstances including the condition to be treated, the chosen route of administration, and co-administration compound and if applicable, the age, weight, response of the individual patient, the severity of the patient's symptoms, and the like.

The forms of Compound I of the present application or the compositions thereof may be administered once, twice, three, or four times daily, using any suitable mode described above. Also, the forms of Compound I of the present application or the compositions thereof may be administered once or twice a week, once every two weeks, once every three weeks, once every four weeks, once every five weeks, or once every six weeks. In some embodiments, the forms of Compound I of the present application or the compositions thereof may be administered once daily for 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, or longer as needed.

The forms of Compound I of the present application or the compositions thereof may be administered under fed conditions. The term "fed conditions" or variations thereof refers to the consumption or uptake of food, in either solid or liquid forms, or calories, in any suitable form, before or at the same time when the active ingredients are administered. For example, the forms of Compound I of the present application or the compositions thereof may be administered to the subject (e.g., a human) within minutes or hours of consuming calories (e.g., a meal). In some embodiments, the forms of Compound I of the present application or the compositions thereof may be administered to the subject (e.g., a human) within 5-10 minutes, about 30 minutes, or about 60 minutes of consuming calories.

ASK 1 and Methods of Use

Apoptosis signal-regulating kinase 1 (ASK1) is a member of the mitogen-activated protein kinase kinase kinase ("MAP3K") family that activates the c-Jun N-terminal protein kinase ("JNK") and p38 MAP kinase (Ichijo, H., Nishida, E., Irie, K., Dijke, P. T., Saitoh, M., Moriguchi, T., Matsumoto, K., Miyazono, K., and Gotoh, Y. (1997) *Science,* 275, 90-94). ASK1 is activated by a variety of stimuli including oxidative stress, reactive oxygen species (ROS), LPS, TNF-α, FasL, ER stress, and increased intracellular calcium concentrations (Hattori, K., Naguro, I., Runchel, C., and Ichijo, H. (2009) *Cell Comm. Signal.* 7:1-10; Takeda, K., Noguchi, T., Naguro, I., and Ichijo, H. (2007) *Annu. Rev. Pharmacol. Toxicol.* 48: 1-8.27; Nagai, H., Noguchi, T., Takeda, K., and Ichijo, I. (2007) *J. Biochem. Mol. Biol.* 40:1-6). Phosphorylation of ASK1 protein can lead to apoptosis or other cellular responses depending on the cell type. ASK1 activation and signaling have been reported to play an important role in a broad range of diseases including neurodegenerative, cardiovascular, inflammatory, autoimmune, and metabolic disorders. In addition, ASK1 has been implicated in mediating organ damage following ischemia and reperfusion of the heart, brain, and kidney (Watanabe et al. (2005) *BBRC* 333, 562-567; Zhang et al., (2003) Life Sci 74-37-43; Terada et al. (2007) *BBRC* 364: 1043-49).

ROS are reported be associated with increases of inflammatory cytokine production, fibrosis, apoptosis, and necrosis in the kidney. (Singh D K, Winocour P, Farrington K. Oxidative stress in early diabetic nephropathy: fueling the fire. *Nat Rev Endocrinol* 2011 March; 7(3):176-184; Brownlee M. Biochemistry and molecular cell biology of diabetic complications. *Nature* 2001 Dec. 13; 414(6865):813-820; Mimura I, Nangaku M. The suffocating kidney: tubulointerstitial hypoxia in end-stage renal disease. *Nat Rev Nephrol* 2010 November; 6(11):667-678).

Moreover, oxidative stress facilitates the formation of advanced glycation end-products (AGEs) that cause further renal injury and production of ROS. (Hung K Y, et al. N-acetylcysteine-mediated antioxidation prevents hyperglycemia-induced apoptosis and collagen synthesis in rat mesangial cells. *Am J Nephrol* 2009; 29(3):192-202).

Tubulointerstitial fibrosis in the kidney is a strong predictor of progression to renal failure in patients with chronic kidney diseases (Schainuck L I, et al. Structural-functional correlations in renal disease. Part II: The correlations. *Hum Pathol* 1970; 1: 631-641.). Unilateral ureteral obstruction (UUO) in rats is a widely used model of tubulointerstitial fibrosis. UUO causes tubulointerstital inflammation, increased expression of transforming growth factor beta (TGF-β), and accumulation of myofibroblasts, which secrete matrix proteins such as collagen and fibronectin. The UUO model can be used to test for a drug's potential to treat chronic kidney disease by inhibiting renal fibrosis (Chevalier et al., Ureteral obstruction as a model of renal interstitial fibrosis and obstructive nephropathy, *Kidney International* (2009) 75, 1145-1152.

Thus, therapeutic agents that function as inhibitors of ASK1 signaling have the potential to remedy or improve the lives of patients in need of treatment for diseases or conditions such as neurodegenerative, cardiovascular, inflammatory, autoimmune, and metabolic disorders. In particular, ASK1 inhibitors have the potential to treat cardio-renal diseases, including kidney disease, diabetic kidney disease, chronic kidney disease, fibrotic diseases (including lung and kidney fibrosis), dilated cardiomyopathy, respiratory diseases (including chronic obstructive pulmonary disease (COPD) and acute lung injury), acute and chronic liver diseases (such as nonalcoholic steatohepatitis and alcoholic hepatitis).

Various assays for identifying a compound's ability to inhibit ASK1 kinase activity and its usefulness as an ASK1 inhibitor are known in the art and are described, for example, in U.S. Pat. No. 8,742,126.

Some embodiments described herein are directed to the use of a form of Compound I as described herein or a pharmaceutical composition as described herein in the treatment of a disease in a patient in need of treatment with an ASK1 inhibitor.

Some embodiments described herein are methods of treating diabetic nephropathy, or complications of diabetes, comprising administering a therapeutically effective amount of a form of Compound I as described herein or a pharmaceutical composition as described herein. In some embodiments, diabetes includes type 1 and type 2 diabetes, gestational diabetes, prediabetes, insulin resistance, metabolic syndrome, impaired fasting glycaemia and impaired glucose tolerance. Type 1 diabetes is also known as Insulin Dependent Diabetes Mellitus (IDDM). Type 2 is also known as Non-Insulin-Dependent Diabetes Mellitus (NIDDM).

Another embodiment is directed to the method of treating kidney disease, or diabetic kidney disease comprising administering a therapeutically effective amount of a form of Compound I as described herein or a pharmaceutical composition as described herein.

Another embodiment is directed to the method of treating kidney fibrosis, lung fibrosis, or idiopathic pulmonary fibrosis (IPF) comprising administering a therapeutically effective amount of a form of Compound I as described herein or a pharmaceutical composition as described herein.

Another embodiment is directed to the method of treating diabetic kidney disease, diabetic nephropathy, kidney fibrosis, liver fibrosis, or lung fibrosis comprising administering a therapeutically effective amount of a crystalline form of Compound I as described herein or a pharmaceutical composition as described herein.

Liver diseases are acute or chronic damages to the liver based in the duration of the disease. The liver damage may be caused by infection, injury, exposure to drugs or toxic compounds such as alcohol or impurities in foods, an abnormal build-up of normal substances in the blood, an autoimmune process, a genetic defect (such as haemochromatosis), or other unknown causes. Exemplary liver diseases include, but are not limited to, cirrhosis, liver fibrosis, non-alcoholic fatty liver disease (NAFLD), non-alcoholic steatohepatitis (NASH), hepatic ischemia reperfusion injury, primary biliary cirrhosis (PBC), and hepatitis, including both viral and alcoholic hepatitis.

Non-alcoholic fatty liver disease (NAFLD) is the build up of extra fat in liver cells that is not caused by alcohol. NAFLD may cause the liver to swell (i.e. steatohepatitis), which in turn may cause scarring (i.e. cirrhosis) over time and may lead to liver cancer or liver failure. NAFLD is characterized by the accumulation of fat in hepatocyes and is often associated with some aspects of metabolic syndrome (e.g. type 2 diabetes mellitus, insulin resistance, hyperlipidemia, hypertension). The frequency of this disease has become increasingly common due to consumption of carbohydrate-rich and high fat diets. A subset (~20%) of NAFLD patients develop nonalcoholic steatohepatitis (NASH).

NASH, a subtype of fatty liver disease, is the more severe form of NAFLD. It is characterized by macrovesicular steatosis, balloon degeneration of hepatocytes, and/or inflammation ultimately leading to hepatic scarring (i.e. fibrosis). Patients diagnosed with NASH progress to advanced stage liver fibrosis and eventually cirrhosis. The current treatment for cirrhotic NASH patients with end-stage disease is liver transplant.

A study has shown that a significant proportion of diagnosed NASH patients (39%) have not had a liver biopsy to confirm the diagnosis. A greater proportion of diagnosed NASH patients have metabolic syndrome parameters than what is reported in the literature (type-II diabetes mellitus 54%, Obesity 71%, metabolic syndrome 59%). 82% of physicians use a lower threshold value to define significant alcohol consumption compared with practice guideline recommendations. 88% of physicians prescribe some form of pharmacologic treatment for NASH (Vit E: prescribed to 53% of NASH patients, statins: 57%, metformin: 50%). Therefore, the vast majority of patients are prescribed medications despite a lack of a confirmed diagnosis or significant data to support the intervention and alcohol thresholds to exclude NASH are lower than expected.

Another common liver disease is primary sclerosing cholangitis (PSC). It is a chronic or long-term liver disease that slowly damages the bile ducts inside and outside the liver. In patients with PSC, bile accumulates in the liver due to blocked bile ducts, where it gradually damages liver cells and causes cirrhosis, or scarring of the liver. Currently, there is no effective treatment to cure PSC. Many patients having PSC ultimately need a liver transplant due to liver failure, typically about 10 years after being diagnosed with the disease. PSC may also lead to bile duct cancer.

Liver fibrosis is the excessive accumulation of extracellular matrix proteins, including collagen, that occurs in most types of chronic liver diseases. Advanced liver fibrosis results in cirrhosis, liver failure, and portal hypertension and often requires liver transplantation.

Disclosed herein is a method of treating and/or preventing liver disease in a patient in need thereof, comprising administering to the patient a therapeutically effective amount of a form of Compound I as described herein or a composition thereof, optionally in combination with a therapeutically effective amount of a LOXL2 inhibitor. The presence of active liver disease can be detected by the existence of elevated enzyme levels in the blood. Specifically, blood levels of alanine aminotransferase (ALT) and aspartate aminotransferase (AST), above clinically accepted normal ranges, are known to be indicative of on-going liver damage. Routine monitoring of liver disease patients for blood levels of ALT and AST is used clinically to measure progress of the liver disease while on medical treatment. Reduction of elevated ALT and AST to within the accepted normal range is taken as clinical evidence reflecting a reduction in the severity of the patients on-going liver damage.

In certain embodiments, the liver disease is a chronic liver disease. Chronic liver diseases involve the progressive destruction and regeneration of the liver parenchyma, leading to fibrosis and cirrhosis. In general, chronic liver diseases can be caused by viruses (such as hepatitis B, hepatitis C, cytomegalovirus (CMV), or Epstein Barr Virus (EBV)), toxic agents or drugs (such as alcohol, methotrexate, or nitrofurantoin), a metabolic disease (such as non-alcoholic fatty liver disease (NAFLD), non-alcoholic steatohepatitis (NASH), haemochromatosis, or Wilson's Disease), an autoimmune disease (such as Autoimmune Chronic Hepatitis, Primary Biliary Cirrhosis, or Primary Sclerosing Cholangitis), or other causes (such as right heart failure).

Some embodiments described herein are directed to a method of treating liver disease comprising administering a therapeutically effective amount of a form of Compound I as described herein or a pharmaceutical composition as described herein. Liver disease can be classified into 4 stages: F0 indicates no fibrosis; F1 indicates mild fibrosis; F2 indicates moderate fibrosis; F3 indicates severe fibrosis; and F4 indicates cirrhosis. Some embodiments described herein are directed to a method of treating Fibrosis Stage F2 or F3 comprising administering a therapeutically effective amount of a form of Compound I as described herein or a pharmaceutical composition as described herein.

In one embodiment, provided herein is a method for reducing the level of cirrhosis. In one embodiment, cirrhosis is characterized pathologically by loss of the normal microscopic lobular architecture, with fibrosis and nodular regeneration. Methods for measuring the extent of cirrhosis are well known in the art. In one embodiment, the level of cirrhosis is reduced by about 5% to about 100%. In one embodiment, the level of cirrhosis is reduced by at least about 5%, at least about 10%, at least about 15%, at least about 20%, at least about 25%, at least about 30%, at least about 35%, at least about 40%, at least about 45%, at least 50%, at least about 55%, at least about 60%, at least about 65%, at least about 70%, at least about 75%, at least about 80%, at least about 85%, at least about 90%, at least about 95%, or about 100% in the subject.

In certain embodiments, the liver disease is a metabolic liver disease. In one embodiment, the liver disease is non-alcoholic fatty liver disease (NAFLD). NAFLD is associated with insulin resistance and metabolic syndrome (obesity, combined hyperlipidemia, diabetes mellitus (type II) and high blood pressure). NAFLD is considered to cover a spectrum of disease activity, and begins as fatty accumulation in the liver (hepatic steatosis).

It has been shown that both obesity and insulin resistance probably play a strong role in the disease process of NAFLD. In addition to a poor diet, NAFLD has several other known causes. For example, NAFLD can be caused by certain medications, such as amiodarone, antiviral drugs (e.g., nucleoside analogues), aspirin (rarely as part of Reye's syndrome in children), corticosteroids, methotrexate, tamoxifen, or tetracycline. NAFLD has also been linked to the consumption of soft drinks through the presence of high fructose corn syrup which may cause increased deposition of fat in the abdomen, although the consumption of sucrose shows a similar effect (likely due to its breakdown into fructose). Genetics has also been known to play a role, as two genetic mutations for this susceptibility have been identified.

If left untreated, NAFLD can develop into non-alcoholic steatohepatitis (NASH), which is the most extreme form of NAFLD, a state in which steatosis is combined with inflammation and fibrosis. NASH is regarded as a major cause of cirrhosis of the liver of unknown cause. Accordingly, provided herein is a method of treating and/or preventing nonalcoholic steatohepatitis (NASH) in a patient in need thereof, comprising administering to the patient a therapeutically effective amount of form of Compound I as described herein or a composition thereof, optionally in combination with a therapeutically effective amount of a LOXL2 inhibitor.

Also provided herein is a method of treating and/or preventing liver fibrosis in a patient in need thereof, comprising administering to the patient a therapeutically effective amount of an form of Compound I as described herein or a composition thereof, optionally in combination with a therapeutically effective amount of a LOXL2 inhibitor. Liver fibrosis is the excessive accumulation of extracellular matrix proteins including collagen that occurs in most types of chronic liver diseases. In certain embodiments, advanced liver fibrosis results in cirrhosis and liver failure. Methods for measuring liver histologies, such as changes in the extent of fibrosis, lobular hepatitis, and periportal bridging necrosis, are well known in the art.

In one embodiment, the level of liver fibrosis, which is the formation of fibrous tissue, fibroid or fibrous degeneration, is reduced by more that about 90%. In one embodiment, the level of fibrosis, which is the formation of fibrous tissue, fibroid or fibrous degeneration, is reduced by at least about 90%, at least about 80%, at least about 70%, at least about 60%, at least about 50%, at least about 40%, at least about 30%, at least about 20%, at least about 10%, at least about 5% or at least about 2%.

In one embodiment, the compounds provided herein reduce the level of fibrogenesis in the liver. Liver fibrogenesis is the process leading to the deposition of an excess of extracellular matrix components in the liver known as fibrosis. It is observed in a number of conditions such as chronic viral hepatitis B and C, alcoholic liver disease, drug-induced liver disease, hemochromatosis, auto-immune hepatitis, Wilson disease, primary biliary cirrhosis, sclerosing cholangitis, liver schistosomiasis and others. In one embodiment, the level of fibrogenesis is reduced by more that about 90%. In one embodiment, the level of fibrogenesis is reduced by at least about 90%, at least about 80%, at least about 70%, at least about 60%, at least about 50%, at least about 40%, at least about 30%, at least about 20%, at least about 10%, at least about 5% or at least 2%.

In still other embodiments, provided herein is a method of treating and/or preventing primary sclerosing cholangitis (PSC) in a patient in need thereof, comprising administering to the patient a therapeutically effective amount of an form of Compound I as described herein or a composition thereof, optionally in combination with a therapeutically effective amount of a LOXL2 inhibitor.

A LOXL2 inhibitor for use in the methods and pharmaceutical compositions described herein may be any agent that is capable of inactivating lysyl oxidase-like 2 (LOXL2) protein. The agent may be a chemical compound or biological molecule (e.g., a protein or antibody). Such inhibitors are readily identified by known methods (see, e.g., U.S. Pat. No. 8,461,303, U.S. 2009/0053224 and U.S. 2011/0044907, which are hereby incorporated herein by reference in their entirety).

In certain embodiments, the LOXL2 inhibitor is an anti-LOXL2 antibody (see, e.g., U.S. Pat. No. 8,461,303, U.S. 2012/0309020, U.S. 2013/0324705, and U.S. 2014/0079707, which are incorporated herein by reference in their entirety). The anti-LOXL2 antibody can be a monoclonal antibody (including full length monoclonal antibody), polyclonal antibody, human antibody, humanized antibody, chimeric antibody, diabody, multispecific antibody (e.g., bispecific antibody), or an antibody fragment including, but not limited to, a single chain binding polypeptide, so long as it exhibits the desired biological activity.

In certain embodiments, the anti-LOXL2 antibody is a monoclonal anti-LOXL2 antibody, or antigen-binding fragment thereof. In other embodiments, the anti-LOXL2 antibody is a polyclonal anti-LOXL2 antibody, or antigen-binding fragment thereof. Such antibodies are known in the art or are available from commercial sources. In certain embodiments, the isolated antibody or antigen binding fragment is humanized.

In additional embodiments, the LOXL2 inhibitor is anti-LOXL2 antibody AB0023 having the heavy chain variable region comprising the amino acid sequence set forth in SEQ ID NO: 1 and the light chain variable region comprising the amino acid sequence set forth in SEQ ID NO: 2. The methods of generating AB0023 and other anti-LOXL2 antibodies are generally disclosed in the '303 patent. In certain embodiments, the isolated antibody or antigen binding fragment is humanized. In further additional embodiments, the LOXL2 inhibitor is an anti-LOXL2 antibody comprising the sequences having about 85%, 90%, 91%, 92%, 93%, 94%, 95%, 96%, 97%, 98% or 99% identity to SEQ ID NO: 1. In some additional embodiments, the LOXL2 inhibitor is an anti-LOXL2 antibody comprising the sequences having about 85%, 90%, 91%, 92%, 93%, 94%, 95%, 96%, 97%, 98% or 99% identity to SEQ ID NO: 2.

In some embodiments, the LOXL2 inhibitor may be orally administered in a pharmaceutically effective amount. For oral administration, each dosage unit can contain from 1 mg to 2 gram, 1 mg to 1 gram, or 1 mg to 500 mg of LOXL2 inhibitor. In some embodiments, the dose is from 1 mg to 250 mg or 1 mg to 350 mg of LOXL2 inhibitor. The dose of the LOXL2 inhibitor may be given as a single dose or divided doses two, three, four, five, or six times a day. It will be understood, however, that the amount of LOXL2 inhibitor actually administered usually will be determined by a physician in light of the relevant circumstances including the condition to be treated, the chosen route of administration, and co-administration compound and if applicable, the age, weight, response of the individual patient, the severity of the patient's symptoms, and the like.

Also provided herein is a method of treating liver disease in a patient in need thereof, comprising administering to the patient a therapeutically effective amount of form of Compound I as described herein or a composition thereof, optionally in combination with a therapeutically effective amount of a FXR agonist.

Also provided herein is a method of treating and/or preventing nonalcoholic steatohepatitis (NASH) in a patient in need thereof, comprising administering to the patient a therapeutically effective amount of form of Compound I as described herein or a composition thereof, optionally in combination with a therapeutically effective amount of a FXR agonist.

FXR is a member of the nuclear receptor superfamily. Pharmacological activation of Farnesoid X Receptor (FXR) can attack underlying causes of NAFLD and NASH. A FXR agonist for use in the methods and compositions described herein may be any agent that is capable of binding to FXR and activating FXR to produce a biological response. FXR agonists can include, but are not limited to: cholic acid; obeticholic acid, chenodeoxycholic acid, chenodeoxycholate, PX-102, PX-104, WAY-362450 (FXR-450 or XL335), oleanolic acid, and GW-4064. In some embodiments, the FXR agonist is a compound of formula:

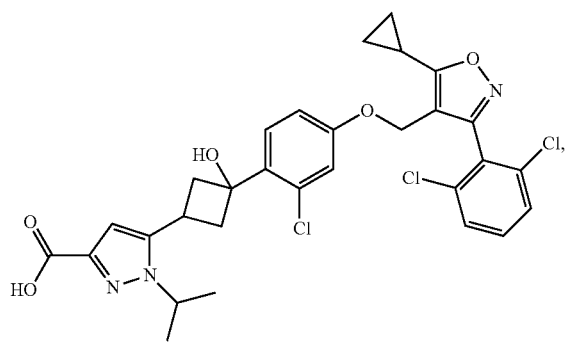 [SMILES: CC(C)n1nc(C(=O)O)cc1C1CC(O)(c2ccc(OCc3c(-c4c(Cl)cccc4Cl)noc3C3CC3)cc2Cl)C1]

or a salt, a stereoisomer or a mixture of stereoisomers thereof. In some embodiments, the FXR agonist is a compound of formula:

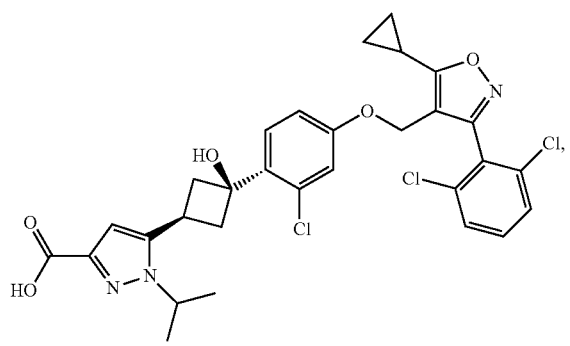

or a salt thereof.
Alternative FXR agonists are described in U.S. Pat. No. 9,139,539, which is hereby incorporated by reference in its entirety.

In some embodiments, the FXR agonist may be orally administered in a pharmaceutically effective amount. For oral administration, each dosage unit can contain from 1 mg to 2 gram, 1 mg to 1 gram, or 1 mg to 500 mg of FXR agonist. In some embodiments, the dose is from 1 mg to 250 mg or 1 mg to 350 mg of FXR agonist. The dose of the FXR agonist may be given as a single dose or divided doses two, three, four, five, or six times a day. It will be understood, however, that the amount of FXR agonist actually administered usually will be determined by a physician in light of the relevant circumstances including the condition to be treated, the chosen route of administration, and co-administration compound and if applicable, the age, weight, response of the individual patient, the severity of the patient's symptoms, and the like.

Also disclosed herein is a method of treating and/or preventing alcoholic liver disease in a patient in need thereof, comprising administering to the patient a therapeutically effective amount of a form of Compound I as described herein or a composition thereof, optionally in combination with a therapeutically effective amount of an additional therapeutic agent. In some embodiments, the alcoholic liver disease is alcoholic hepatitis. In some embodiments, the additional therapeutic agent is corticosteroids (including but not limited prednisolone and prednisone), pentoxifylline, or other agents with antioxidant effects (including not limited to N-acetylcysteine (NAC)). The additional therapeutic agent can be administered in dosages from 1 mg to 2 gram, 1 mg to 1 gram, or 1 mg to 500 mg and may be given as a single dose or divided doses two, three, four, five, or six times a day. It will be understood, however, that the amount of the additional therapeutic agent actually administered usually will be determined by a physician in light of the relevant circumstances including the condition to be treated, the chosen route of administration, and co-administration compound and if applicable, the age, weight, response of the individual patient, the severity of the patient's symptoms, and the like.

Inhibition of ASK1 with a form of Compound I and resultant reduction of oxidative stress-induced hepatocyte apoptosis and necrosis, both of which are key mediators of alcoholic liver disease pathogenesis, can improve efficacy and safety in patients with alcoholic liver disease. ASK1 inhibition is expected to reduce pathological hepatocyte apoptosis and necrosis, which correlate with alcoholic liver disease severity. Investigations in rodent models and histopathological studies in humans suggest that lipopolysaccharide (LPS)-induced inflammation and oxidative stress are key drivers of hepatocyte death in alcoholic hepatitis. Ethanol consumption increases intestinal permeability and bacterial translocation to the liver, resulting in LPS-induced hepatic inflammation. Subsequent hepatocellular injury occurs by neutrophil oxidative bursts, and Fas ligand and TNF-α induced hepatocyte apoptosis. In addition, ethanol strongly induces the expression of CYP2E1, which produces reactive oxygen species (ROS) as a by-product of ethanol metabolism, and reduces hepatic antioxidant capacity. Oxidative stress occurs as a result of these changes and directly induces hepatocyte mitochondrial dysfunction and necrosis and also sensitizes hepatocytes to apoptosis induced by TNF-α and FAS ligand [14].

ASK1 is activated by oxidative stress and induces the activation of p38 and JNK kinases, which promote mitochondrial dysfunction leading to apoptosis and necrosis. A potential role for ASK1 in alcoholic liver disease is supported by nonclinical studies demonstrating that oxidative stress, CYP2E1, Fas ligand and TNF-α signaling activate ASK1 in the mouse liver. In addition, Ask1$^{-/-}$ mice are resistant to acute liver injury caused by Fas activation, TNF-α (induced by LPS plus Dgalactosamine), bile duct ligation, or acetaminophen overdose. Moreover, pharmacological inhibition of ASK1 in mice reduces hepatocellular injury and necrosis induced by acetaminophen overdose, as well as cardiac and renal apoptosis and necrosis induced by acute ischemia/reperfusion injury. These effects correlated with reduced activation/phosphorylation of ASK1, p38, and JNK, and reduced mitochondrial dysfunction.

It has been found that ASK1 inhibition does not directly reduce LPS-mediated signaling and cytokine release by macrophages, nor does it reduce oxidative burst by neutrophils. These pathways are considered important mechanisms in the pathophysiology of severe alcoholic hepatitis. Prednisolone is the standard of care for severe alcoholic hepatitis and has been shown to reduce systemic levels of cytokines (i.e. TNF-α, IL-8) and reduce neutrophil activity (oxidative burst) in patients with severe alcoholic hepatitis. The complementary mechanisms of action of a form of Compound I and prednisolone, as well as other therapeutic agents known to be useful for alcoholic hepatitis, suggest a potential benefit could be gained via their combination.

It also has been found that hepatic expression of phospho-p38 (p-p38), a downstream marker of ASK1 activation, are elevated in patients with alcoholic hepatitis. This suggests that treatment with a form of Compound I may benefit patients with alcoholic liver disease.

Mortality due to alcoholic hepatitis is associated with acute loss of liver function and accompanying complications of advanced liver disease, including encephalopathy, sepsis, and/or multiple organ failure, including renal failure. It is believed that the hepatoprotective effects of Compound I can translate into improved liver function and resultant improved mortality in patients with alcoholic liver disease. Early improvement in liver function is associated with better survival (e.g. 1-6 months following presentation). It is not anticipated that ASK1 inhibition will directly ameliorate secondary complications such as those driven by end-stage hemodynamic changes or sepsis.

Also provided herein are methods of treating a disease or condition causally related or attributable to aberrant activity of JAK, and in particular, conditions related to aberrant activity of JAK1 and/or JAK2, by administering a therapeutically effective amount of a form of Compound I as described herein and a therapeutically effective amount filgotinib. In still other embodiments, provided herein is a method of treating a disease or condition causally related or attributable to aberrant activity of JAK, and in particular, conditions related to aberrant activity of JAK1 and/or JAK2, by administering a therapeutically effective amount of pharmaceutical composition comprising a form of Compound I and filgotinib. In some embodiments, the pharmaceutical composition comprising a form of Compound I and filgotinib may be orally administered. In some embodiments, the pharmaceutical composition comprising a form of Compound I and filgotinib is a tablet. Accordingly, the disclosed method includes preventing and/or treating inflammatory conditions, autoimmune diseases, proliferative diseases, transplantation rejection, diseases involving impairment of cartilage turnover, congenital cartilage malformations, and diseases associated with hypersecretion of IL6 in mammals including humans. It is contemplated that a combination of a form of Compound I and filgotinib can produce a synergistic effect. Filgotinib is described in U.S. Pat. No. 8,563, 545.

Also provided, in one embodiment, are methods of treating a mammal susceptible to or afflicted with an inflammatory condition by administration of a therapeutically effective amount of a form of Compound I as described herein and a therapeutically effective amount filgotinib or a therapeutically effective amount of pharmaceutical composition comprising a form of Compound I and filgotinib. In a specific embodiment, the inflammatory condition is selected from rheumatoid arthritis, osteoarthritis, allergic airway disease (e.g. asthma) and inflammatory bowel diseases.

In one embodiment, the disease or condition to be treated by administration of a therapeutically effective amount of a form of Compound I as described herein and a therapeutically effective amount filgotinib or a therapeutically effective amount of pharmaceutical composition comprising a form of Compound I and filgotinib is an autoimmune disease. In a specific embodiment, the autoimmune disease is selected from COPD, asthma, systemic lupus erythematosis, type I diabetes mellitus and inflammatory bowel disease.

In one embodiment, the disease or condition to be treated by administration of a therapeutically effective amount of a form of Compound I as described herein and a therapeutically effective amount filgotinib or a therapeutically effective amount of pharmaceutical composition comprising a form of Compound I and filgotinib is a proliferative disease, in particular cancer (e.g. solid tumors such as uterine leiomyosarcoma or prostate cancer), leukemia (e.g. AML or ALL), multiple myeloma and/or psoriasis.

In one embodiment, the disease or condition to be treated by administration of a therapeutically effective amount of a form of Compound I as described herein and a therapeutically effective amount filgotinib or a therapeutically effective amount of pharmaceutical composition comprising a form of Compound I and filgotinib is transplantation rejection, such as organ transplant rejection.

In one embodiment, the disease or condition to be treated by administration of a therapeutically effective amount of a form of Compound I as described herein and a therapeutically effective amount filgotinib or a therapeutically effective amount of pharmaceutical composition comprising a form of Compound I and filgotinib is a disease involving impairment of cartilage turnover.

In one embodiment, the disease or condition to be treated by administration of a therapeutically effective amount of a form of Compound I as described herein and a therapeutically effective amount filgotinib or a therapeutically effective amount of pharmaceutical composition comprising a form of Compound I and filgotinib is congenital cartilage malformation.

In one embodiment, the disease or condition to be treated by administration of a therapeutically effective amount of a form of Compound I as described herein and a therapeutically effective amount filgotinib or a therapeutically effective amount of pharmaceutical composition comprising a form of Compound I and filgotinib is a disease associated with hypersecretion of IL6, in particular Castleman's disease or mesangial proliferative glomerulonephritis.

In some embodiments, filgotinib may be orally administered in a pharmaceutically effective amount. For oral administration, each dosage unit can contain from 1 mg to 2 gram, 1 mg to 1 gram, or 1 mg to 500 mg of filgotinib. In some embodiments, the dose is from 1 mg to 250 mg of filgotinib. In some embodiments, a dose of filgotinib ranges from about 20 mg twice a day to about 50 mg twice a day. In some embodiments, the dose is 2 mg, 4 mg, 6 mg, 8 mg, 10 mg, 12 mg, 14 mg, 16 mg, 18 mg, 20 mg, 25 mg, 30 mg, 35 mg, 40 mg, 45 mg, 50 mg, 75 mg, 100 mg, 200 mg, or 500 mg of filgotinib. It will be understood, however, that the amount of filgotinib actually administered usually will be determined by a physician in light of the relevant circumstances including the condition to be treated, the chosen route of administration, and co-administration compound and if applicable, the age, weight, response of the individual patient, the severity of the patient's symptoms, and the like.

In some embodiments, filgotinib may be administered to achieve injection dose levels that range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as degenerative conditions, the regimen for treatment usually stretches over many months or years so oral dosing is preferred for patient convenience and tolerance. With oral dosing of filgotinib, one to five and especially two to four and typically three oral doses per day are representative regimens. Using these dosing patterns, each dose provides from about 0.01 to about 20 mg/kg of the compound of the invention, with particular doses each providing from about 0.1 to about 10 mg/kg and especially about 1 to about 5 mg/kg.

Transdermal doses of filgotinib are generally selected to provide similar or lower blood levels than are achieved using injection doses.

When used to prevent the onset of an inflammatory condition, filgotinib may be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The forms of Compound I disclosed herein, optionally in combination with filgotinib, are useful for the treatment of diseases or conditions that include, without limitation, cancer, diabetes, and inflammatory diseases such as rheumatoid arthritis (RA), multiple sclerosis (MS), inflammatory bowel disease (IBD), sepsis, psoriasis, misregulated TNF expression and graft rejection. The forms of Compound I disclosed herein are useful for alleviating a symptom of diseases or conditions that include, without limitation, cancer, diabetes, and inflammatory diseases such as rheumatoid arthritis (RA), multiple sclerosis (MS), inflammatory bowel disease (IBD), sepsis, psoriasis, misregulated TNF expression and graft rejection. In some embodiments, the methods include identifying a mammal having a symptom of the disease or disorder and providing to the mammal an amount of a form of Compound I as described herein effective to ameliorate (i.e., lessen the severity of) the symptom).

In some embodiments, the forms of Compound I disclosed herein, optionally in combination with filgotinib, are useful for the treatment of a solid tumor. In particular embodiments, the solid tumor is from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors (e.g., glioma, anaplastic oligodendroglioma, adult glioblastoma multiforme, and adult anaplastic astrocytoma), bone cancer, or soft tissue sarcoma. In some embodiments, the solid tumor is from non-small cell lung cancer, small-cell lung cancer, colon cancer, CNS cancer, melanoma, ovarian cancer, renal cancer, prostate cancer, or breast cancer.

In some embodiments, the forms of Compound I disclosed herein, optionally in combination with filgotinib, are useful for the treatment of diabetes, which includes any metabolic disorder characterized by impaired insulin production and glucose tolerance. In some embodiments, diabetes includes type 1 and type 2 diabetes, gestational diabetes, prediabetes, insulin resistance, metabolic syndrome, impaired fasting glycaemia and impaired glucose tolerance. Type 1 diabetes is also known as Insulin Dependent Diabetes Mellitus (IDDM). Type 2 is also known as Non-Insulin-Dependent Diabetes Mellitus (NIDDM).

In some embodiments, the forms of Compound I disclosed herein, optionally in combination with filgotinib, are useful for the treatment of an inflammatory disease or LPS induced endotoxin shock. In some embodiments, the disease is an autoimmune disease. In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), inflammatory bowel disease (IBD), sepsis, psoriasis, Sjoegren's syndrome, psoriasis, autoimmune hemolytic anemia, asthma, or chronic obstructive pulmonary disease (COPD). In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

Some embodiments described herein are methods of treating inflammatory bowel disease (IBD), comprising administering a therapeutically effective amount of a form of Compound I as described herein or a pharmaceutical composition as described herein, optionally in combination with filgotinib. The term "inflammatory bowel disease" or "IBD" as used herein is a collective term describing inflammatory disorders of the gastrointestinal tract, the most common forms of which are ulcerative colitis and Crohn's disease. Other forms of IBD that can be treated with the presently disclosed compounds, compositions and methods include diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behcet's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, and chronic diarrhea.

Treating or preventing IBD also includes ameliorating or reducing one or more symptoms of IBD. As used herein, the term "symptoms of IBD" refers to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding). The term "wherein said symptoms are reduced" refers to a qualitative or quantitative reduction in detectable symptoms, including but not limited to a detectable impact on the rate of recovery from disease (e.g. rate of weight gain). The diagnosis is typically determined by way of an endoscopic observation of the mucosa, and pathologic examination of endoscopic biopsy specimens.

The course of IBD varies, and is often associated with intermittent periods of disease remission and disease exacerbation. Various methods have been described for characterizing disease activity and severity of IBD as well as response to treatment in subjects having IBD. Treatment according to the present methods are generally applicable to a subject having IBD of any level or degree of disease activity.

Criteria useful for assessment of disease activity in subjects with ulcerative colitis can be found in, e.g., Truelove et al. (1955) Br Med J 2:1041-1048.) Using these criteria, disease activity can be characterized in a subject having IBD as mild disease activity or severe disease activity. Subjects who do not meet all the criteria for severe disease activity, and who exceed the criteria for mild disease activity are classified as having moderate disease activity.

The presently disclosed treatment methods can also be applied at any point in the course of the disease. In certain embodiments, the methods are applied to a subject having IBD during a time period of remission (i.e., inactive disease). In such embodiments, the present methods provide benefit by extending the time period of remission (e.g., extending the period of inactive disease) or by preventing, reducing, or delaying the onset of active disease. In other embodiments, methods may be applied to a subject having IBD during a period of active disease. Such methods provide benefit by reducing the duration of the period of active disease, reducing or ameliorating one or more symptoms of IBD, or treating IBD.

Measures for determining efficacy of treatment of IBD in clinical practice have been described and include, for example, the following: symptom control; fistula closure; extent of corticosteroid therapy required; and, improvement in quality of life. Heath-related quality of life (HRQL) can be assessed using the Inflammatory Bowel Disease Questionnaire (IBDQ), which is extensively used in clinical practice to assess quality of life in a subject with IBD. (See Guyatt et al. (1989) Gastroenterology 96:804-810.) Improvements in any of the foregoing response criteria are specifically provided by the methods of the present disclosure.

Some embodiments described herein are directed to methods of treating pulmonary hypertension in a patient in need thereof, said method comprising administering to the patient a therapeutically effective amount of a form of Compound I as described herein or a pharmaceutical composition as described herein.

The pulmonary hypertension condition treated by the methods of the disclosure can comprise any one or more of the conditions recognized according to the World Health Organization (WHO) or Venice (2003) classification (see, for example, Rubin (2004) *Chest* 126:7-10):

Group 1: Pulmonary Arterial Hypertension (PAH)
  1.1 idiopathic PAH
  1.2 familial PAH
  1.3 PAH associated with:
    1.3.1 collagen vascular disease
    1.3.2 congenital systemic-to-pulmonary shunts (including Eisenmenger's syndrome)
    1.3.3 portal hypertension
    1.3.4 HIV infection
    1.3.5 drugs and toxins
    1.3.6 other (thyroid disorders, glycogen storage disease, Gaucher disease, hereditary hemorrhagic telangiectasia, hemoglobinopathies, myeloproliferative disorders, splenectomy)
  1.4 PAH associated with significant venous or capillary involvement
    1.4.1 pulmonary veno-occlusive disease (PVOD)
    1.4.2 pulmonary capillary hemangiomatosis (PCH)
  1.5 persistent pulmonary hypertension of the newborn Group 2: Pulmonary Hypertension with Left Heart Disease
  2.1 left-sided atrial or ventricular heart disease
  2.2 left-sided valvular heart disease Group 3: Pulmonary Hypertension Associated with Lung Diseases and/or Hypoxemia
  3.1 chronic obstructive pulmonary disease (COPD)
  3.2 interstitial lung disease
  3.3 sleep-disordered breathing
  3.4 alveolar hypoventilation disorders
  3.5 chronic exposure to high altitude
  3.6 developmental abnormalities Group 4: Pulmonary Hypertension due to Chronic Thrombotic and/or Embolic Disease
  4.1 thromboembolic obstruction of proximal pulmonary arteries
  4.2 thromboembolic obstruction of distal pulmonary arteries
  4.3 non-thrombotic pulmonary embolism (tumor, parasites, foreign material)

Group 5: Miscellaneous (Sarcoidosis, Histiocytosis X, Lymphangiomatosis, Compression of Pulmonary Vessels (Adenopathy, Tumor, Fibrosing Mediastinitis))

In some embodiments, the pulmonary hypertension is pulmonary arterial hypertension. The pulmonary arterial hypertension, in one aspect, may be selected from idiopathic PAH, familial PAH, pulmonary veno-occlusive disease (PVOD), pulmonary capillary hemangiomatosis (PCH), persistent pulmonary hypertension of the newborn, or PAH associated with another disease or condition.

Combination Therapy

Patients being treated for cardio-renal diseases such as chronic kidney disease may benefit from combination drug treatment. For example the compound of the present invention may be combined with one or more of angiotensin converting enzyme (ACE) inhibitors such as enalapril, captopril, ramipril, lisinopril, and quinapril; or angiotensin II receptor blockers (ARBs) such as losartan, olmesartan, and irbesartan; or antihypertensive agents such as amlodipine, nifedipine, and felodipine. The benefit of combination may be increased efficacy and/or reduced side effects for a component as the dose of that component may be adjusted down to reduce its side effects while benefiting from its efficacy augmented by the efficacy of Compound I and/or other active component(s).

Patients presenting with chronic kidney disease treatable with ASK1 inhibitors such as Compound I may also exhibit conditions that benefit from co-administration (as directed by a qualified caregiver) of a therapeutic agent or agents that are antibiotic, analgesic, antidepressant and/or anti-anxiety agents in combination with Compound I. Combination treatments may be administered simultaneously or one after the other within intervals as directed by a qualified caregiver or via a fixed dose (all active ingredients are combined into the a single dosage form e.g. tablet) presentation of two or more active agents.

Coronary patients being treated for an acute cardiovascular disease event by administration of ASK1 inhibitors often exhibit diseases or conditions that benefit from treatment with other therapeutic agents. These diseases or conditions can be of the cardiovascular nature or can be related to pulmonary disorders, metabolic disorders, gastrointestinal disorders and the like. Additionally, some coronary patients being treated for an acute cardiovascular disease event by administration of an ASK1 inhibitor exhibit conditions that can benefit from treatment with therapeutic agents that are antibiotics, analgesics, and/or antidepressants and anti-anxiety agents.

Cardiovascular related diseases or conditions that can benefit from a combination treatment of ASK1 inhibitors with other therapeutic agents include, without limitation, angina, including stable angina, unstable angina (UA), exercised-induced angina, variant angina, arrhythmias, intermittent claudication, myocardial infarction including non-STE myocardial infarction (NSTEMI), heart failure including congestive (or chronic) heart failure, acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of ASK1 inhibitors with therapeutic agents suitable for treating cardiovascular related conditions allows enhancement in the standard of care therapy the patient is currently receiving.

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (Inspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotics inhibit the clotting ability of the blood. There are three main types of antithrombotics—platelet inhibitors, anticoagulants, and thrombolytic agents. Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein 11b/111a inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic agents are used to treat disorders of the heart rate and rhythm. Examples of antiarrhythmic agents include amiodarone, quinidine, procainamide, lidocaine, and propafenone. Cardiac glycosides and beta blockers are also used as antiarrhythmic agents.

Antihypertensive agents are used to treat hypertension, a condition in which the blood pressure is consistently higher than normal. Hypertension is associated with many aspects of cardiovascular disease, including congestive heart failure, atherosclerosis, and clot formation.

Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (Ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

In this disclosure, a subject in need of the ASK1 inhibitor often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient the compounds of the invention in combination with at least one therapeutic agent.

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostol (Cytotec); sucralfate; and antacids.

In one embodiment, a form of Compound I disclosed herein may be used in combination with one or more additional therapeutic agent that are being used and/or developed to treat gastrointestinal disorders. In one embodiment, a form of Compound I disclosed herein may be used in combination with one or more additional therapeutic agent that are being used and/or developed to treat inflammatory disorders (e.g., IBD). In such embodiments, the one or more additional therapeutic agent may be a α4β7 inhibitor, a steroid, a MMP-9 antibody, a S1P1 agonist, a TNF biologic, or any combination thereof.

In some embodiments, the one or more additional therapeutic agent may be a α4β7 integrin inhibitor, or an agent that inhibits the expression and/or activity of α4β7 integrin. The inhibitor can be small molecule or biologic. For example, the α4β7 integrin inhibitor can be natalizumab or vedolizumab.

In some embodiments, the one or more additional therapeutic agent may be a steroid, including but not limited to, corticosteroids. Corticosteroids may be administered by various routes, including intravenously (i.e., methylprednisolone, hydrocortisone), orally (i.e., prednisone, prednisolone, budesonide, dexamethasone), or topically (i.e., enema, suppository, or foam preparations).

In some embodiments, the one or more additional therapeutic agent may be an MMP9 inhibitor, or an agent that inhibits the expression and/or activity of MMP9. A representative protein sequence for MMP9 is GenBank Accession No. NP_004985. The inhibitor can be small molecule or biologic. For instance, Gu et al., *The Journal of Neuroscience,* 25(27): 6401-6408 (2005) discloses a specific MMP9 inhibitor, SB-3CT (CAS 292605-14-2). Further, siRNA, antisense RNA and antibodies have also been demonstrated to inhibit the expression or activity of MMP9 and are within the scope of the present disclosure. In one embodiment, an MMP9 inhibitor is a monoclonal anti-MMP9 antibody. In some embodiment, the one or more additional therapeutic agent includes an MMP9 inhibitor and a nucleoside analog such as gemcitabine.

In some embodiments, the one or more additional therapeutic agent may be a Sphingosine 1-Phosphate Receptor (S1P1) inhibitor, or an agent that inhibits the expression and/or activity of S1P1. The inhibitor can be small molecule or biologic. For example, the S1P1 inhibitor can be RPC1063.

In some embodiments, the one or more additional therapeutic agent may be a TNF inhibitor, or an agent that inhibits the expression and/or activity of TNF. The inhibitor can be small molecule or biologic. For example, the TNF inhibitor can be golimumab.

In some embodiments, the one or more additional therapeutic agent is being used and/or developed to treat ulcerative colitis (UC) and/or Crohn disease (CD). The agent can be a biologic or small molecule. In some embodiments, the agent is a modulator (e.g., agonist or antagonist) of S1P1, IL-6, CX3CL1, DHODH, α4, β7, JAK, TNF, CB, IL-12/IL-23, CCL20, TLR9, MAdCAM, CCR9, CXCL10, Smad7, PDE4, MC, VLA-1, GC, GATA-3, Eotaxin, FFA2, LIGHT, FMS, MMP9, CD40, Steroid, 5-ASA, Immunomod, STAT3, and/or EP4. In some embodiments, the JAK inhibitor is filgotinib.

Non-limiting examples of agents being used and/or developed to treat ulcerative colitis (UC) include GSK3050002 (CCL20 modulator, by GSK), GS-5745 (MMP9 modulator, by Gilead), AVX-470 (TNF modulator, by Avaxia), Bertilimumab (Eotaxin modulator, by Immune Pharma), Simponi (TNF modulator, by Johnson & Johnson and Merck), RX-10001 (by Resolvyx), IBD-98 (5-ASA modulator, by Holy Stone), SP-333 (GC modulator, by Synergy), KAG-308 (EP4 modulator, by Kaken), SB012 (GATA-3 modulator, by Sterna), AJM300 (α4 modulator, by Ajinomoto), BL-7040 (TLR9 modulator, by BiolineRx), TAK-114 (SAT3 modulator, by Takeda), CyCol (by Sigmoid), GWP-42003 (CB modulator, by GW Pharma), ASP3291 (MC modulator, by Drais), GLPG0974 (FFA2 modulator, by Galapagos), Ozanimod (S1P1 modulator, by Receptos), ASP015K (JAK modulator, by Astellas), Apremilast (PDE4 modulator, by Celgene), Zoenasa (by Altheus), Kappaproct (TLR9 modulator, by InDex), Phosphatidylcholine (by Dr Falk/Lipid Tx), Tofacitinib (JAk modulator, by Pfizer), Cortment (Steroid modulator, by Ferring), Uceris (Steroid modulator, by Salix), and 5-ASA modulators such as Delzicol (by Actavis), Canasa (by Aptalis), Asacol (by Actavis), Pentasa (by Shire/Ferring), Lialda (by Shire), Mezavant (by Shire), Apriso (by Salix), Colazal (by Salix), Giazo (by Salix), and Salofalk (by Dr Falk). Non-limiting examples of agents being used and/or developed to treat Crohn disease (CD) include FFP102 (CD40 modulator, by Fast Forward), E6011 (CX3CL1 modulator, by Eisai), PF-06480605 (by Pfizer), QBECO SSI (Immunomod modulator, by Qu Biologics), PDA-001 (by Celgene), BI 655066 (IL-12/IL-23 modulator, by Boehringer), TNFα kinoid (TNF modulator, by Neovacs), AMG 139/MEDI-2070 (IL-12/IL-23 modulator, by AstraZeneca), PF-04236921 (IL-6 modulator, by Pfizer), Tysabri (β7 modulator, marketed by Biogen Idec in the U.S.), Cimzia (marketed by UCB in the U.S.), JNJ-40346527 (FMS modulator, by J&J), SGX-203 (Steroid modulator, by Solgenix), CyCron (by Sigmoid), CCX507 (CCR9 modulator, by ChemoCentryx), MT1303 (S1P1 modulator, by Mitsubishi), 6-MP (by Teva), ABT-494 (JAk modulator, by Abbvie), Tofacitinib (JAk modulator, by Pfizer), TRK-170 (β7 modulator, by Toray), Mongersen (Smad7 modulator, by Celgene), RHB-104 (by Redhill), Rifaxmin EIR (by Salix), Budenofalk (by Dr Falk), and Entocort (by AstraZeneca).

Non-limiting examples of agents being used and/or developed to treat ulcerative colitis (UC) and Crohn disease (CD) include PF-06410293 (by Pfizer), SAN-300 (VLA-1 modulator, by Salix), SAR252067 (LIGHT modulator, by Sanofi), PF-00547659 (MAdCAM modulator, by Pfizer), Eldelumab (Smad7 modulator, by BMS), AMG 181/MEDI-7183 (β7 modulator, by Amgen/AstraZeneca), Etrolizumab (β7 modulator, by Roche), Ustekinumab (IL-12/IL-23 modulator, by J&J), Remicade (TNF modulator, by J&J and Merck), Entyvio (β7 modulator, by Takeda), Humira (TNF modulator, by Abbvie), Infliximab (by Celtrion), PF-06651600 (by Pfizer), GSK2982772 (by GSK), GLPG1205 (FFA2 modulator, by Galapagos), AG014 (by Intrexon) and Vidofludimus (DHODH modulator, by 4SC).

In some embodiments, the one or more additional therapeutic agent may be a JAK inhibitor, particularly a JAK-1 selective inhibitor. The inhibitor can be small molecule or biologic. For example, the JAK inhibitor can be Filgotinib, GLPG0634 (JAK modulator, by Galapagos).

Patients presenting with an acute coronary disease event may exhibit conditions that benefit from administration of therapeutic agent or agents that are antibiotics, analgesics, antidepressant and anti-anxiety agents in combination with ranolazine.

Antibiotics are therapeutic agents that kill, or stop the growth of, microorganisms, including both bacteria and fungi. Example of antibiotic agents include β-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics are therapeutic agents that are used to relieve pain. Examples of analgesics include opiates and morphinomimetics, such as fentanyl and morphine; paracetamol; NSAIDs, and COX-2 inhibitors.

Antidepressant and anti-anxiety agents include those agents used to treat anxiety disorders, depression, and those used as sedatives and tranquillers. Examples of antidepressant and anti-anxiety agents include benzodiazepines, such as diazepam, lorazepam, and midazolam; enzodiazepines; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban).

EXAMPLES

Crystalline forms of Compound I were analyzed by XRPD, DSC and TGA. XRPD patterns of Compound I were collected with a PANalytical X'Pert PRO MPD diffractometer using mostly the following experimental setting: 45 kV, 40 mA, Kα1=1.5406 Å, scan range 2-40° 2θ, step size 0.0167° 2θ. The DSC analysis was conducted on a TA Instruments Q2000 differential scanning calorimeter using 2-3 mg of material, 10° C./min heating rate over the range of (−30° C.)-300° C. The TGA data were obtained on TA Instruments 2950 and Q5000 thermogravimetric analyzers using 2-5 mg of material, 10° C./min heating rate over the range of 25-350° C.

1.1 Compound I Form I

Compound I Form I is an anhydrous form of Compound I, and it is contemplated to be the most thermodynamically stable polymorph of Compound I obtained from most organic solvents/solvent mixtures except for DCM and aqueous mixtures at greater than 0.6 water activity at ambient conditions.

Figure 2:
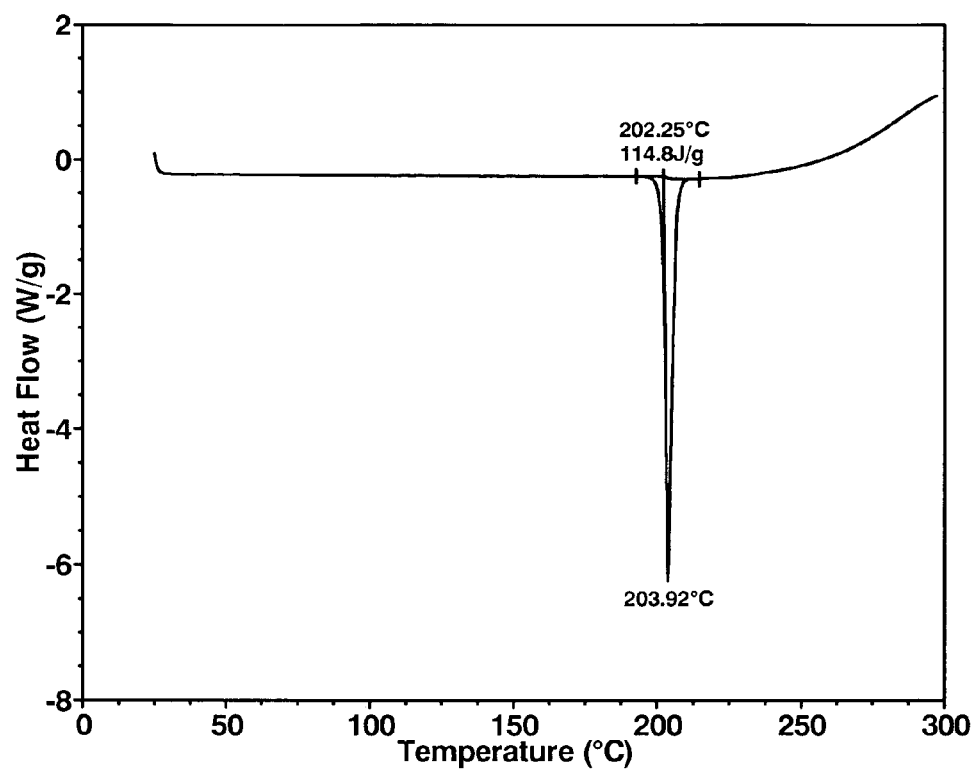
FIG. 2 shows a differential scanning calorimeter (DSC) curve of Compound I Form I.
Figure 3:
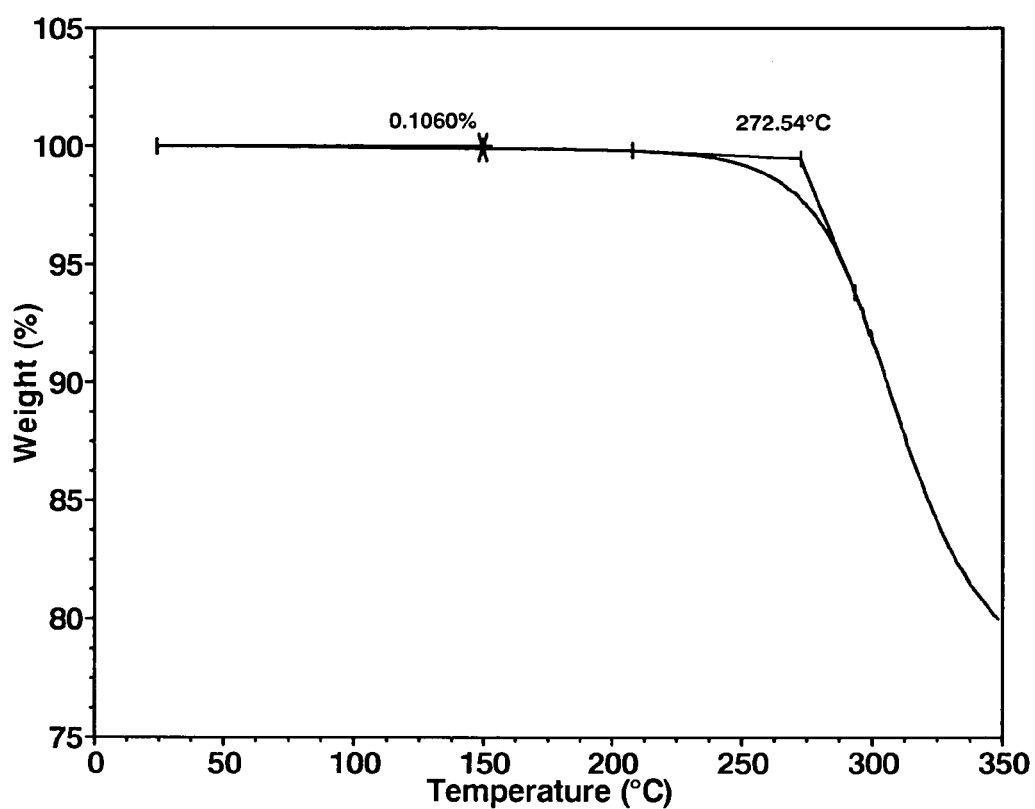
FIG. 3 shows a thermogravimetric analysis (TGA) of Compound I Form I.

Compound I Form I is crystalline by XRPD (FIG. 1) and can be characterized by an X-ray powder diffractogram comprising the following peaks: 8.9, 10.0, 13.9, 16.7, 21.3, 22.8, and 29.0° 2θ±0.2° 2θ. Table 1 summarizes the Single Crystal Data for Compound I Form I. Compound I Form I displays a melting onset temperature of about 202° C. based on DSC (FIG. 2). TGA analysis shows about 0.1% weight loss below 150° C. corresponding to the loss of residual solvents (FIG. 3).

Initially, Compound I Form I was isolated using the following procedure:

5-(4-Cyclopropyl-1H-imidazol-1-yl)-2-fluoro-4-methylbenzoic acid hydrochloride (30 g, 102 mmol) was suspended in anhydrous 1,2-dichloromethane (900 mL) at room temperature. Oxalyl chloride (18 ml, 205 mmol) was added while stirring under nitrogen, followed by N,N-dimethylformamide (0.783 ml, 10.2 mmol). The mixture was stirred for about 4 hr at room temperature, and then the solvent was removed under reduced pressure. The residue was dissolved in about 600 mL anhydrous dichloromethane. 6-(4-Isopropyl-4H-1,2,4-triazol-3-yl)pyridin-2-amine (22.9 g, 113 mmol) and 4-dimethylaminopyridine (12.5 g, 102 mmol) were rapidly added with stirring under nitrogen. The reaction was stirred for about 2 hours at room temperature and the dichloromethane was evaporated. The residue was dissolved in 500 mL water and solid NaHCO$_3$ was added until the pH of the mixture was about 7. Dichloromethane was added (about 500 mL) and the layers were separated. The aqueous layer was extracted with dichloromethane (2×300 mL). The combined organics were washed with water (2×200 mL), dried over MgSO$_4$, filtered and concentrated. The residue was dissolved in a minimum amount of THF, and water was added slowly until a thick slurry was formed. The solids were collected by filtration, washed with water, and dried.

The solids obtained (about 72 g) were recrystallized from hot EtOH (5 ml/g solid) and the solids collected by filtration, washed with 2:1 diethyl ether/EtOH, followed by diethyl ether and dried.

TABLE 1

Single Crystal Data for Compound I Form I

| Type | Formula | Space Group | Distance (Å) | | | Angle (°) | | |
| --- | --- | --- | --- | --- | --- | --- | --- | --- |
| | | | a | b | c | α | β | γ |
| anhydrous | C$_{25}$H$_{24}$FN$_7$O | P-1 | 9.7677 | 11.1043 | 11.5183 | 103.023 | 104.719 | 107.755 |

Compound I Form I can be isolated from a variety of solvent systems including (but not limited to): MeOH/water, MeOH/MTBE, iPrOAc/n-heptane, MTBE/n-heptane, and EtOH/n-heptane. The following two exemplary methods can be suitable for isolating Compound I Form I.

Method 1:

Solution of Compound I in DCM is solvent exchanged to EtOH (about 3 mL/g with respect to input Compound I) and heated to about 50° C.

Heptane (about 6.7 mL/g with respect to input Compound I) is added over about 1 h, and the resulting slurry is aged at about 50° C. for about 1 h The slurry is cooled to about 0° C. at about 10° C./h and aged at about 0° C. for about overnight The slurry is filtered and the wet cake is rinsed with 2 mL/g (with respect to g input Compound I) 1:2 v/v EtOH/heptane The isolated material is dried in a vacuum oven at about 45° C. to obtain Compound I Form I.

Method 2:

Due to the low solubility of Compound I in EtOH (about 20 mg/mL), a slurry of Compound I Form I is typically formed after performing the solvent exchange as outlined above. Solubility studies of Compound I in DCM/EtOH mixtures at elevated temperature were performed to determine the solubility range in the solvent swap that would accommodate seeding. The process outlined below was developed using this data aiming at about 10-20% v/v DCM remaining at the time of seeding. The crystallization was then continued in line with Method 1 outlined above. After filtration, the Form I solids are dried in a vacuum oven at about 45-50° C. The following steps can be performed to isolate Compound I Form I:

Final organic solution of Compound I in DCM is partially solvent exchanged to about 7.5 mL/g 20% v/v DCM/EtOH (with respect to input g Compound I) and the solution is seeded at about 50° C. with about 0.5 wt/wt % Compound I Form I and a seed bed is allowed to form over about 0.5 h Distillation is continued to provide about 3.3 mL/g total reactor volume of primarily EtOH as solvent Heptane (about 6.7 mL/g with respect to input g Compound I) is added over about 2 h, and the slurry is aged at about 50° C. for about 0.5 h The slurry is cooled to about 20° C. over about 1 h and aged at about 20° C. for about 0.5 h The slurry is filtered and the wet cake is rinsed with 2 mL/g (with respect to input g Compound I) 1:2 v/v EtOH/Heptane The isolated material is dried in a vacuum oven at about 45° C. to obtain Compound I Form I.

1.2 Compound I Form II and Compound I Form V

Compound I Form II was discovered during isolation of Compound I from DCM/n-heptane. Experimental XRPD showed that Form V is a labile solvate and the XRPD was not phase-pure. Air-drying at RT showed Form V converting to Form II and the presence of at least one intermediate form. Form V has only been truly isolated by growth of single crystals.

Figure 4:
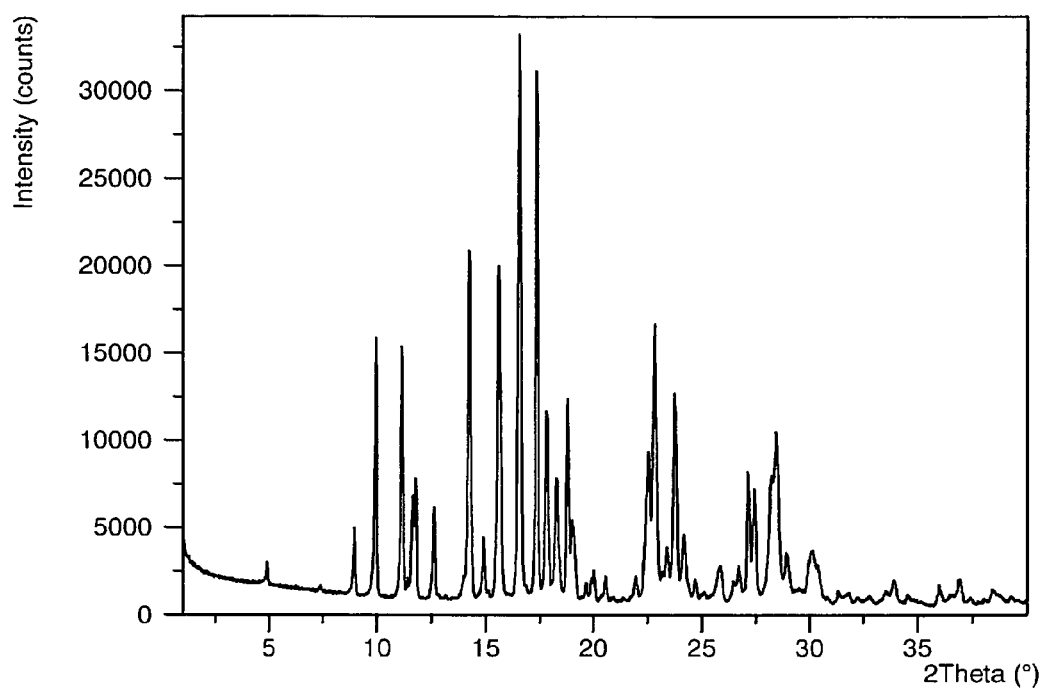
FIG. 4 shows an X-ray powder diffraction (XRPD) of Compound I Form II.
Figure 5:
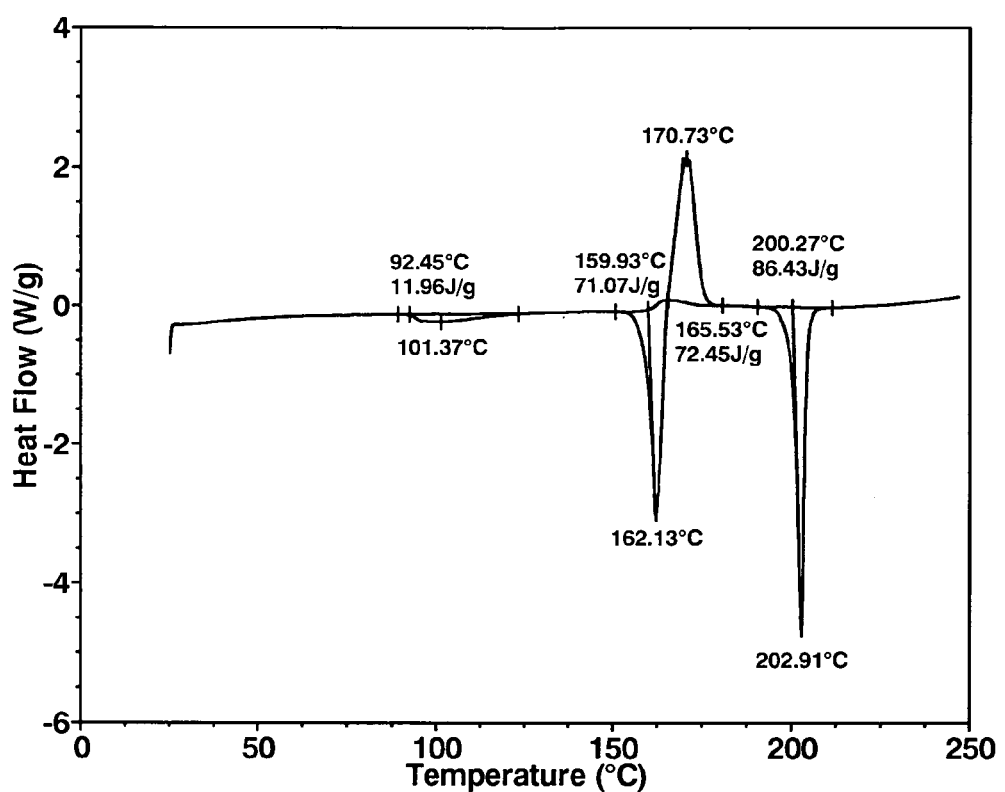
FIG. 5 shows a differential scanning calorimeter (DSC) curve of Compound I Form II.
Figure 6:
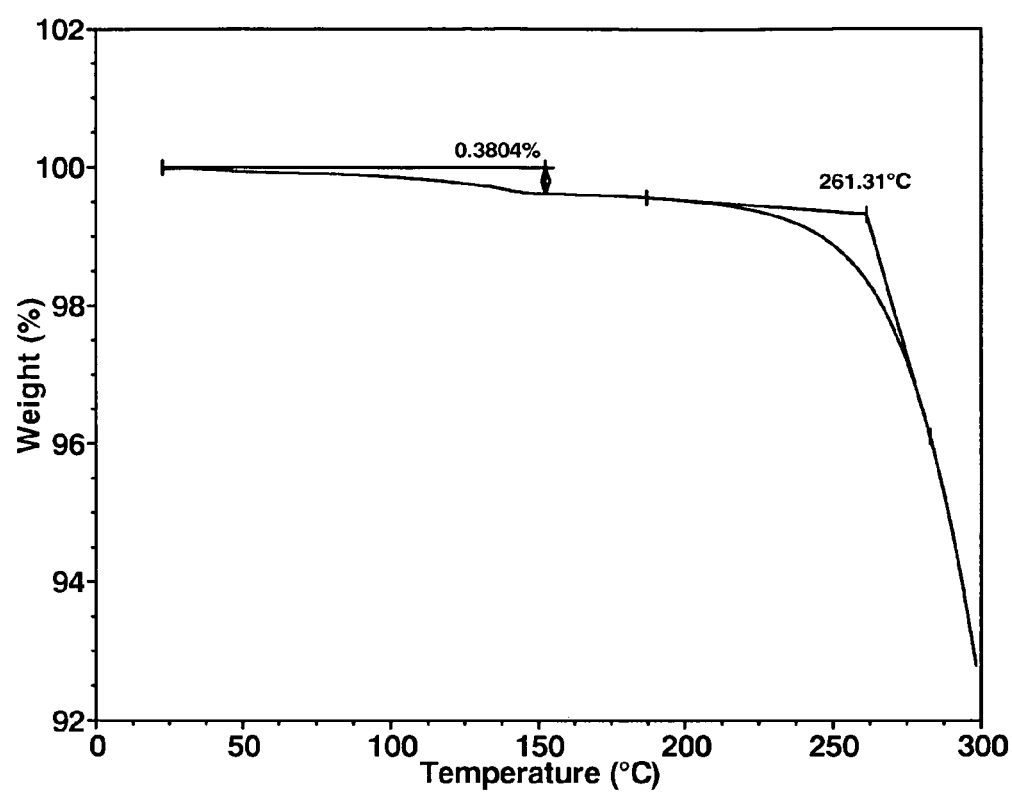
FIG. 6 shows a thermogravimetric analysis (TGA) of Compound I Form II.

Compound I Form II is a desolvated polymorph of Compound I (FIG. 4) and can be characterized by an X-ray powder diffractogram comprising the following peaks: 4.9, 11.2, 16.6, 17.4, 23.7, 27.4° 2θ±0.2° 2θ. Studies showed that Compound I Form II is derived from the de-solvation of Compound I Form V, a DCM solvate of Compound I. The DSC data shows an endotherm with onset at about 92° C., an endotherm with onset at about 160° C. followed by exotherm at about 166° C. and endotherm with onset at about 200° C. (FIG. 5). The thermogram shows about 0.38% weight loss below about 150° C. (FIG. 6). Karl Fischer shows 0.33% water. No form change was observed after heating to about 110° C. However, Compound I Form II re-crystallizes to Compound I Form VI after heating up to about 180° C.

Figure 13:
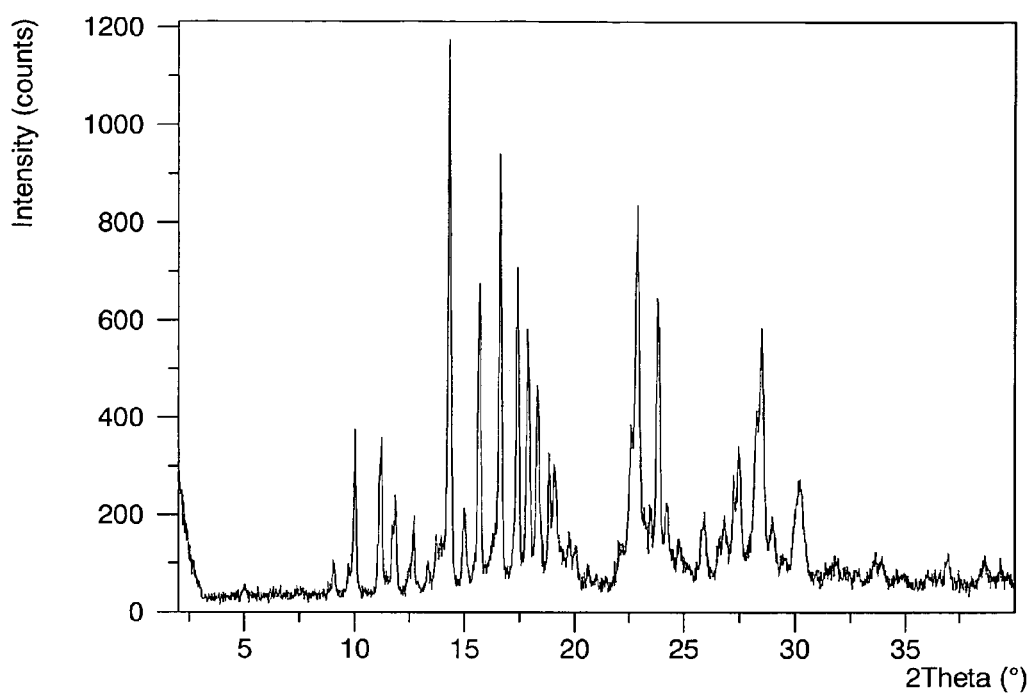
FIG. 13 shows an X-ray powder diffraction (XRPD) of Compound I Form V and Compound I Form II.
Figure 15:
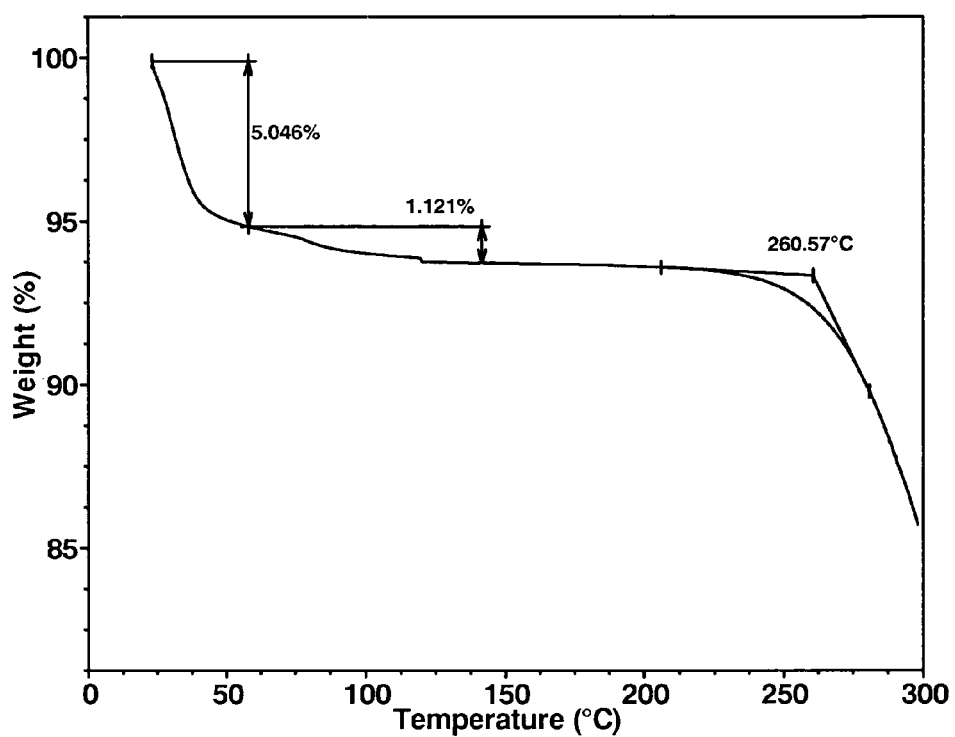
FIG. 15 shows a thermogravimetric analysis (TGA) of Compound I Form V and Compound I Form II.

Compound I Form V can be transiently observed by XRPD by analyzing the wet cake of Compound I derived from crystallizations performed in DCM or DCM/n-heptane mixtures (FIG. 13). Compound I Form V can also be characterized by a X-ray powder diffractogram comprising the following peaks: 9.7, 12.4, 13.3, 16.4, 17.2, 19.3, 22.2, 24.9, and 27.9° 2θ±0.2° 2θ. Upon drying, Compound I Form V readily desolvates to Compound I Form II as was shown by TGA (FIG. 15). To date, Compound I Form II has been obtained from DCM or a mixture of other solvents with DCM.

Figure 14:
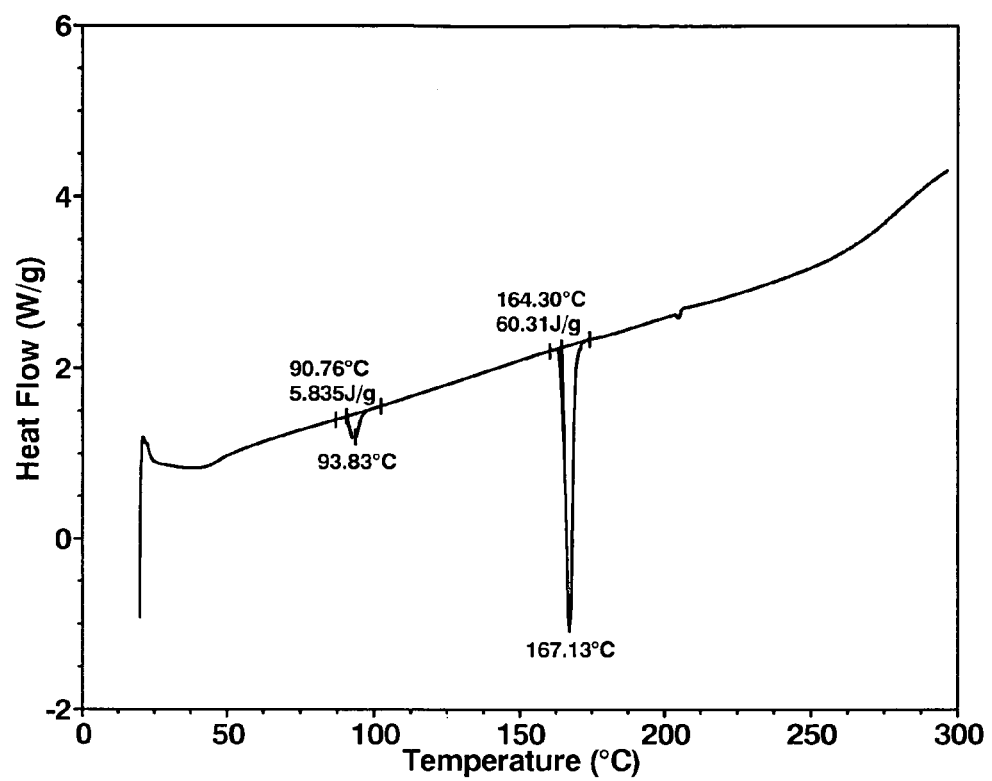
FIG. 14 shows a differential scanning calorimeter (DSC) curve of Compound I Form V and Compound I Form II.

Compound I Form II and Compound I Form V were also observed during a stable form screen of Compound I Form I in DCM (see Section 2.1 below). A slurry of Compound I Form I in DCM after about 24 hours produced a mixture of Forms II and V by XRPD. After about 14 days, the slurry was a mixture of Compound I Form II and Compound I Form V. The DSC data shows an endotherm with onset at about 91° C. and an endotherm with onset at about 164° C. (FIG. 14).

A single crystal of Compound I Form V was obtained during a stable form screen (Section 2.1 below) which confirmed the structure of Compound I DCM solvate. The XRPD of freshly acquired wet cake samples from DCM suspension are similar to the calculated powder pattern for Form V; the differences in the calculated powder pattern and experimental pattern can be attributed to partial de-solvation to an intermediate form (full drying of the DCM wet cake at RT yields Compound I Form II) and temperature anisotropy. If the postulated intermediate form from DCM is real, it is too poorly defined to merit a Form designation. Table 2 summarizes the Single Crystal Data for Compound I Form V.

TABLE 2

Single Crystal Data for Compound I Form V

| Type | Formula | Space Group | Distance (Å) | | | Angle (°) | | |
| --- | --- | --- | --- | --- | --- | --- | --- | --- |
| | | | a | b | C | α | β | γ |
| solvate | $C_{25}H_{26}Cl_2FN_7O$ | P2(1)/c | 20.1155 | 10.27050 | 12.6820 | 90 | 101.03 | 90 |

Thermodynamic Relationship Between Compound I Form I and Compound I Form II

Competition slurries between Compound I Form I and Compound I Form II revealed that Compound I Form I is the more stable polymorph in solvents lacking DCM at ambient temperature. For example, a mixture of Forms I and II in MeOH/water produces Form I while a mixture of the two forms slurried in DCM/n-heptane produces Form II.

1.3 Compound I Form III

Figure 7:
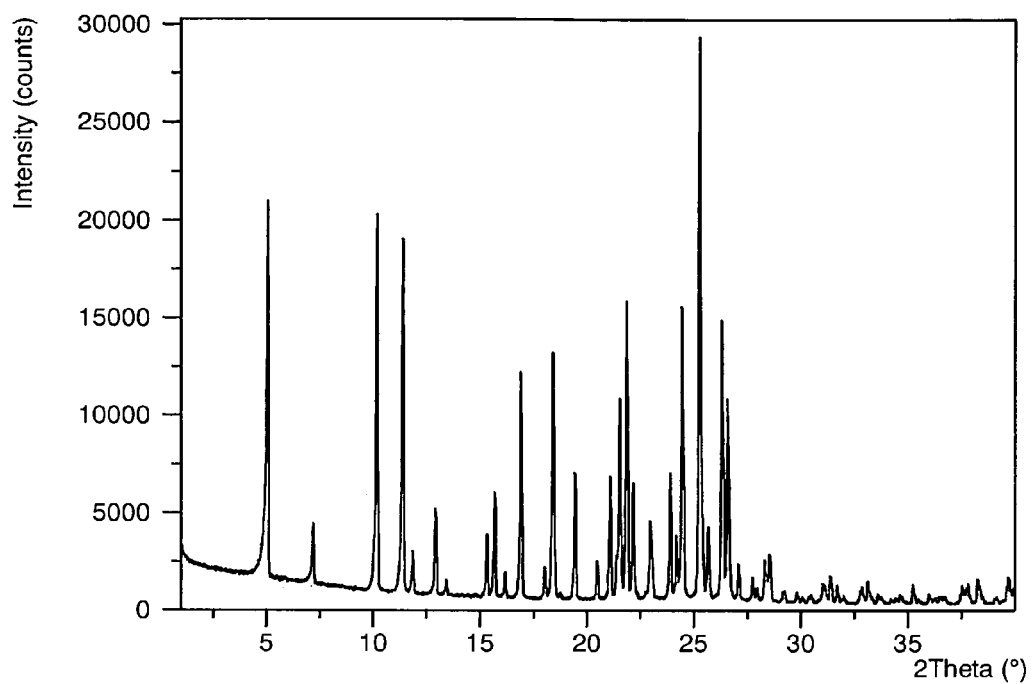
FIG. 7 shows an X-ray powder diffraction (XRPD) of Compound I Form III.
Figure 8:
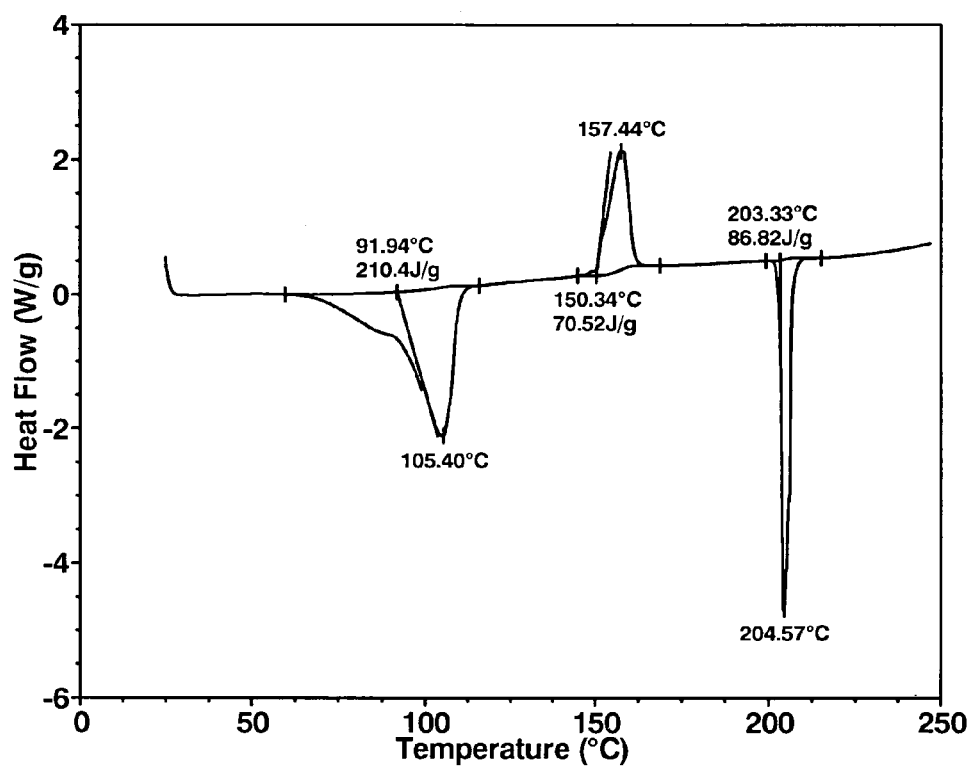
FIG. 8 shows a differential scanning calorimeter (DSC) curve of Compound I Form III.
Figure 9:
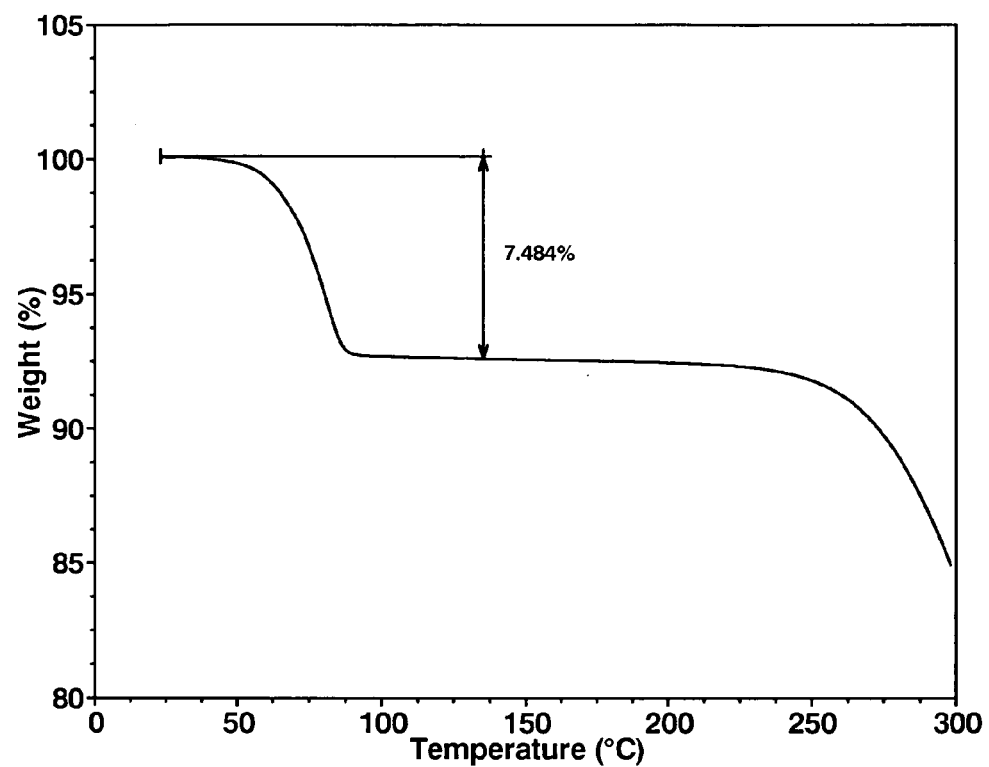
FIG. 9 shows a thermogravimetric analysis (TGA) of Compound I Form III.

Compound I Form III is a hydrated form that was obtained by suspending Compound I (about 100 mg) in methanol/water (0.215:0.785) mixture (1 mL) at about 50° C. for about 7 days (FIG. 7). The solids were isolated by vacuum filtration and dried under vacuum at room temperature. Compound I Form III can be characterized by an X-ray powder diffractogram comprising the following peaks: 5.1, 10.2, 11.4, 18.4, 21.9, and 25.3° 2θ±0.2° 2θ. TGA analysis of Compound I Form III shows about 7.5% mass loss at <140° C. (FIG. 9). Karl Fischer analysis shows about 7.0% water. The DSC of Form III shows a broad endotherm with onset at about 92° C., exotherm with onset at about 150° C., and with onset endotherm at about 203° C. (FIG. 8).

1.4 Compound I Form IV

Compound I Form IV is a hydrate that was observed to precipitate out of solution when 3 volumes of water were charged to a solution of Compound I in 4 volumes of methanol. The following procedure was used to obtain Form IV: Compound I (1 g) was dissolved in 4 mL of MeOH by heating to about 40° C. Water (3 mL) was charged to generate a thick slurry. Additional water (11.6 mL) was charged to the mixture to obtain a 0.9 water activity. The resulting slurry was cooled to room temperature and filtered. The wet cake was dried in a vacuum oven at room temperature to obtain Compound I Form IV (0.98 g).

Figure 10:
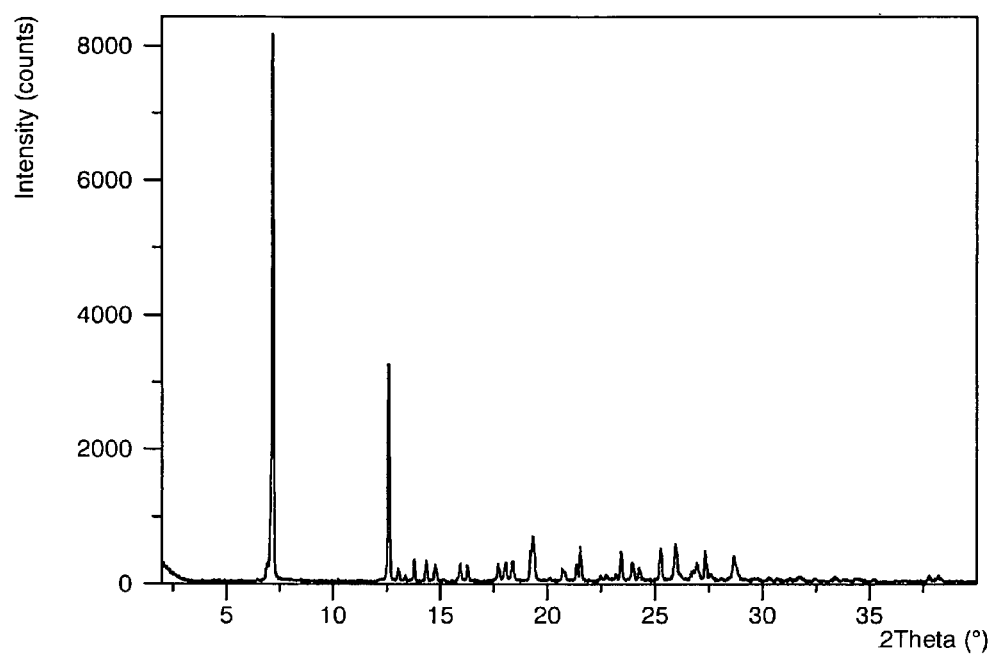
FIG. 10 shows an X-ray powder diffraction (XRPD) of Compound I Form IV.
Figure 11:
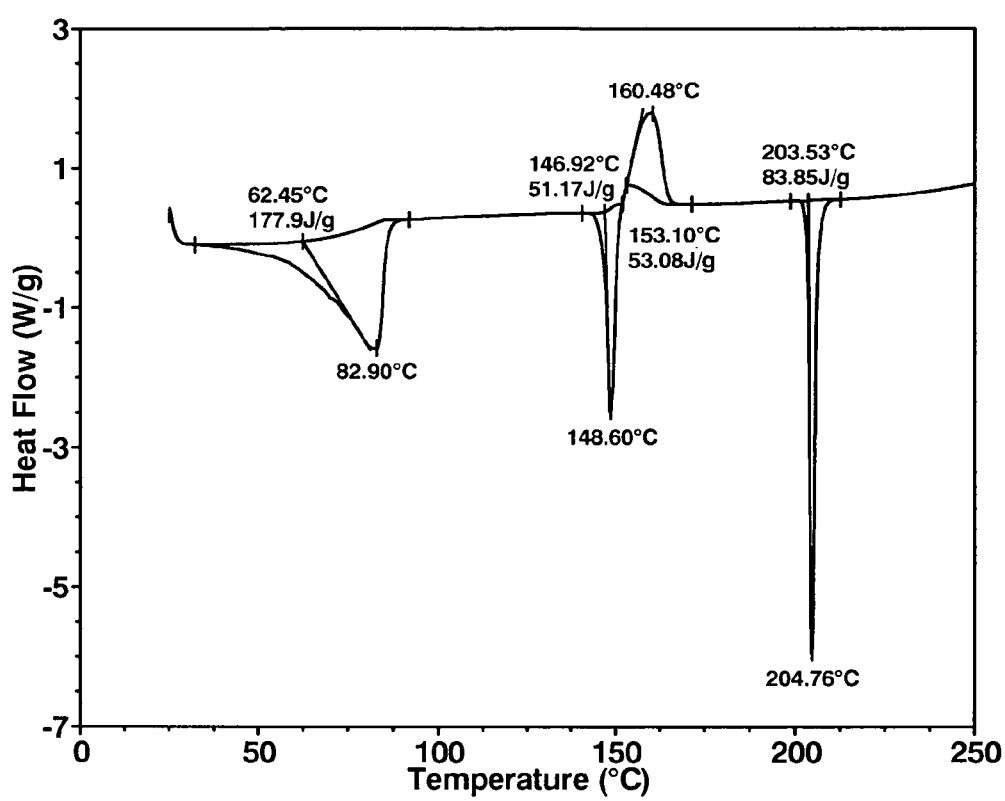
FIG. 11 shows a differential scanning calorimeter (DSC) curve of Compound I Form IV.
Figure 12:
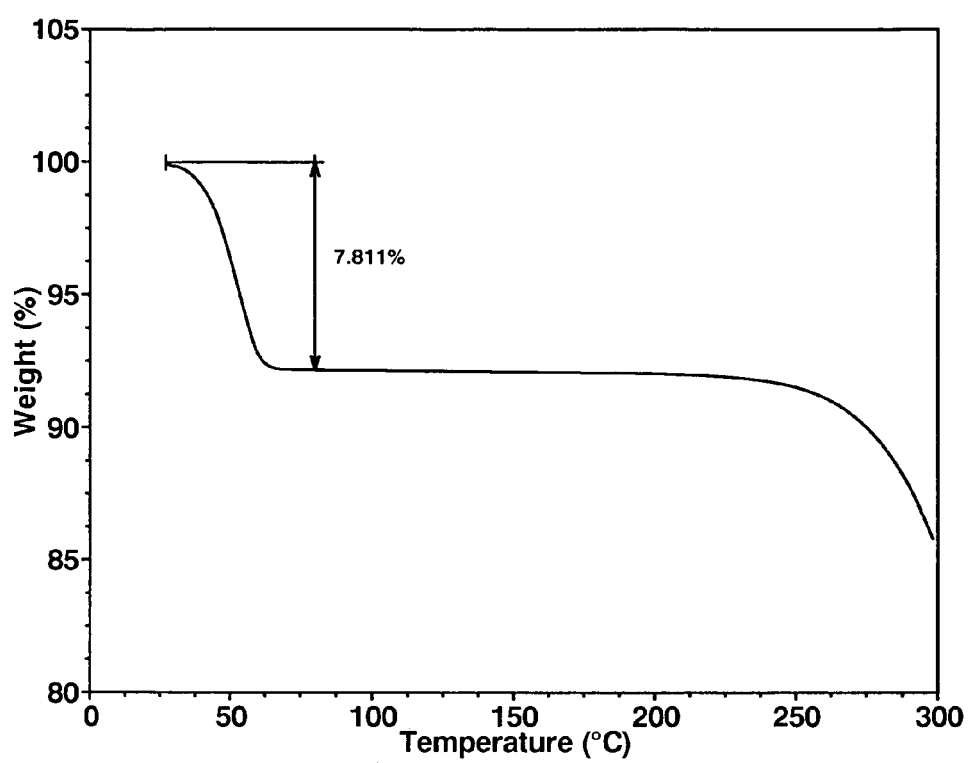
FIG. 12 shows a thermogravimetric analysis (TGA) of Compound I Form IV.

Compound I Form IV can be characterized by an X-ray powder diffractogram comprising the following peaks: 7.2, 12.6, 13.8, 19.3, 25.9, and 28.6° 2θ±0.2° 2θ (FIG. 10). DSC shows a broad endotherm with onset at about 62° C., sharp endotherm with onset at about 147° C., followed by exotherm with onset at about 153° C. and endotherm with onset at about 204° C. (FIG. 11). TGA shows 7.8% weight loss below 75° C. corresponding to the loss of 2 equivalents of water (FIG. 12). Karl Fischer analysis also shows about 7.9% water indicating that Form IV is a di-hydrate.

1.5 Compound I Form VI

Figure 16:
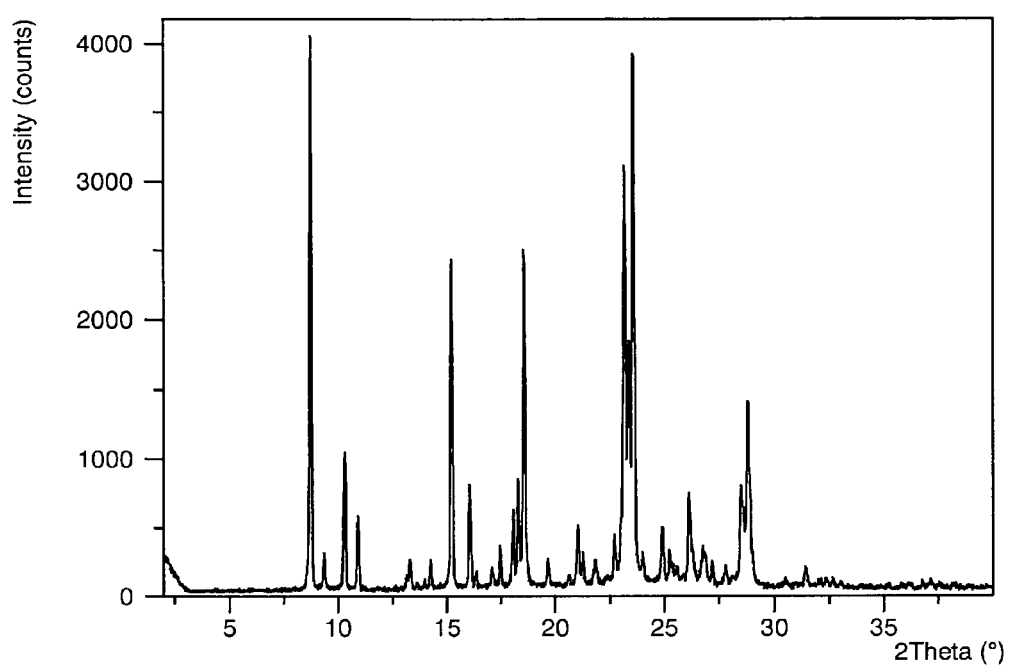
FIG. 16 shows an X-ray powder diffraction (XRPD) of Compound I Form VI.
Figure 17:
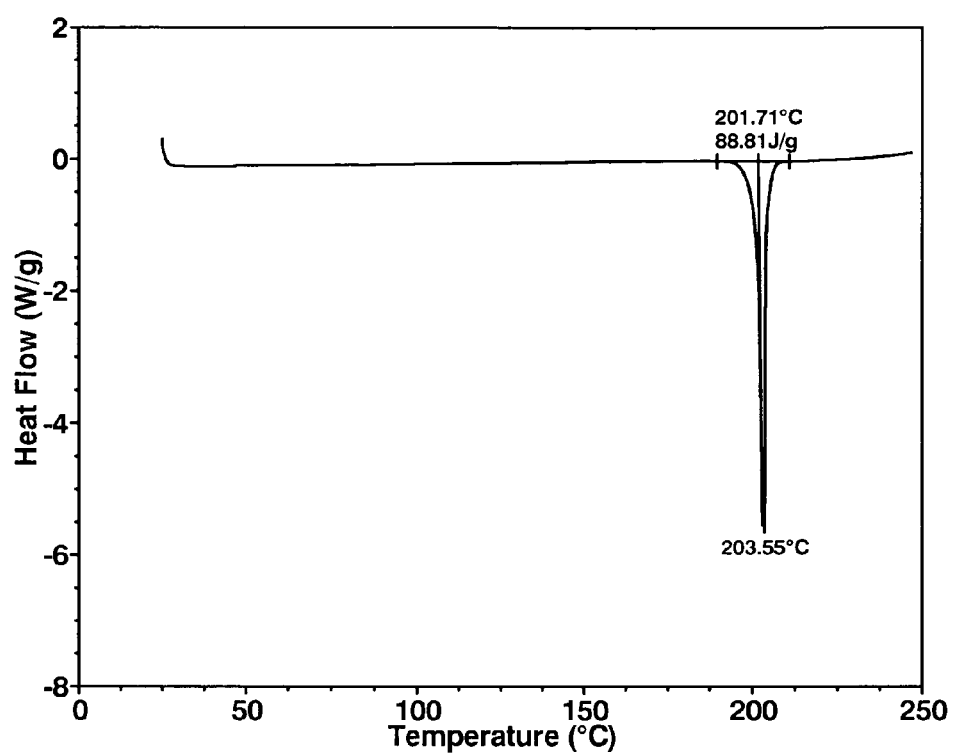
FIG. 17 shows a differential scanning calorimeter (DSC) curve of Compound I Form VI.
Figure 18:
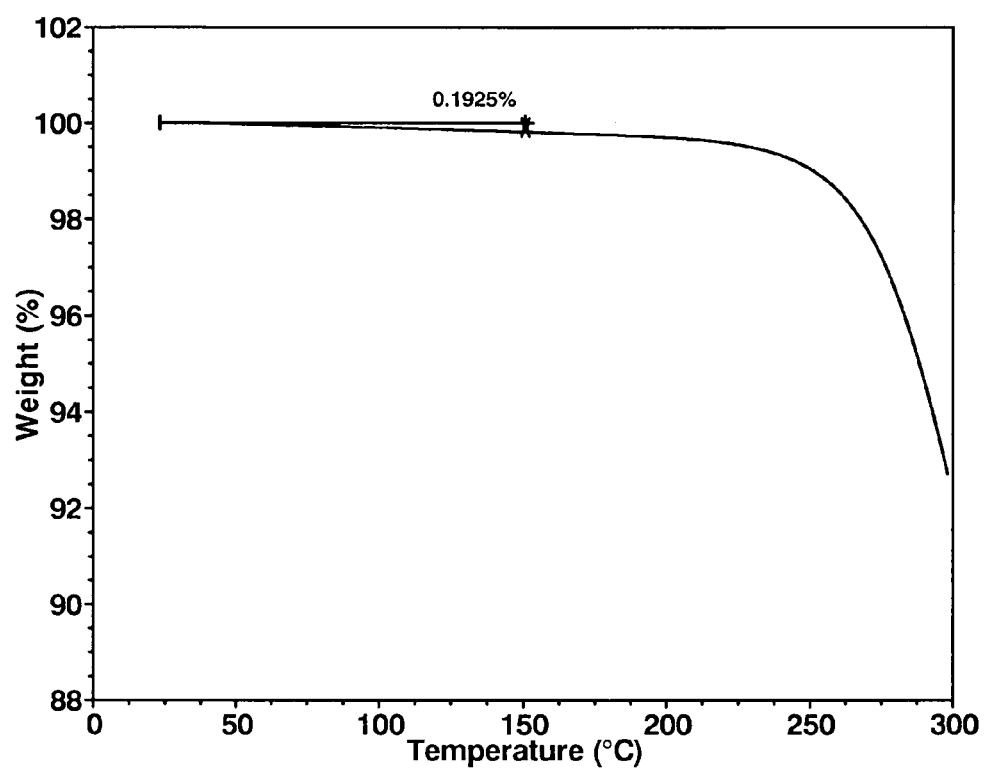
FIG. 18 shows a thermogravimetric analysis (TGA) of Compound I Form VI.

Compound I Form VI was generated by fast evaporation under vacuum from a number of different solvents or solvent mixtures (acetonitrile, ethanol, tetrahydrofuran, methanol/methyl isobutyl ketone and methanol/1-butanol). Initially, Compound I Form VI was isolated in an impure state and these samples were contaminated with traces of Compound I Form I or other polymorphs. However, the pure form was isolated after heating the Compound I Form II at 180° C. for about 10 min (FIG. 16), and also by pouring a hot ethanol solution of Compound I into heptane. Compound I Form VI can be characterized by an X-ray powder diffractogram comprising the following peaks: 8.8, 10.3, 15.2, 18.6, 23.2, 23.5, and 28.8° 2θ±0.2° 2θ. The DSC trace of Compound I Form VI shows single sharp endotherm with onset at about 202° C. (FIG. 17). The TGA thermogram shows about 0.2% of continuous weight loss up to about 150° C. (FIG. 18). Karl Fisher analysis shows about 0.1% water.

1.6 Compound I Form VII

Figure 41:
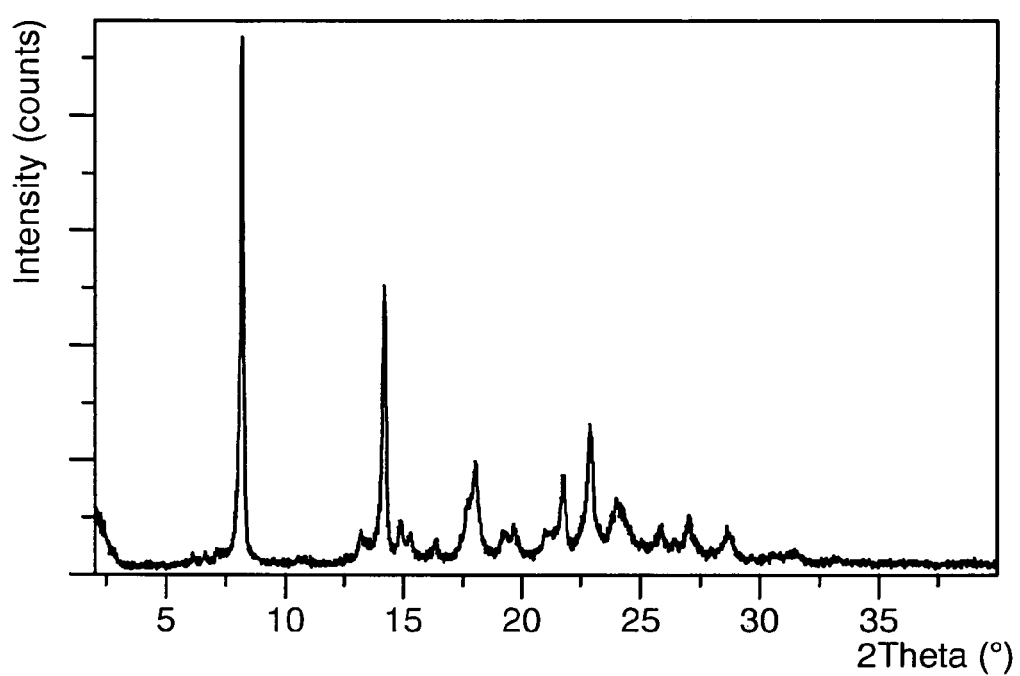
FIG. 41 shows an X-ray powder diffraction (XRPD) of Compound I Form VII.
Figure 42:
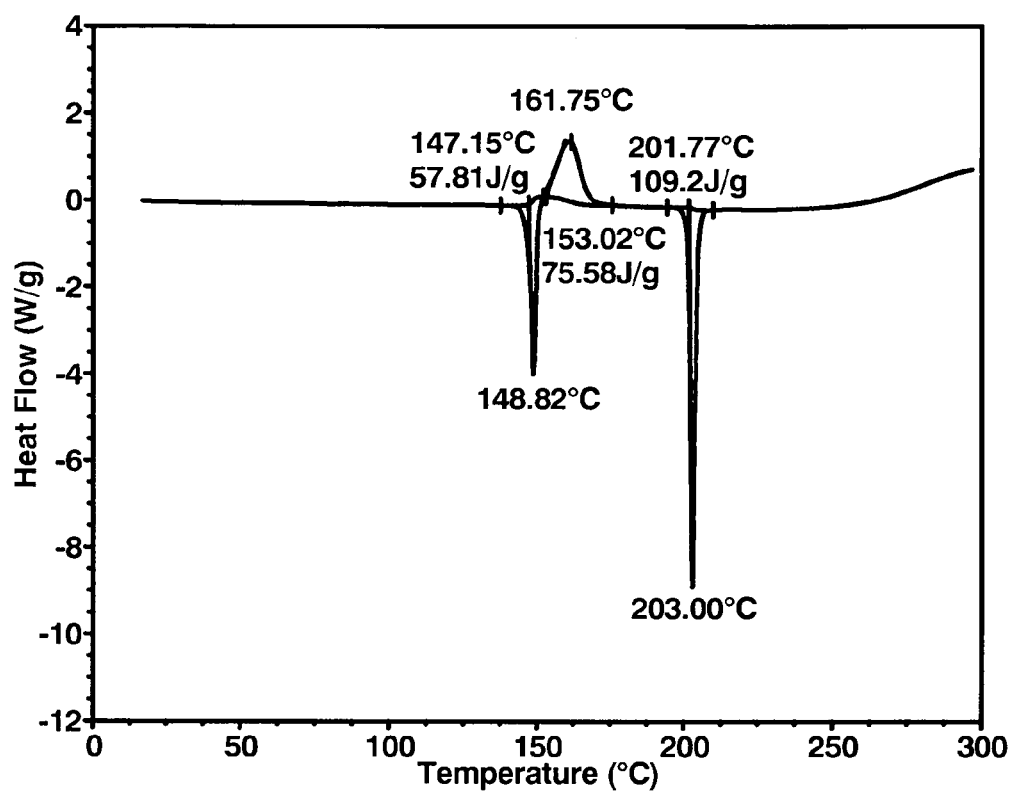
FIG. 42 shows a differential scanning calorimeter (DSC) curve of Compound I Form VII.
Figure 43:
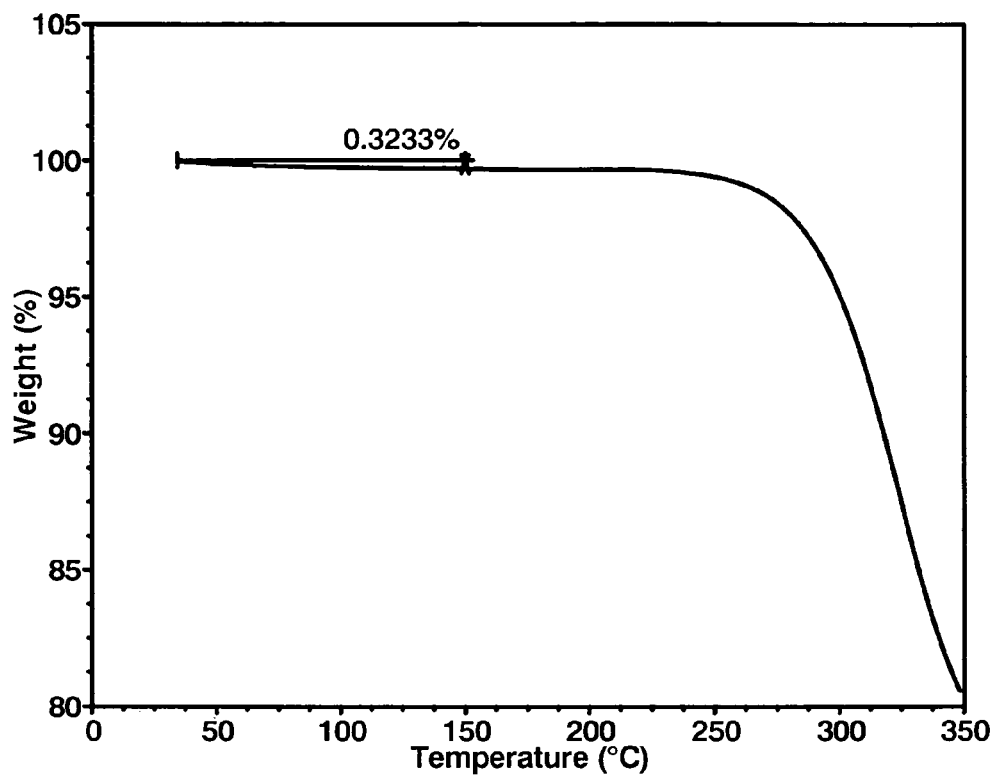
FIG. 43 shows a thermogravimetric analysis (TGA) of Compound I Form VII.

Compound I Form VII was generated by exposing Compound I Form IV (which was made as discussed above), to low relative humidity conditions (FIG. 41). Compound I Form VII is a dehydrated form of Compound I Form IV with typical KF value of <0.1%. Compound I Form VII rapidly converts back to Compound I Form IV at ambient temperature and humidity. Compound I Form VII can be characterized by an X-ray powder diffractogram comprising the following peaks: 8.2, 14.2, 18.0, 21.7, and 22.9° 2θ±0.2° 2θ. Compound I Form VII was also obtained by heating Compound I Form IV at about 110° C. with nitrogen flow, after DVS analysis of Compound I Form IV at low relative humidity, and by drying Compound I Form IV in the vacuum oven at about 45° C. according to XRPD analysis. The DSC trace of Compound I Form VII showed sharp endotherm with onset at about 147° C., followed by exotherm with onset at about 153° C. and final melt with onset at 202° C. (FIG. 42). The TGA thermogram showed 0.3% of continuous weight loss below 150° C. after about 30 minutes exposure under ambient conditions (FIG. 43). This weight loss may correspond to the reabsorbed surface moisture at ambient humidity. Competitive slurries of Compound I Form I and Compound I Form VII in ethanol afforded full conversion of Compound I Form VII to Compound I Form I after agitating overnight.

1.7 Compound I Form VIII

Figure 44:
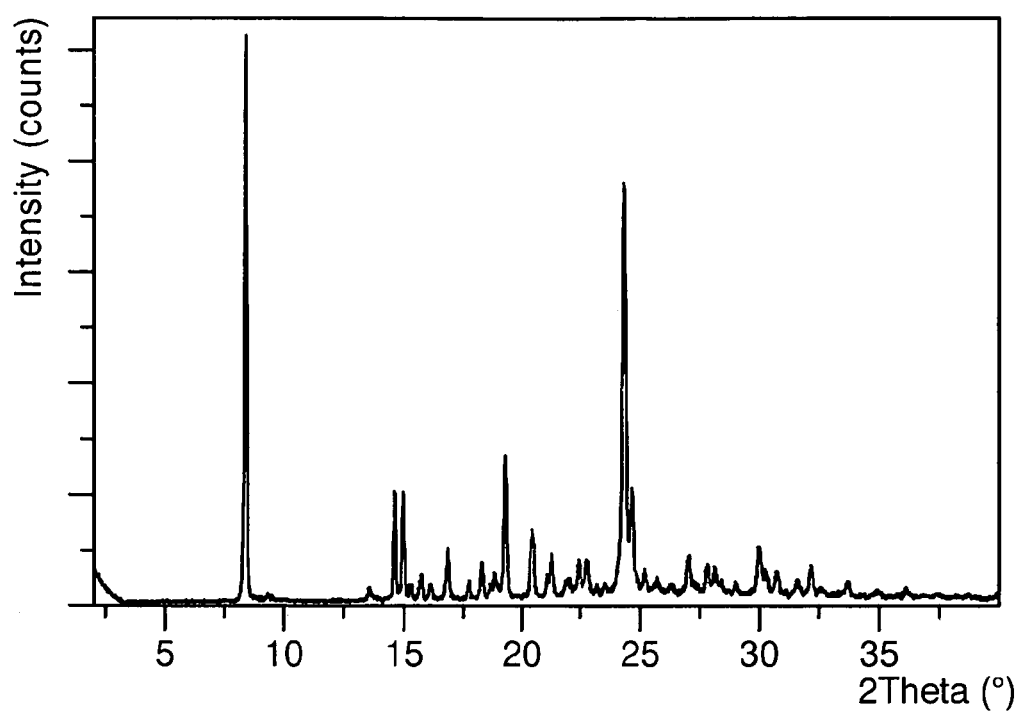
FIG. 44 shows an X-ray powder diffraction (XRPD) of Compound I Form VIII.
Figure 45:
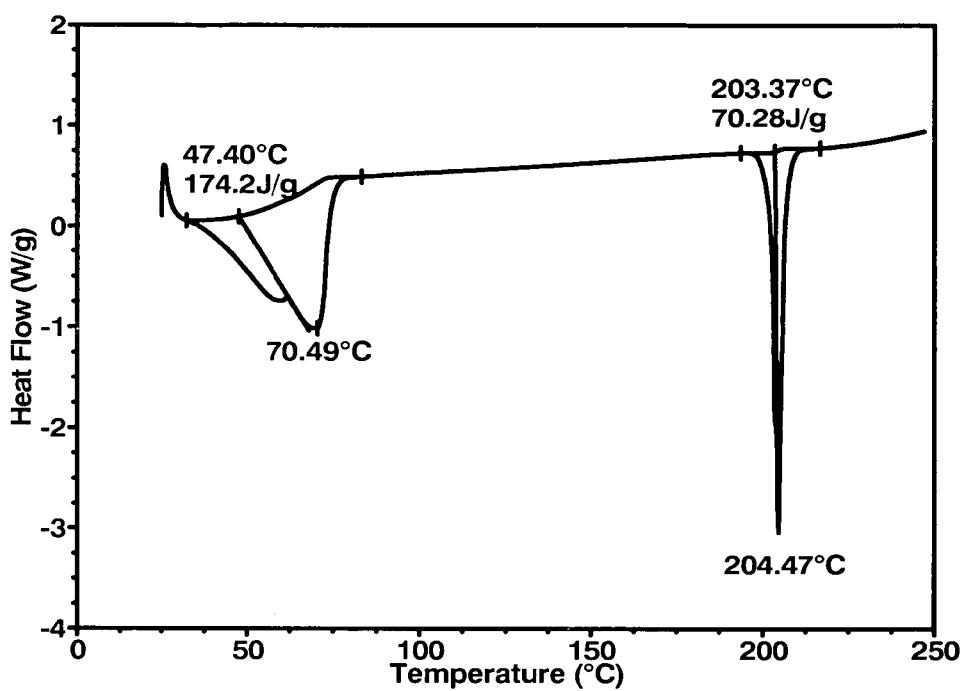
FIG. 45 shows a differential scanning calorimeter (DSC) curve of Compound I Form VIII.
Figure 46:
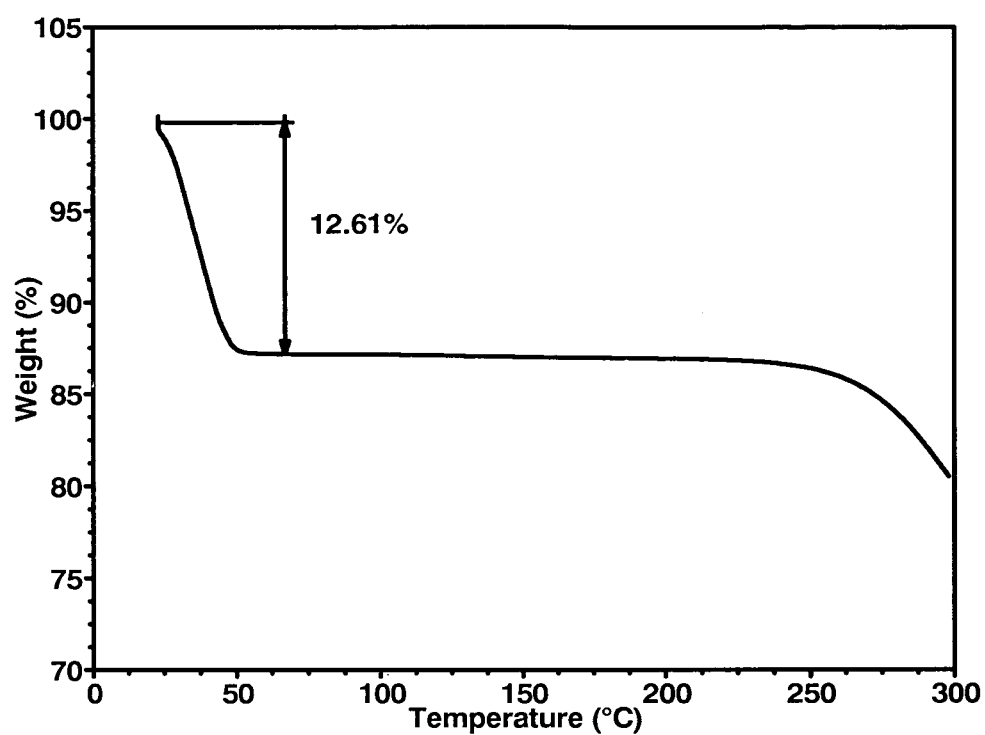
FIG. 46 shows a thermogravimetric analysis (TGA) of Compound I Form VIII.

Compound I Form VIII is an unstable hydrate which rapidly loses water and converts to Compound I Form VI at ambient conditions. Compound I Form VIII was obtained after equilibration of unsolvated Compound I Form VI in humidity chamber at 90% RH and from the slurry of Compound I Form VI in EtOH/water at 0.9 water activity (FIG. 44). Compound I Form VIII can be characterized by an X-ray powder diffractogram comprising the following peaks: 8.4, 14.6, 15.0, 16.8, 19.3, 20.4, and 24.3° 2θ±0.2° 2θ. Isolated solids were dried with filter paper to remove residual solvents and analyzed by DSC, TGA and KF. The DSC trace showed broad endotherm below 75° C. and sharp endotherm with onset at about 203° C. (FIG. 45). The TGA thermogram showed ~12.6% weight loss below 75° C.

corresponding to the loss of residual solvents (FIG. 46). KF analysis afforded about 16.1% water.

1.8 Compound I Form IX

Figure 47:
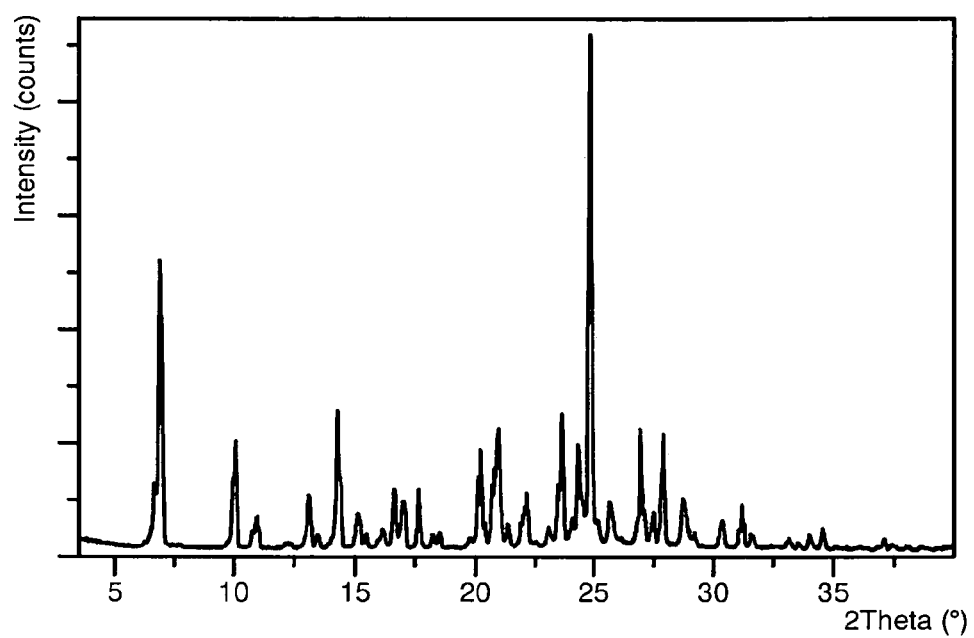
FIG. 47 shows an X-ray powder diffraction (XRPD) of Compound I Form IX.
Figure 48:
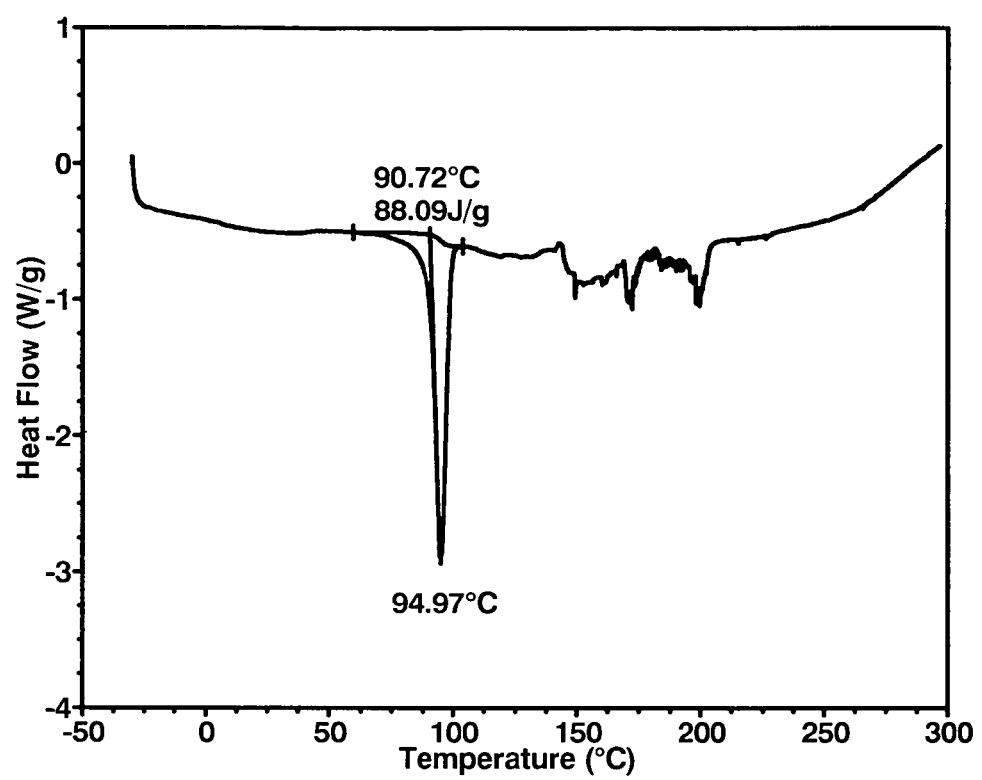
FIG. 48 shows a differential scanning calorimeter (DSC) curve of Compound I Form IX.
Figure 49:
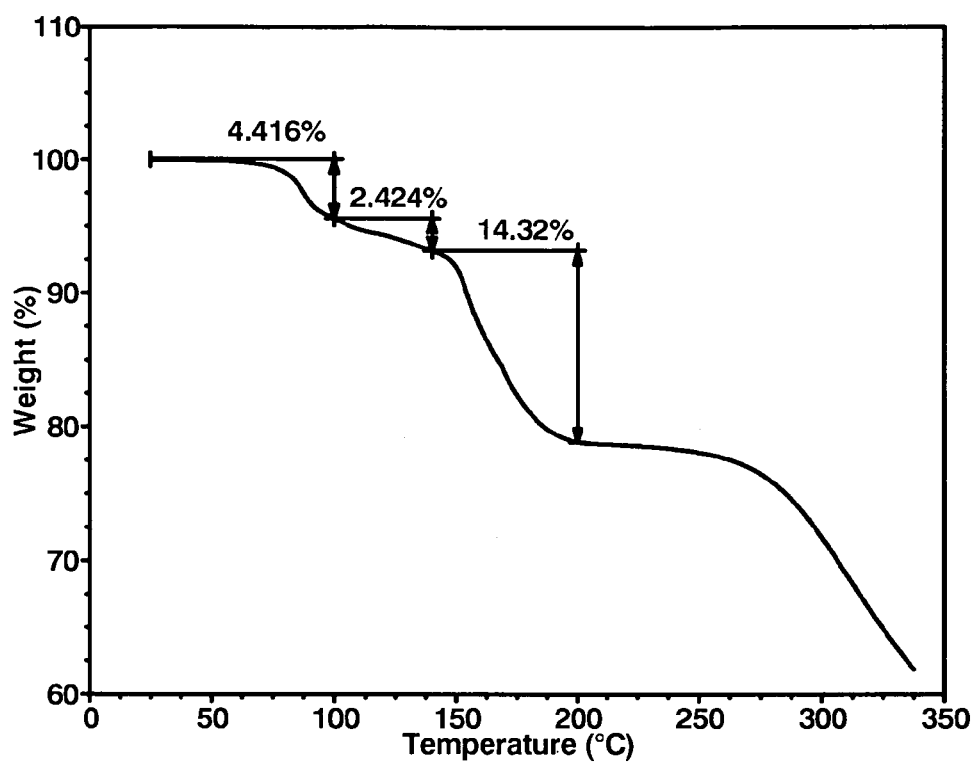
FIG. 49 shows a thermogravimetric analysis (TGA) of Compound I Form IX.

Compound I Form IX is an acetic acid solvate. Compound I Form IX was obtained by dissolving Compound I in glacial acetic acid and stirring at ambient temperature (FIG. 47). Additional Compound I was added to the solution until it became quite viscous, but saturation was not achieved over the course of a few days. The sample was stirred for more than two months before being placed into storage without agitation and at ambient conditions. During storage, crystalline material precipitated from solution. The material was collected by vacuum filtration and dried under ambient conditions. XRPD analysis indicated a crystalline material. Compound I Form IX can be characterized by an X-ray powder diffractogram comprising the following peaks: 6.9, 10.1, 14.3, 21.0, 23.7, 24.8, and 26.9° 2θ±0.2° 2θ. The DSC trace showed an endotherm with onset at about 91° C. (FIG. 48). A three tiered weight loss was detected during TGA analysis (FIG. 49). A total weight loss of 21.1% was measured. The final weight loss appears to occur well into the decomposition regime. A di-acetate or di-acetic acid solvate would lose 21.2% with the loss of the acetic acid. 1H NMR spectroscopy confirmed that two moles of acetic acid are present for every mole of Compound I. Form IX may be a di-acetic acid solvate which converts to Form I upon isolation and storage at ambient conditions.

1.9 Amorphous Compound I

Figure 50:
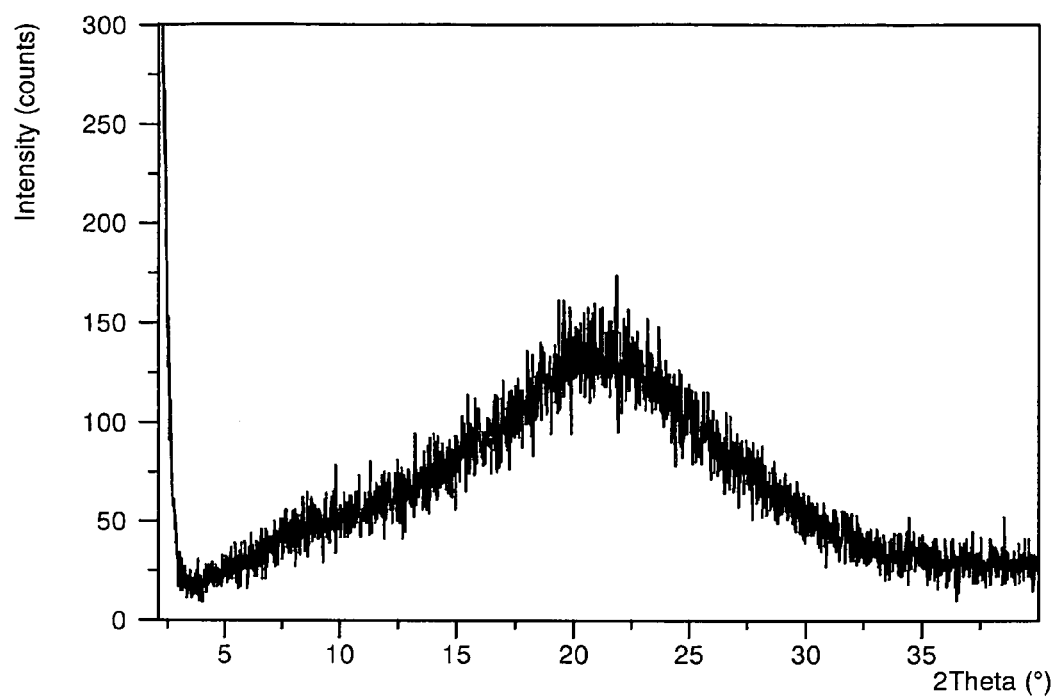
FIG. 50 shows an X-ray powder diffraction (XRPD) of Compound I (Amorphous).

Amorphous Compound I was obtained by fast vacuum evaporation of DCM solution, fast evaporation of methanol solution, and by drying Compound I Form III at 110° C. (FIG. 50).

2.1 Stable Form Screen of Compound I

Starting from Compound I Form I, a stable form screen of Compound I was performed. Compound I Form I was suspended with stirring in capped glass vials at RT. Samples from the suspensions were centrifuged/filtered and the isolated solids and liquids were analyzed. Solids were analyzed by XRPD and liquids were analyzed for solubility by TGA. Sampling and analysis were performed after one day and greater than fourteen days.

Table 3 presents the solvents which were investigated in this study. In this study, Compound I Form II and Compound I Form V were observed. In addition, crystals suitable for single crystal X-ray analysis of Compound I Form V were obtained from DCM and crystals suitable for single crystal X-ray analysis of Compound I Form I were obtained from methanol (discussed above). No new polymorphs of Compound I were discovered from the stable form screen.

TABLE 3

Compound I Stable Form Screen

| Compound I (mg) | Solvent | 24 Hour XRPD | 14+ Day XRPD |
|---|---|---|---|
| 70 | water | Form I | Form I |
| 77 | IPAC | Form I | Form I |
| 75 | MTBE | Form I | Form I |
| 76 | 2-propanol | Form I | Form I |
| ~200 | DCM | V, II | V |
| 80 | n-heptane | Form I | Form I |
| 90 | THF | Form I | Form I |
| 79 | acetone | Form I | Form I |
| ~150 | methanol | Form I | Form I |
| 85 | ACN | Form I | Form I |
| 79 | Ethanol | Form I | Form I |
| 64 | EtOAc | Form I | Form I |

3.1 Salt and Co-Crystal Screen of Compound I

A salt/co-crystal screen was performed using high throughput and manual techniques, and exemplary salts were obtained as described below.

3.1.1 Compound I Esylate Form I 60.4 mg Compound I was slurried in 1 mL ethanol at approximately 60° C. Then, 12 µL ethanesulfonic acid (about 1.1 equivalents) was added to the mixture, and the sample clarified. The sample was allowed to cool to ambient temperature and allowed to evaporate to dryness. The XRPD pattern of the obtained solids is presented in FIG. 19.

Figure 20:
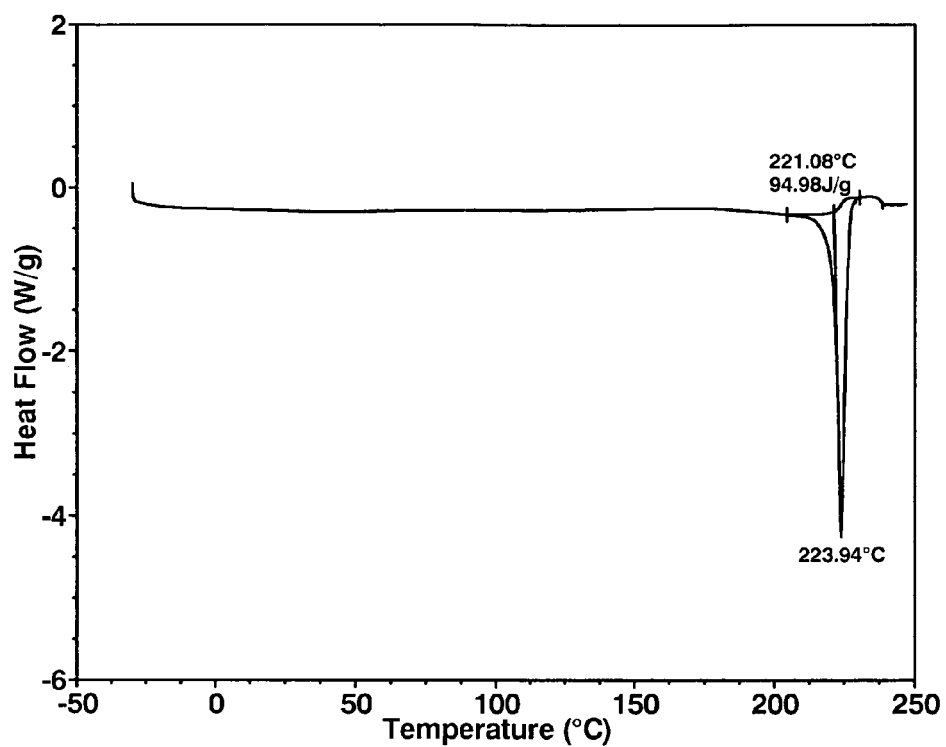
FIG. 20 shows a differential scanning calorimeter (DSC) curve of Compound I Esylate Form I.
Figure 21:
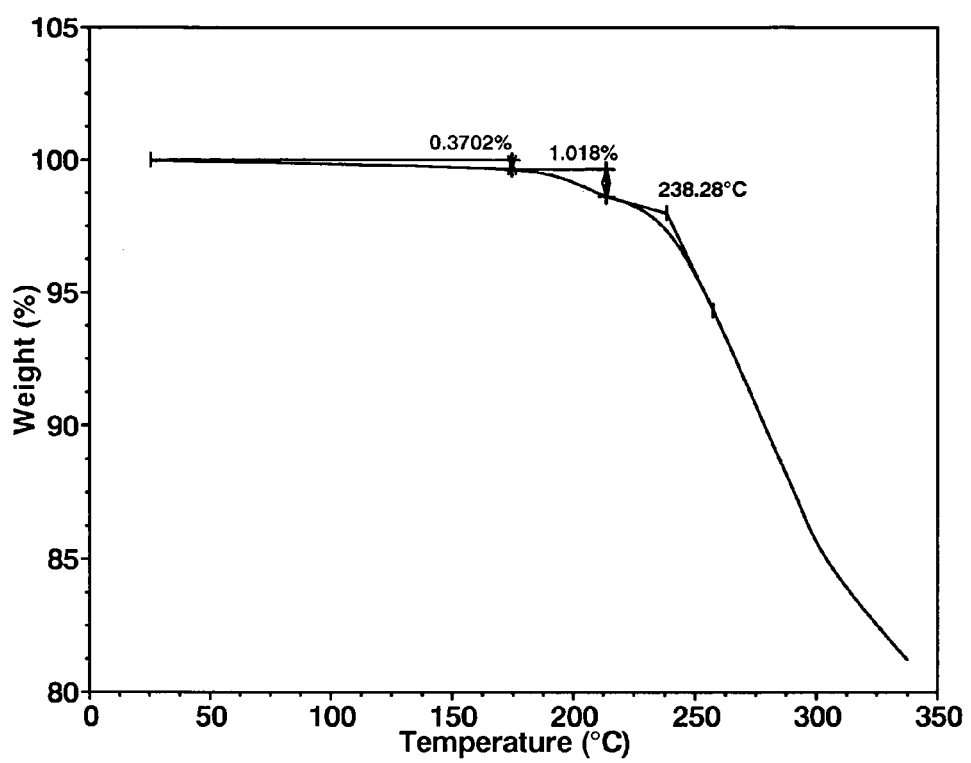
FIG. 21 shows a thermogravimetric analysis (TGA) of Compound I Esylate Form I.
Figure 27:
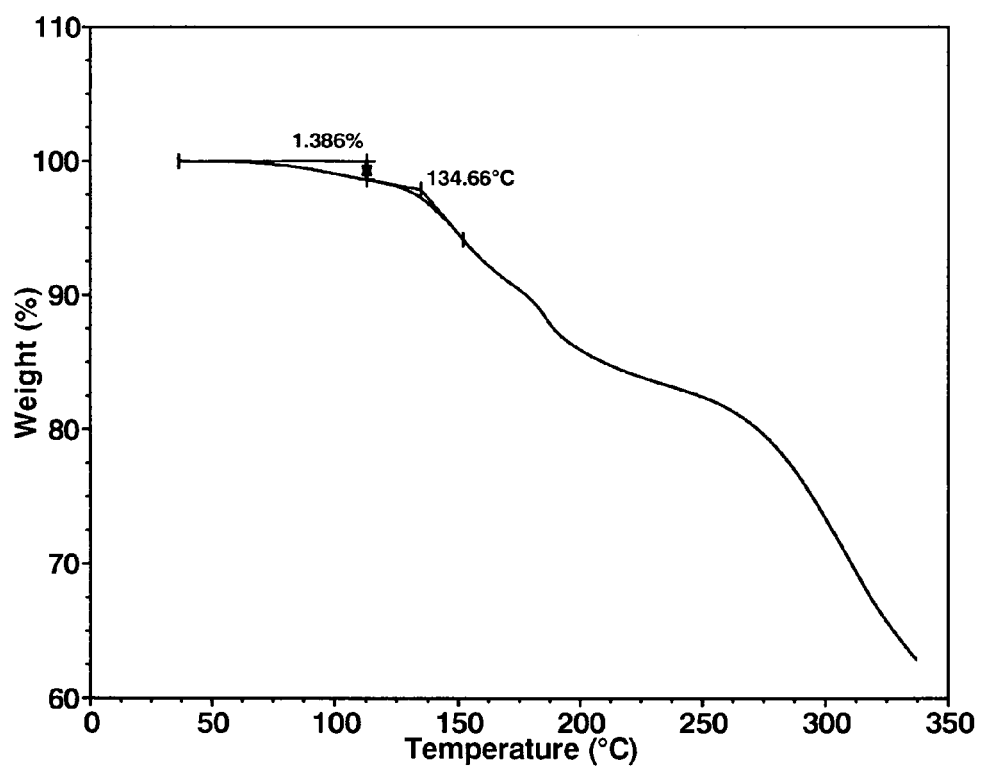
FIG. 27 shows a thermogravimetric analysis (TGA) of Compound I Glycolate Form I.

The DSC thermogram shows a single endotherm with onset at about 221° C. (FIG. 20). TGA shows about a 0.4% weight loss below about 175° C. and about 1.0% weight loss between about 175 to about 210° C., followed by the decomposition (FIG. 27). $^1$H NMR spectrum is consistent with the structure with approximately a 1:1 ratio of Compound I:ethanesulfonic acid. High humidity stress test at 75% RH/RT did not show any evidence of deliquescence.

3.1.2 Compound I Fumarate Form I 90.8 mg Compound I was stirred with 0.75 mL ethanol at approximately 60° C. Then, 48.2 mg fumaric acid (2 molar equivalents) was charged to the solution. The sample was stirred at elevated temperature for approximately 2 hours and then was allowed to cool to ambient temperature. The resulting solids were collected by vacuum filtration and left to dry under ambient conditions. The XRPD pattern is presented in FIG. 22.

Figure 23:
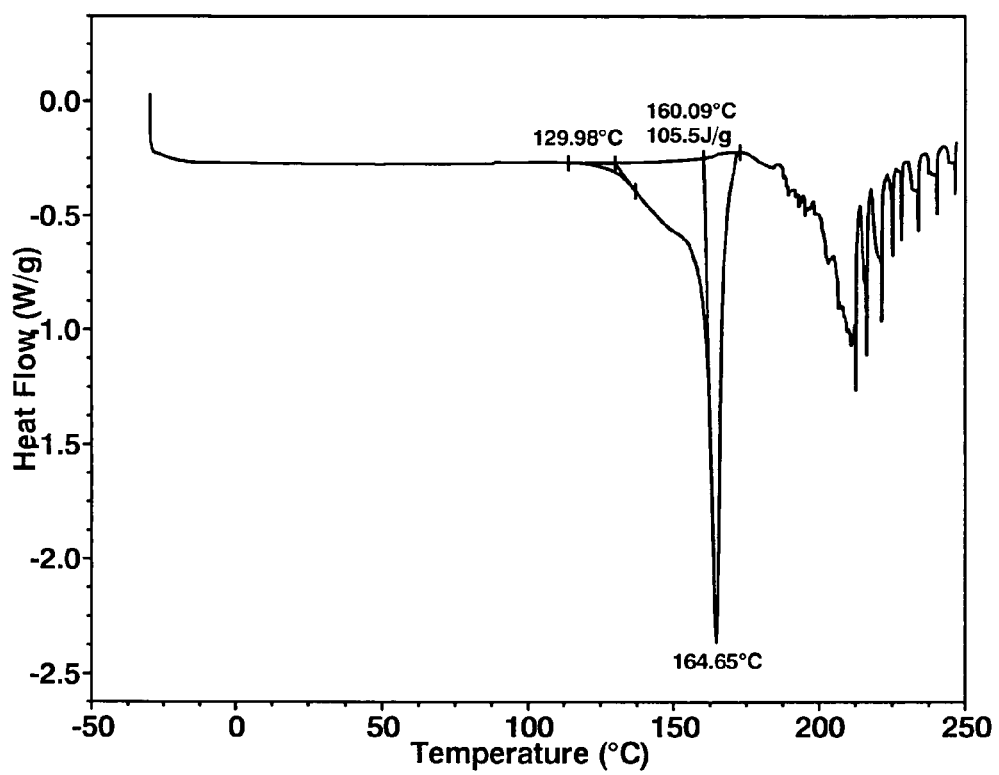
FIG. 23 shows a differential scanning calorimeter (DSC) curve of Compound I Fumarate Form I.
Figure 24:
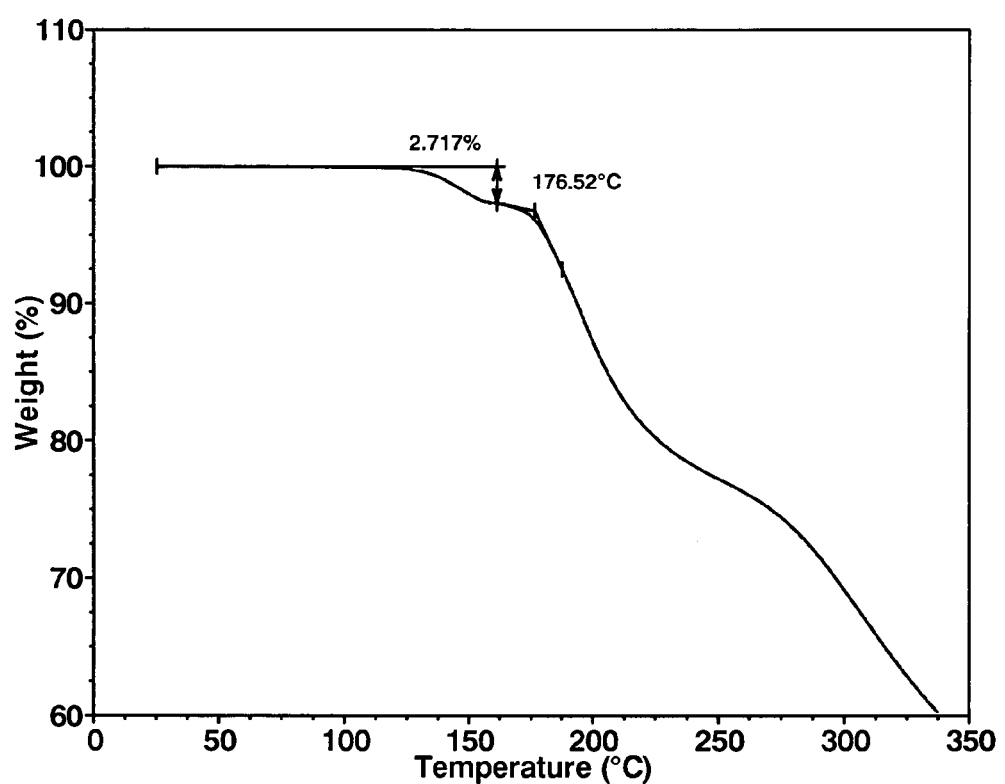
FIG. 24 shows a thermogravimetric analysis (TGA) of Compound I Fumarate Form I.

The DSC thermogram shows an endotherm with a broad shoulder with onset at about 130° C. (FIG. 23). The TGA trace shows about a 2.7% weight loss between about 125-160° C., followed by decomposition (FIG. 24). $^1$H NMR spectrum is consistent with the structure with approximately 1:1 ratio of Compound I:fumaric acid and residual amount of EtOH. High humidity stress test at 75% RH/RT did not show any evidence of deliquescence.

3.1.3 Compound I Glycolate Form I 109.6 mg Compound I was slurried with 0.75 mL ethanol at approximately 60° C. Then, 38.7 mg glycolic acid (2 molar equivalents) was slowly added to the mixture. The sample was stirred at elevated temperature for approximately 2 hours before it was allowed to cool to ambient temperature with stirring. The solids were collected by vacuum filtration and dried under ambient conditions. The XRPD pattern of the obtained solids is presented in FIG. 25.

Figure 26:
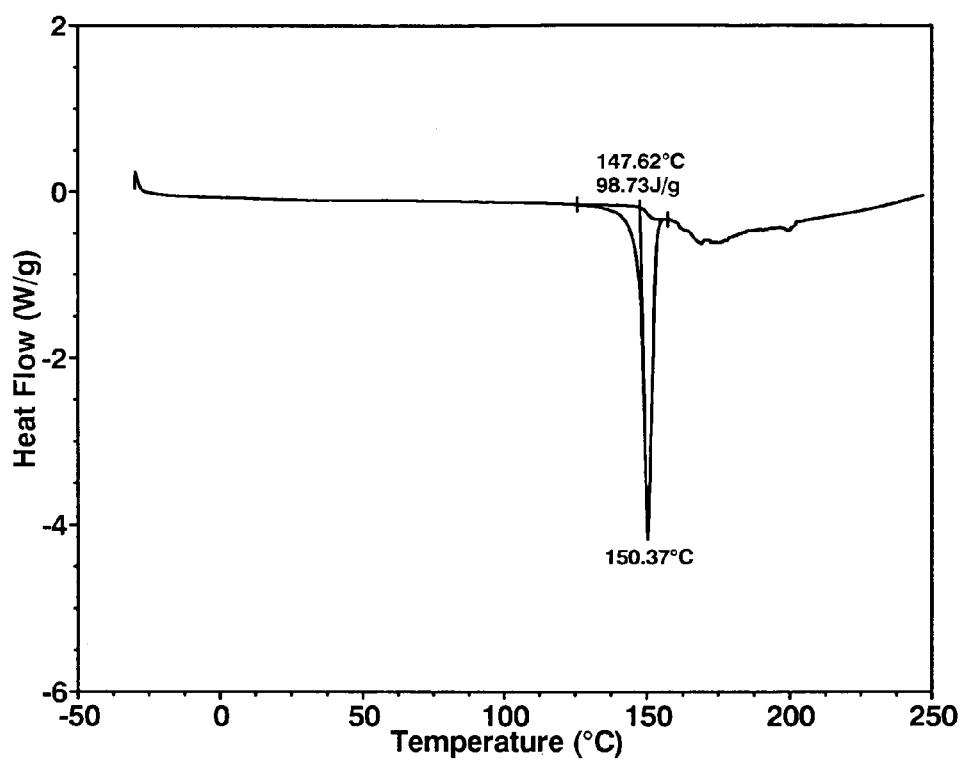
FIG. 26 shows a differential scanning calorimeter (DSC) curve of Compound I Glycolate Form I.

The DSC thermogram shows a single endotherm with onset at about 148° C. (FIG. 26). TGA shows about 1.4% weight loss below about 120° C. (FIG. 27). $^1$H NMR spectrum is consistent with the structure with 1:1 ratio of Compound I:glycolic acid. High humidity stress test at 75% RH/RT did not show any evidence of deliquescence.

3.1.4 Compound I HCl Form I 142.2 mg Compound I was slurried with 1 mL ethanol at approximately 60° C. Then, 30 µL concentrated aqueous HCl (about 1.1 molar equivalents) was slowly added. The mixture clarified. The sample was allowed to cool to ambient temperature with stirring. No solids were generated. The solution volume was reduced by evaporation until solids precipitated. The solids were collected by vacuum filtration and left to dry under ambient conditions. The XRPD pattern of these solids is presented in FIG. 28.

Figure 29:
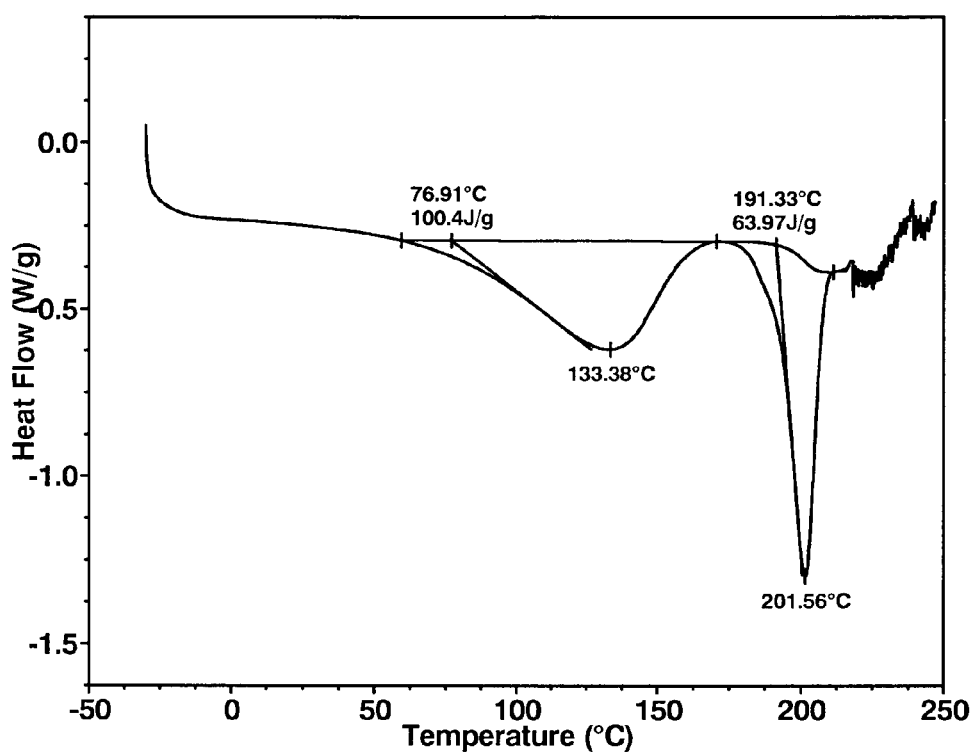
FIG. 29 shows a differential scanning calorimeter (DSC) curve of Compound I HCl Form I.
Figure 30:
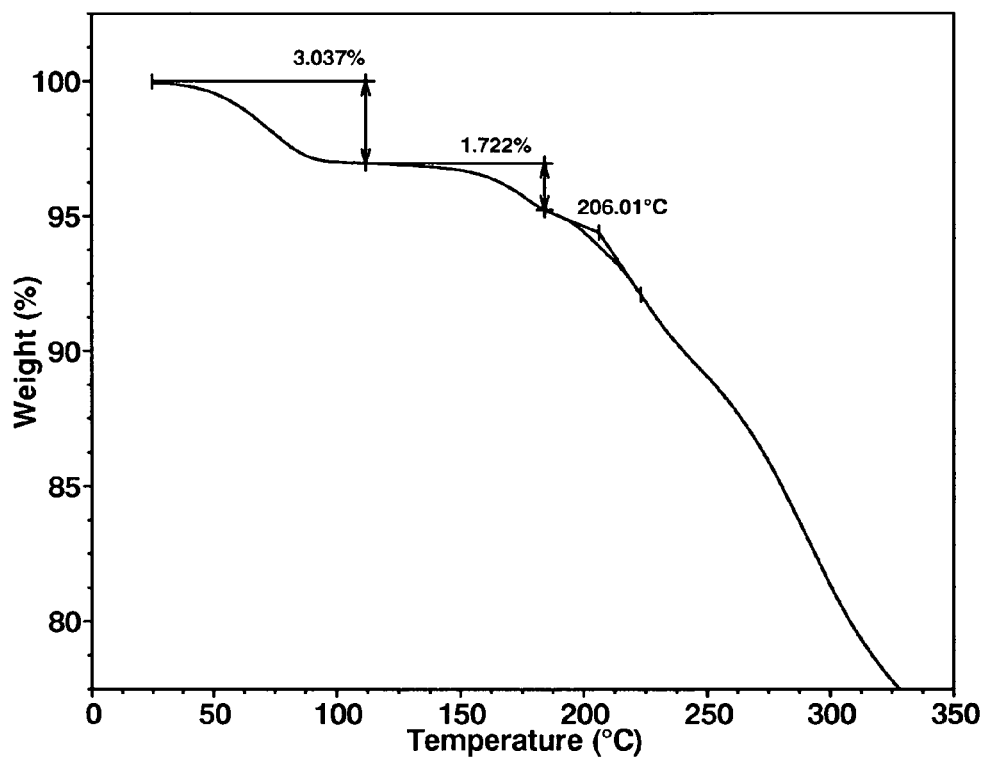
FIG. 30 shows a thermogravimetric analysis (TGA) of Compound I HCl Form I.

The DSC thermogram shows a broad endotherm with onset at about 77° C., followed by endotherm at about 191° C. (FIG. 29). The TGA trace shows about a 3.0% weight loss below about 101° C. and about 1.7% weight loss between about 110-180° C. (FIG. 30). The $^1$H NMR spectrum is consistent with the structure. High humidity stress test at 75% RH/RT did not show any evidence of deliquescence.

3.1.5 Compound I Maleate Form I 108.6 mg Compound I was slurried with 1 mL acetonitrile at approximately 40° C. Then, 28.8 mg maleic acid (1 molar equivalent) was added and the sample was stirred at elevated temperature. The sample was then stirred at ambient temperature and the volume was reduced and an oil resulted. 250 µL acetonitrile was added and the sample was slurried at ambient temperature. Solids were collected by vacuum filtration and dried under ambient conditions. The XRPD pattern of the obtained solids is presented in FIG. 31.

Figure 32:
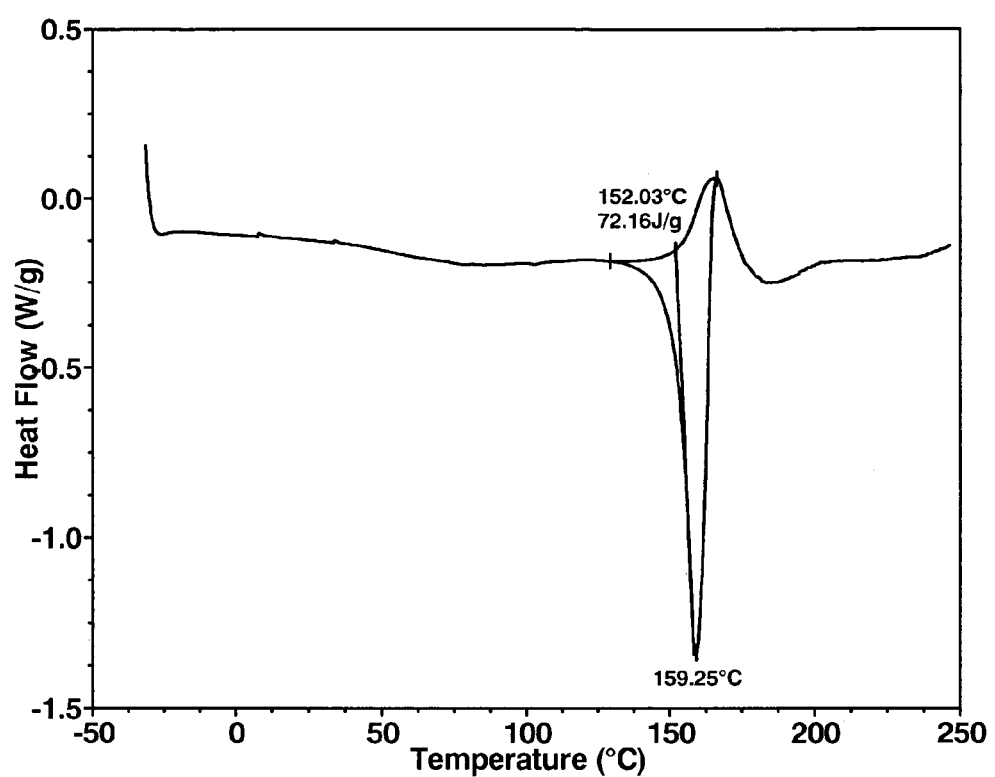
FIG. 32 shows a differential scanning calorimeter (DSC) curve of Compound I Maleate Form I.
Figure 33:
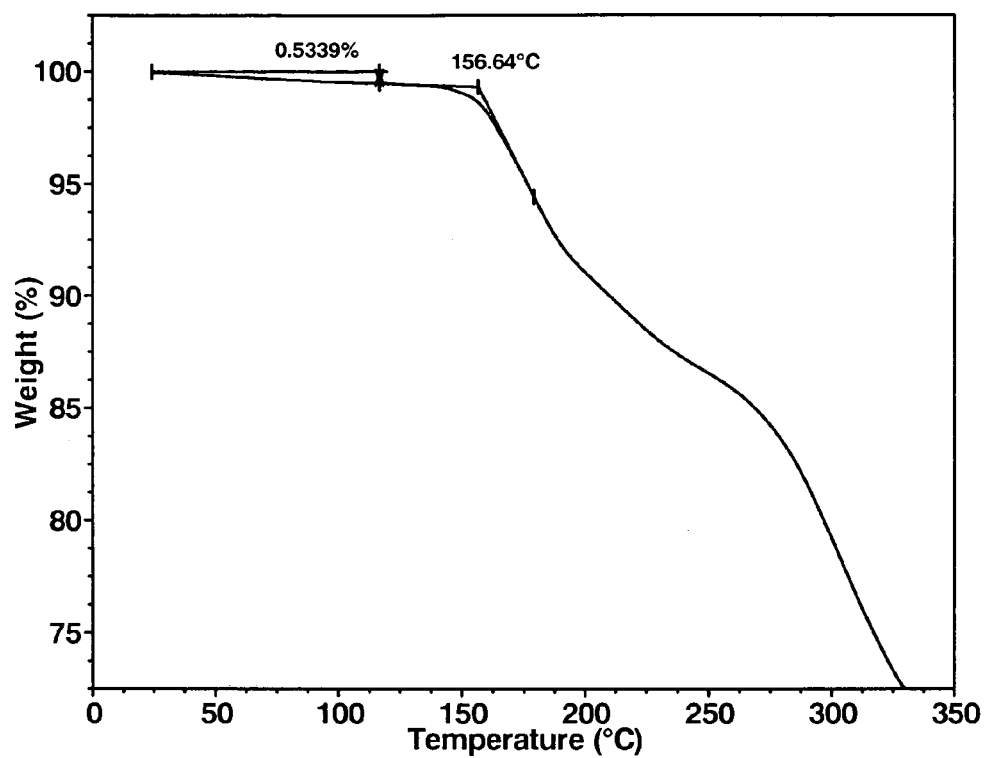
FIG. 33 shows a thermogravimetric analysis (TGA) of Compound I Maleate Form I.

The DSC thermogram shows a sharp endotherm with onset at about 152° C. (FIG. 32). The TGA shows about 0.5% weight loss below about 120° C. (FIG. 33). The $^1$H NMR spectrum is consistent with the structure with approximately 1:1 ratio of Compound I:maleic acid. High humidity stress test at 75% RH/RT did not show any evidence of deliquescence.

3.1.6 Compound I Mesylate Form I 58.5 mg Compound I was slurried with 2 mL acetonitrile at approximately 60° C. Then, 8.5 µL methanesulfonic acid (1 molar equivalent) and 11.5 µL acetonitrile were combined and added to the Compound I mixture. The sample immediately clarified. The solution was allowed to cool to ambient temperature with stirring. The sample volume was reduced by approximately half and the sample was subjected to probe sonication. The resulting solids were collected by vacuum filtration and dried under ambient conditions. The XRPD pattern of these solids is presented in FIG. 34.

Figure 35:
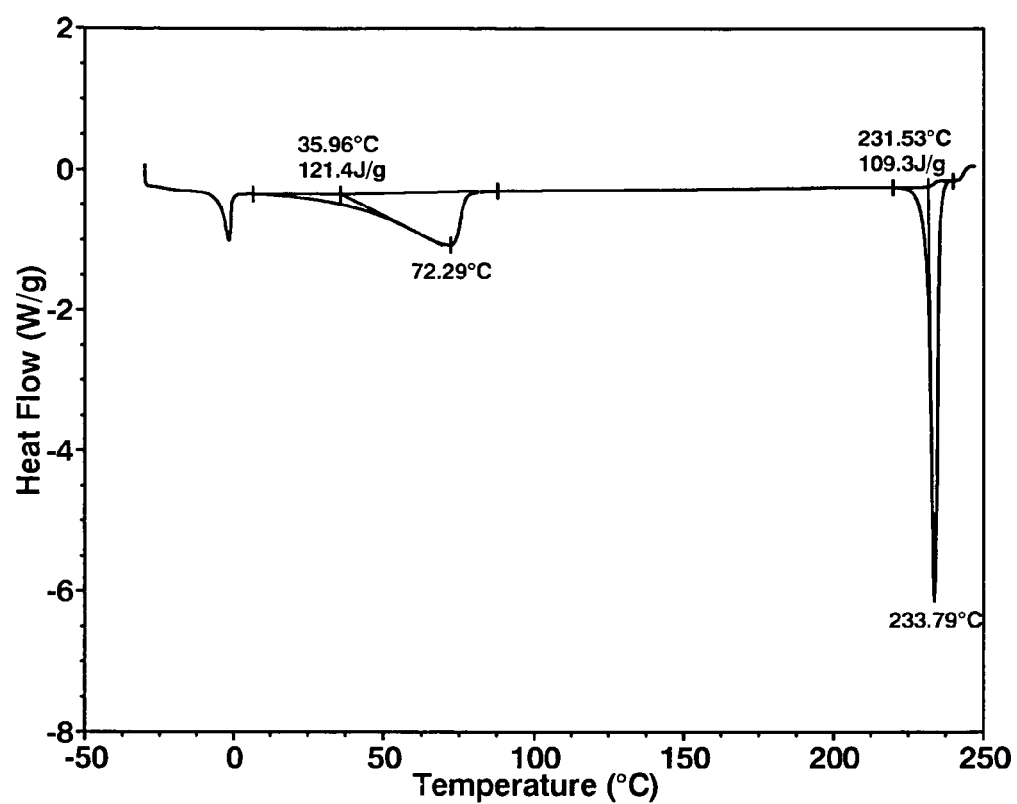
FIG. 35 shows a differential scanning calorimeter (DSC) curve of Compound I Mesylate Form I.
Figure 36:
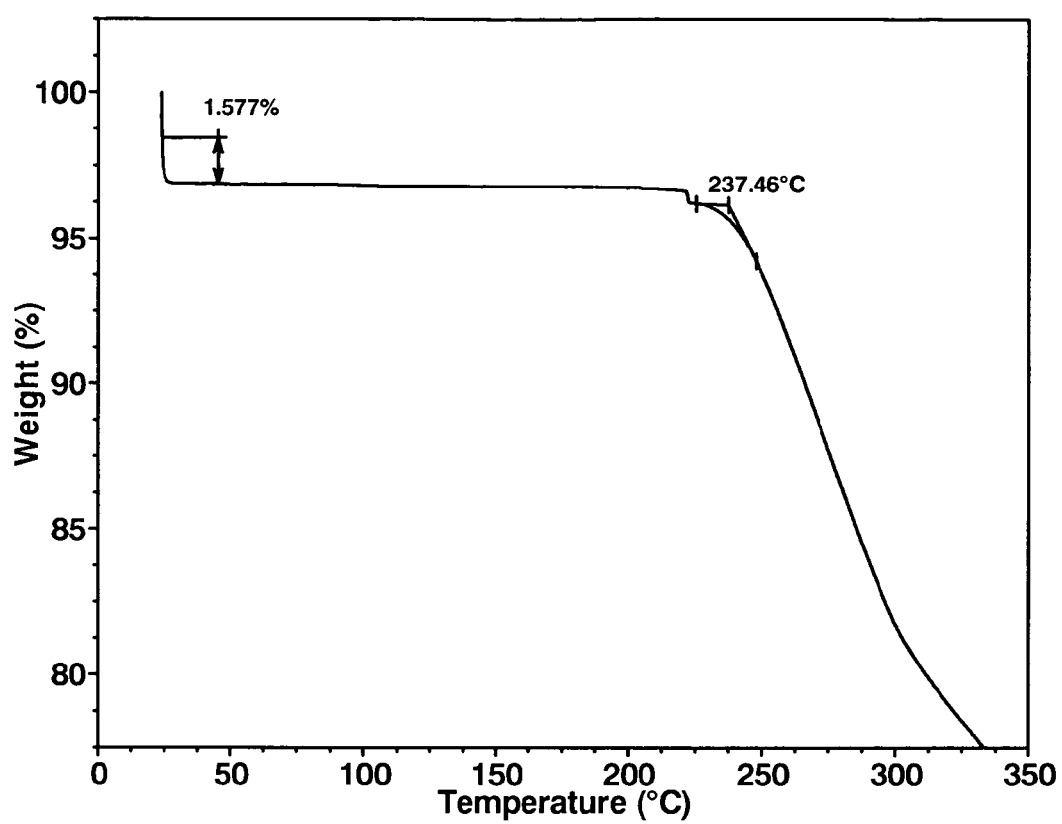
FIG. 36 shows a thermogravimetric analysis (TGA) of Compound I Mesylate Form I.

The DSC thermogram shows a small endotherm below 0° C., a broad endotherm below about 100° C. and another sharp endotherm with onset at about 232° C. (FIG. 35). The TGA shows about 1.6% weight loss below about 50° C. (FIG. 36). $^1$H NMR spectrum is consistent with the structure with 1:1 ratio of Compound I:methanesulfonic acid and a small amount of residual EtOH. High humidity stress test at 75% RH/RT did not show any evidence of deliquescence.

3.1.7 Compound I Oxalate Form I 69.5 mg Compound I was slurried with 0.75 mL ethanol at approximately 60° C. Then, 14.2 mg oxalic acid (1 molar equivalent) was slowly added to the mixture (solids persisted). The sample was left at elevated temperature for approximately 2 hours and then allowed to cool to ambient temperature in uncontrolled fashion with stirring. The solids were collected by vacuum filtration and left to dry under ambient conditions. The XRPD pattern of the resulting solids is presented in FIG. 37.

Figure 38:
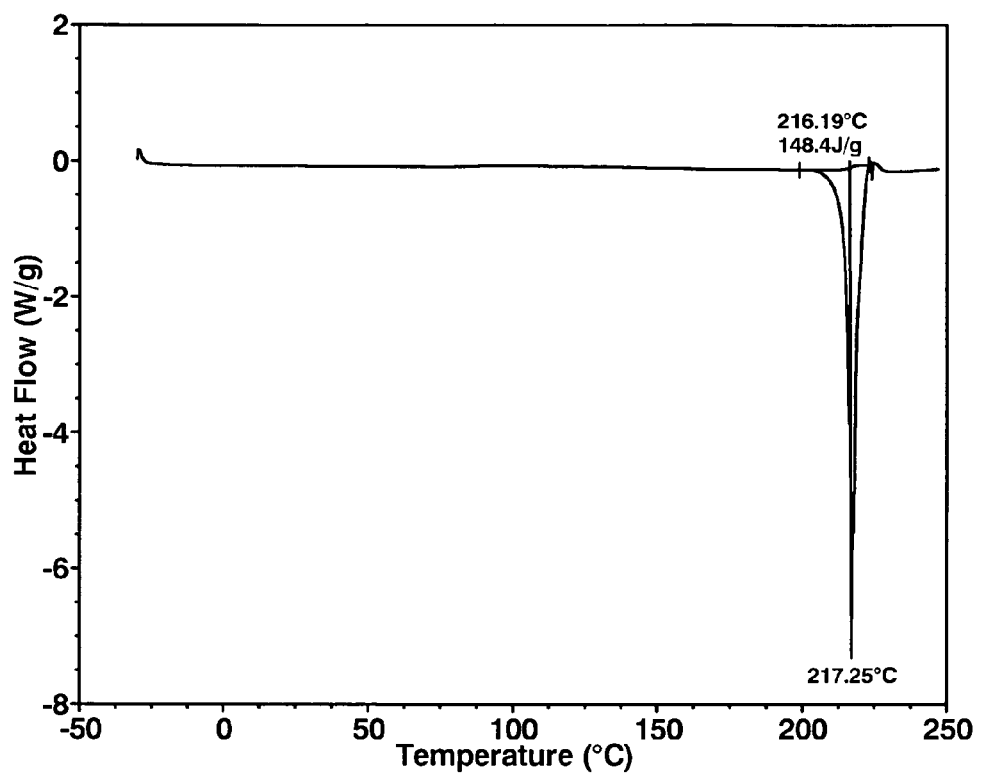
FIG. 38 shows a differential scanning calorimeter (DSC) curve of Compound I Oxalate Form I.
Figure 39:
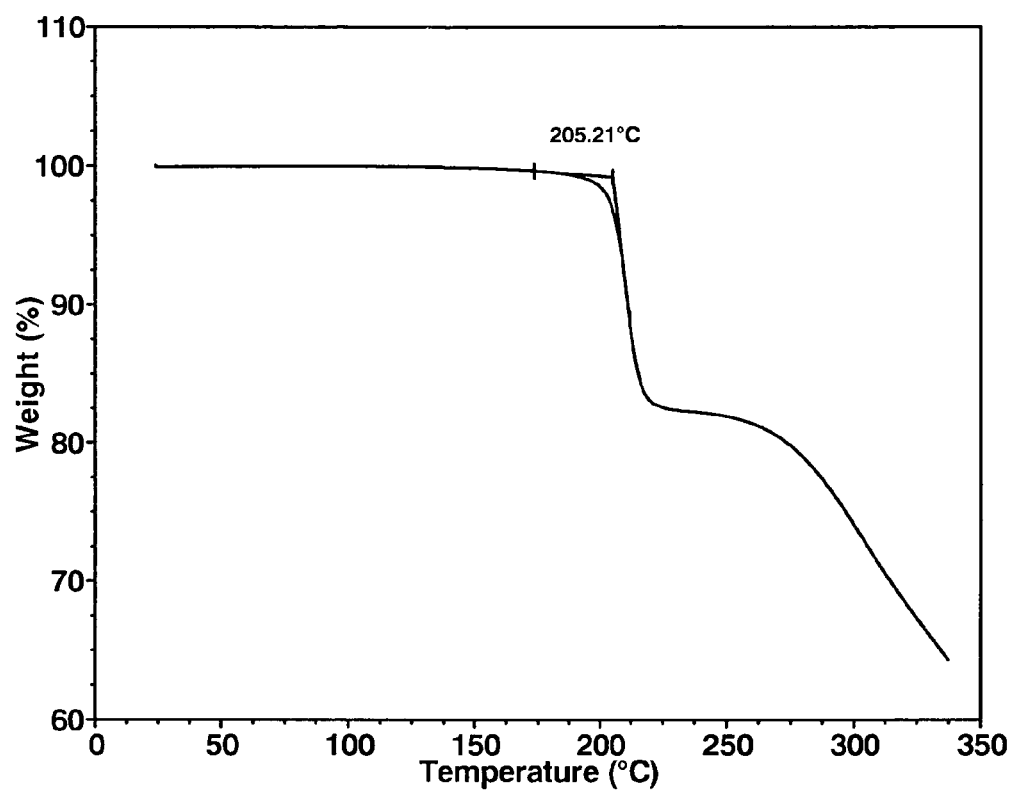
FIG. 39 shows a thermogravimetric analysis (TGA) of Compound I Oxalate Form I.

The DSC thermogram shows a single sharp endotherm with onset at about 216° C. (FIG. 38). The TGA shows no weight loss below about 150° C. (FIG. 39). The $^1$H NMR spectrum is consistent with the structure with trace amount of residual EtOH. High humidity stress test at 75% RH/RT did not show any evidence of deliquescence.

Figure 40:
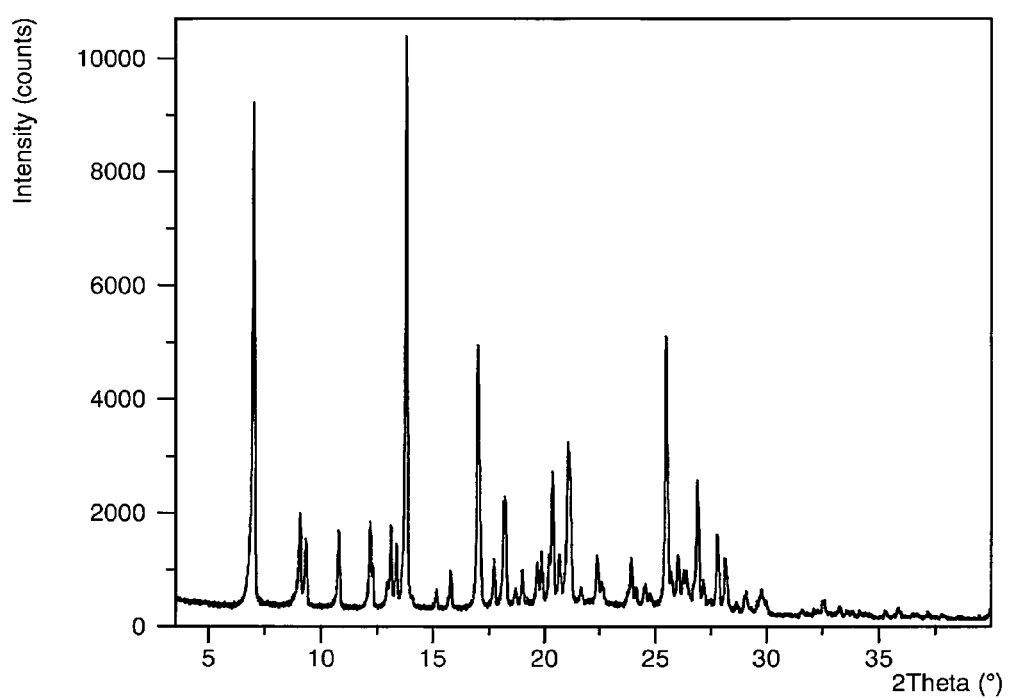
FIG. 40 shows an X-ray powder diffraction (XRPD) of Compound I Sulfate Form I.

3.1.8 Compound I Sulfate Form I 41.6 mg Compound I was dissolved in 400 µL dichloromethane at approximately 45° C. The sample solution was combined with 7.3 mg sulfuric acid and then allowed to cool to ambient temperature with stirring. The resulting solution was evaporated to dryness then slurried with 100 µL acetonitrile under ambient conditions. The resulting solids were collected by vacuum filtration and left to dry under ambient conditions and analyzed by XRPD (FIG. 40). The $^1$H NMR spectrum is consistent with the structure of Compound I. IC analysis confirmed salt formation with approximately 1:1 ratio of Compound I:sulfuric acid. High humidity stress test at 75% RH/RT did not show any evidence of deliquescence.

Figure 52:
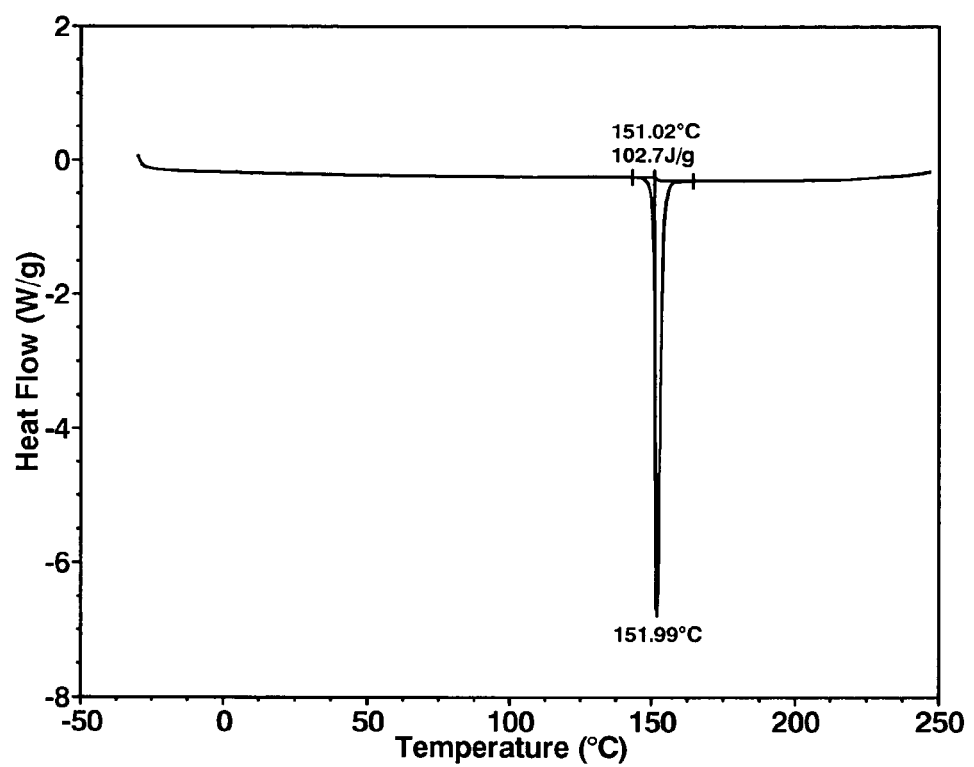
FIG. 52 shows a differential scanning calorimeter (DSC) curve of Compound I Adipate Form I.
Figure 53:
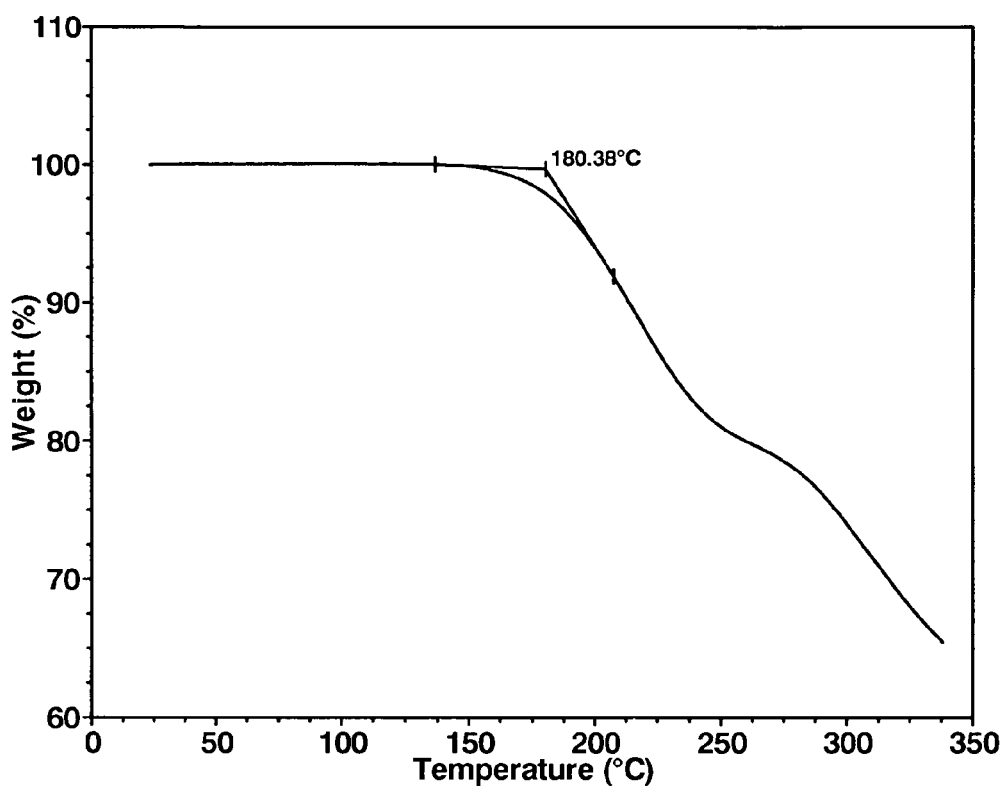
FIG. 53 shows a thermogravimetric analysis (TGA) of Compound I Adipate Form I.

3.1.9 Compound I Adipate Form I 104.3 mg of Compound I was slurried in 1 mL acetonitrile. The sample was stirred at approximately 40° C. (solids persisted). Then, adipic acid (34.4 mg, 1 molar equivalent) was added to the stirred mixture and the mixture was warmed and stirred overnight. The cloudy solution was then moved to an ambient temperature stirrer and agitated for three days. The resulting solids were collected by vacuum filtration, dried under ambient conditions and analyzed by XRPD, DSC, TGA and NMR. The XRPD pattern is presented in FIG. 51. The DSC trace showed a single endotherm with an onset at about 151° C. (FIG. 52). No weight loss was observed by TGA prior to decomposition (FIG. 53). $^1$H NMR showed a 1:1 ratio of Compound I:adipic acid.

Figure 54:
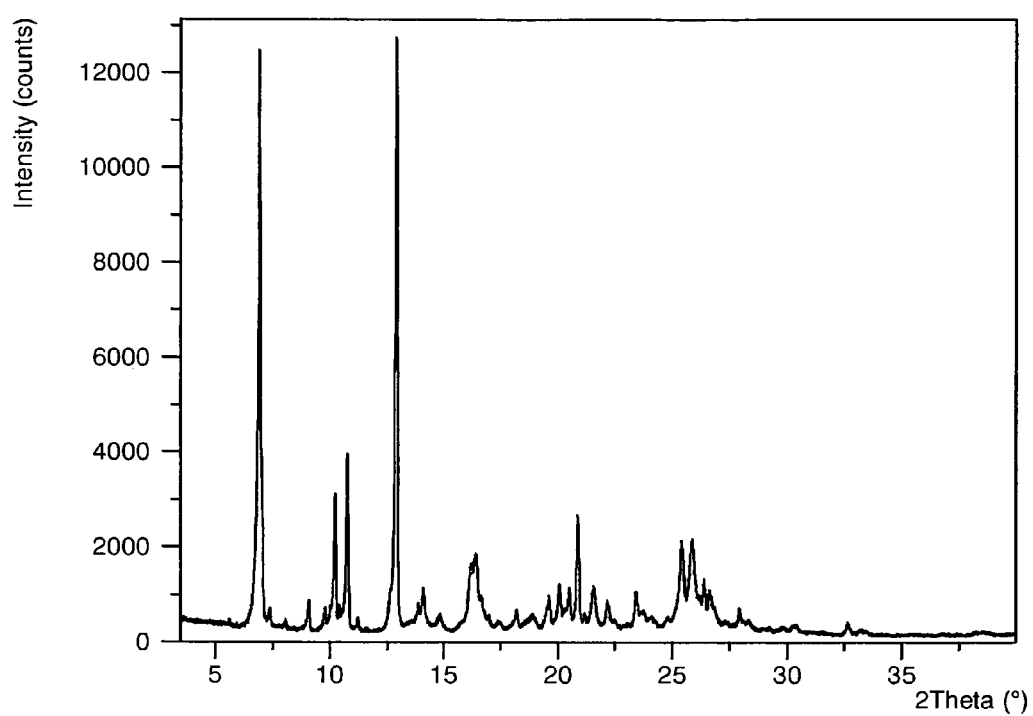
FIG. 54 shows an X-ray powder diffraction (XRPD) of Compound I Besylate Form I.

3.1.10 Compound I Besylate Form I 56.6 mg of Compound I was slurried in 1 mL ethanol at approximately 60° C. (solids persisted). Benzenesulfonic acid (21.2 mg, 1.06 molar equivalents) was then charged to the solution, and the solution immediately clarified. The sample was stirred and allowed to cool to ambient temperature. No solids were generated, so the solution was allowed to evaporate to dryness. XRPD analysis of the solids is shown in FIG. 54, and the $^1$H NMR spectrum showed less than a 1:1 Compound I:salt ratio.

Figure 56:
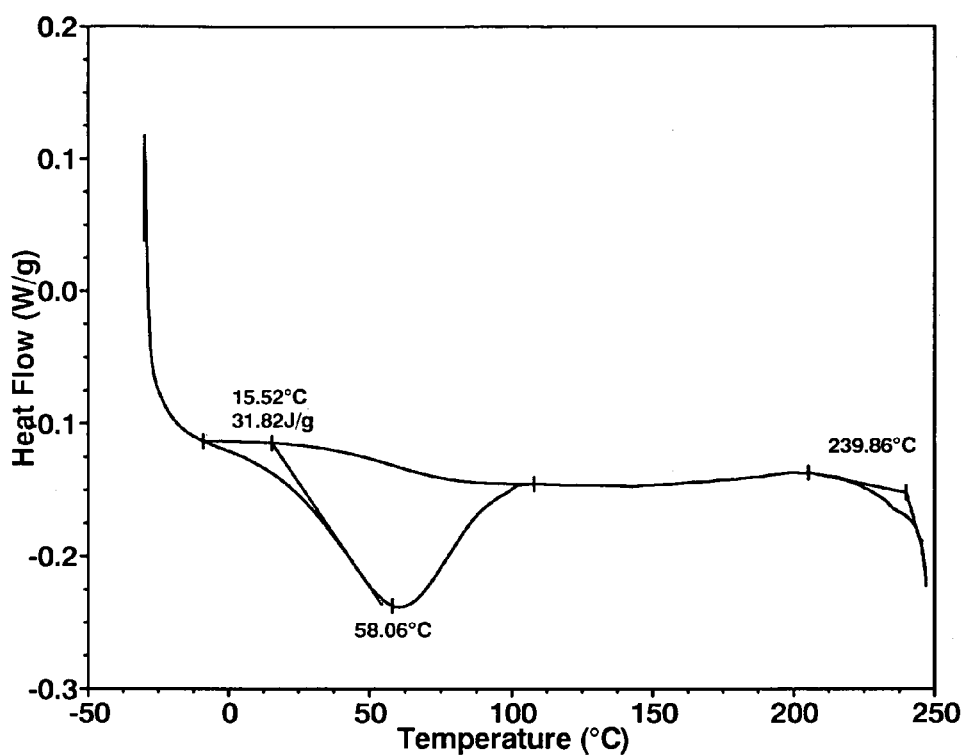
FIG. 56 shows a differential scanning calorimeter (DSC) curve of Compound I Edisylate Form I.
Figure 57:
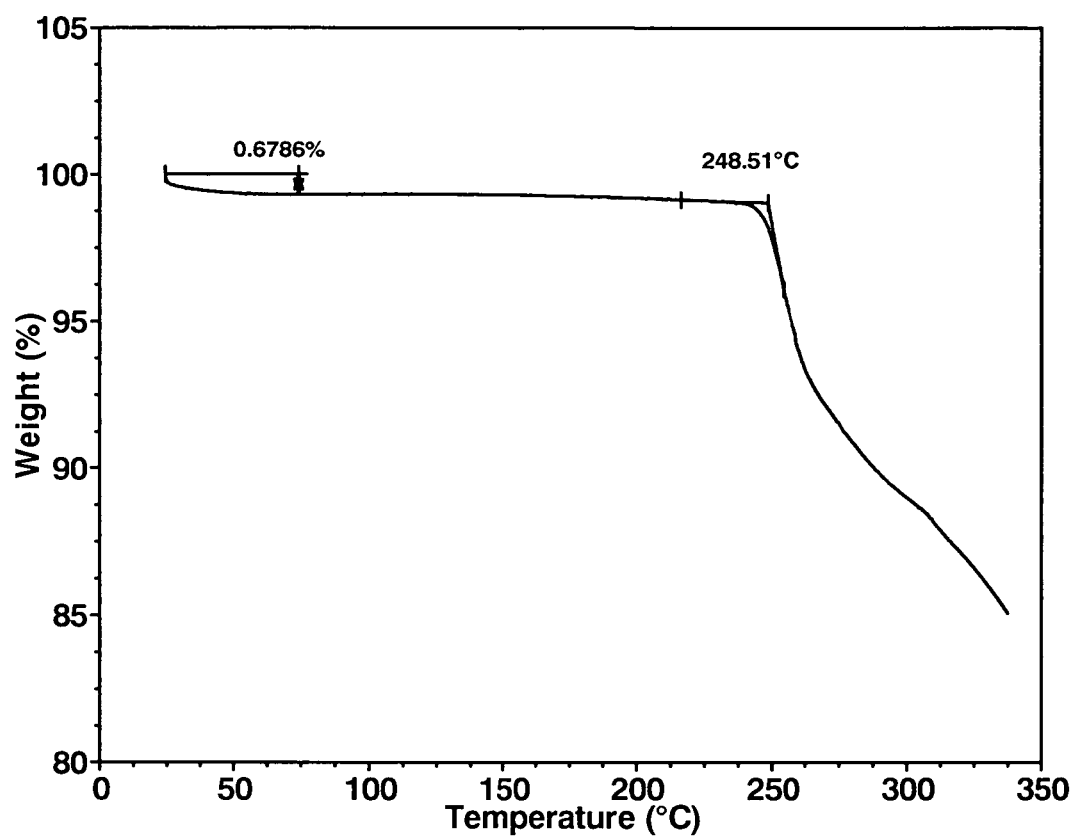
FIG. 57 shows a thermogravimetric analysis (TGA) of Compound I Edisylate Form I.

3.1.11 Compound I Edisylate Form I 58.9 mg of Compound I was slurried in 1 mL ethanol at approximately 60° C. (solids persisted). Then, 1,2-ethanedisulfonic acid (30.1 mg, 1.2 molar equivalents) was charged to the mixture, and the sample clarified. The solution was maintained at 60° C. with stirring for approximately 1 hour before allowing it to cool to ambient temperature with stirring. No solids resulted, so the solution was left to evaporate to dryness. XRPD pattern of the resulting material is presented in FIG. 55. The DSC trace shows a broad endotherm below 100° C. (onset at about 15° C.) followed by melt with decomposition with onset at about 240° C. (FIG. 56). TGA shows 0.7% weight loss below 70° C. (FIG. 57). The $^1$H NMR spectrum is consistent with the structure with approximately 1:1 ratio of Compound I:acid and a trace amount of the residual ethanol. High humidity stress test at 75% RH/RT did not show any evidence of deliquescence.

Figure 59:
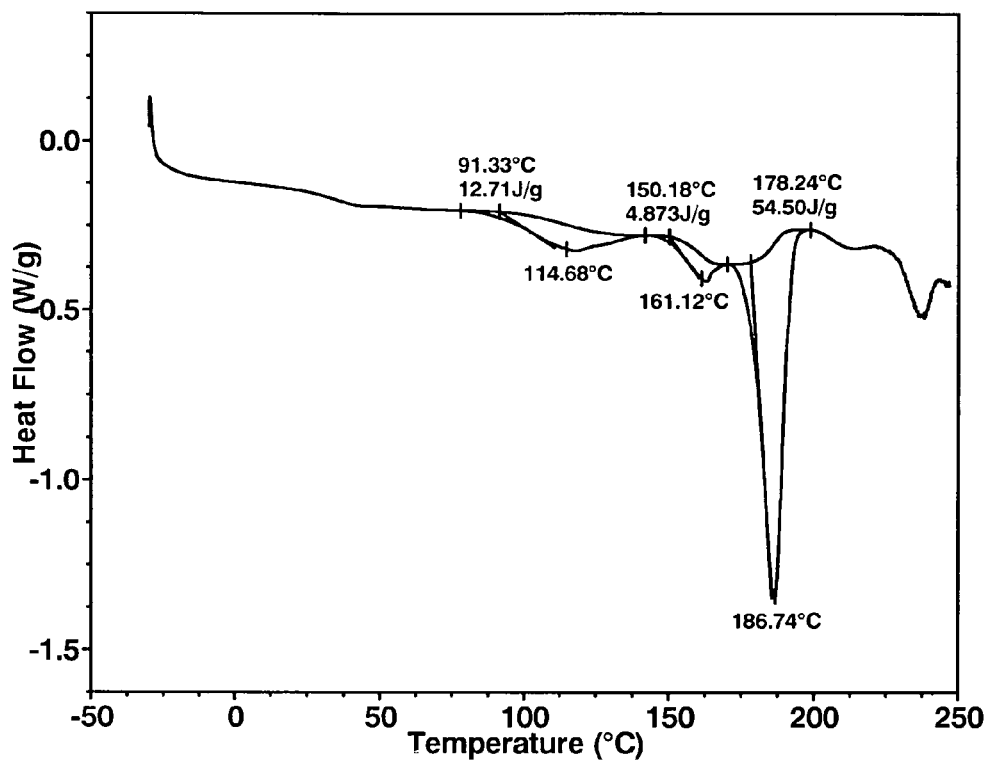
FIG. 59 shows a differential scanning calorimeter (DSC) curve of Compound I Edisylate Form II.
Figure 60:
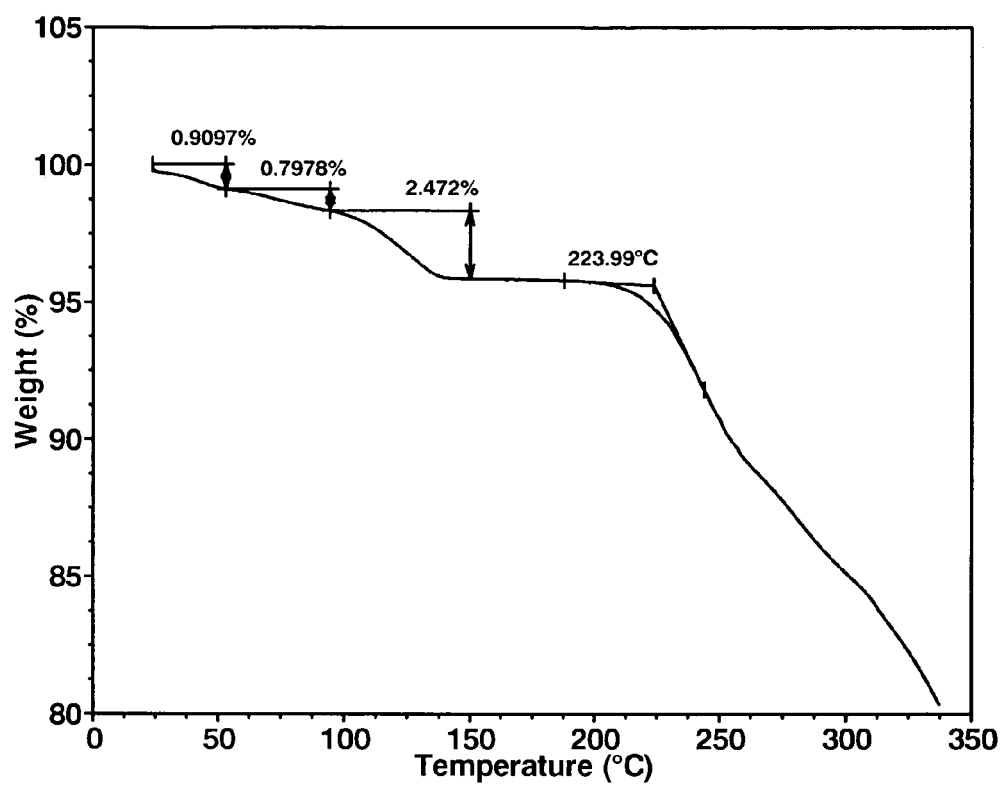
FIG. 60 shows a thermogravimetric analysis (TGA) of Compound I Edisylate Form II.

3.1.12 Compound I Edisylate Form II 91.1 mg of Compound I was slurried with 0.75 mL ethanol at approximately 60° C. Then, 1,2-ethanedisulfonic acid (49.2 mg, 1.26 molar equivalents) was slowly added to the mixture, and the sample clarified. The sample was left at 60° C. with stirring for approximately 2 hours before allowing to cool to ambient temperature with stirring. The resulting solids were collected by vacuum filtration and dried under ambient conditions. The obtained solids afforded XRPD pattern (FIG. 58) different from Compound I Edisylate Form I. DSC shows multiple weak broad endotherms with onsets at about 91 and about 150° C. followed by melt with onset at about 178° C. (FIG. 59). TGA also shows three steps of 0.9, 0.8 and 2.5% weight losses below 150° C. (FIG. 60). $^1$H NMR spectrum is consistent with the structure with approximately 1:1 ratio of Compound I:acid and trace of residual ethanol.

3.1.13 Compound I Gentisate Form I

Figure 61:
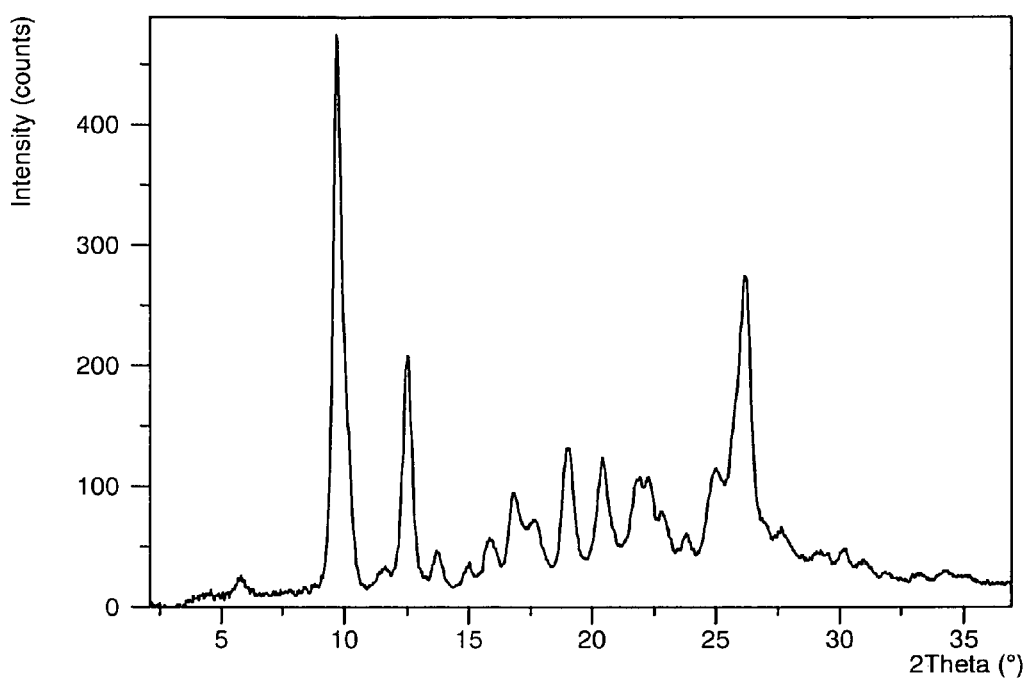
FIG. 61 shows an X-ray powder diffraction (XRPD) of Compound I Gentisate Form I.

A standard ethanol/Compound I solution was prepared and 0.005 mmol Compound I was placed into each well of a 96-well plate. The ethanol was removed via evaporation, and 1 equivalent of gentisic acid (in either an ethanol of ethanol/water solution) was added to the wells. The well plates were covered with Silverseal® and warmed on a hot plate. After a period of time at elevated temperature, the heating source was shut off and the samples were slowly cooled to ambient temperature. The Silverseal® was removed and the solvent was allowed to evaporate under ambient conditions. The XRPD pattern of Compound I Gentisate Form I is shown in FIG. 61.

Figure 63:
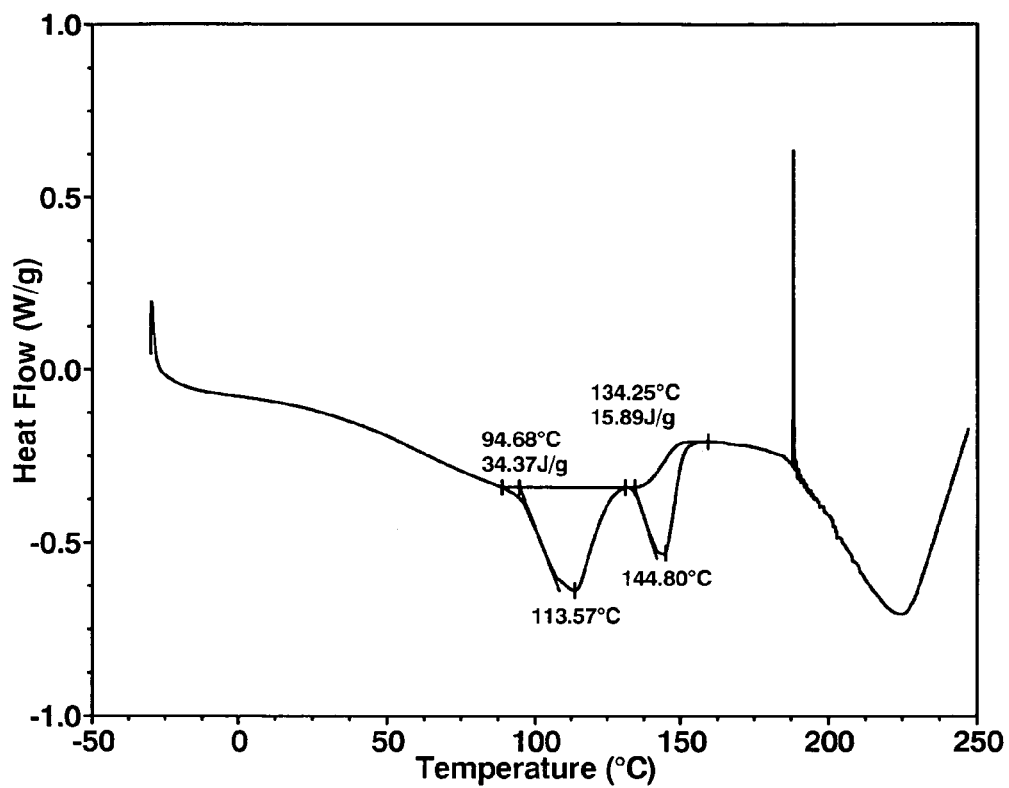
FIG. 63 shows a differential scanning calorimeter (DSC) curve of Compound I Gentisate Form II.
Figure 64:
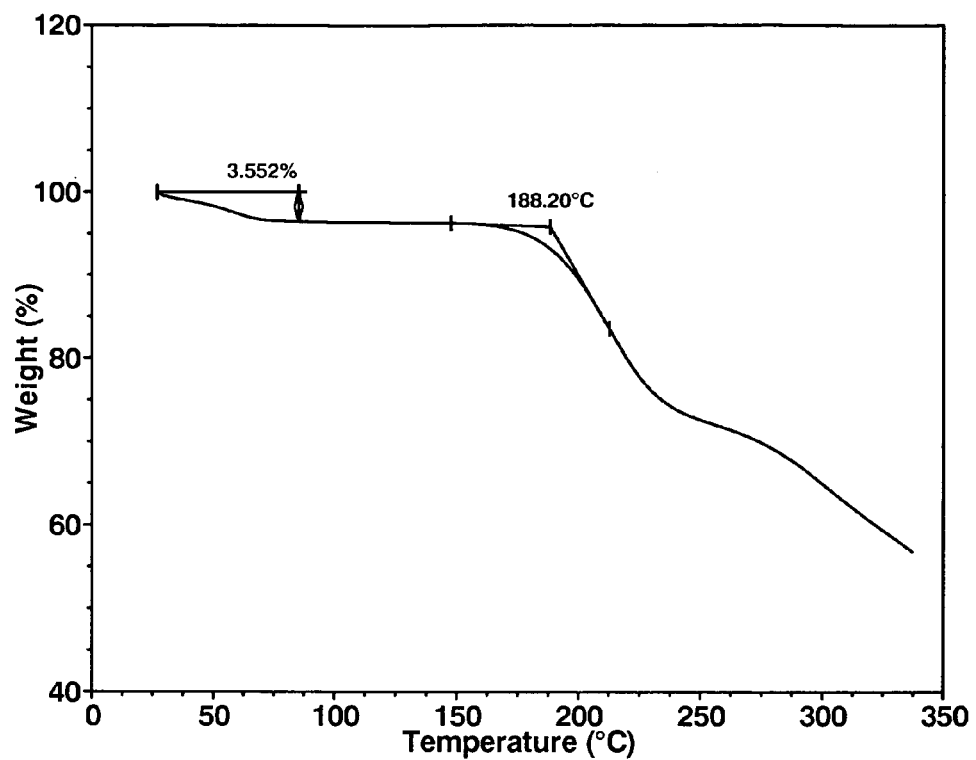
FIG. 64 shows a thermogravimetric analysis (TGA) of Compound I Gentisate Form II.

3.1.14 Compound I Gentisate Form II 76.5 mg of Compound I was stirred with 0.75 mL ethanol at approximately 60° C. Then, gentisic acid (25.2 mg, 1 molar equivalent) was added to the cloudy solution. The solution immediately clarified. The sample was stirred at elevated temperature for approximately 2 hours and was then slowly cooled to the ambient temperature with stirring. The solids were collected by vacuum filtration and dried under ambient conditions. The obtained solids afforded a different XRPD pattern (FIG. 62) compared to Compound I Gentisate Form I. The DSC thermogram shows two broad endotherms with onsets at about 95 and about 134° C. (FIG. 63). The TGA shows 3.6% weight loss below 80° C. (FIG. 64). The $^1$H NMR spectrum is consistent with the structure with approximately 1:1 ratio of Compound I:acid and some residual ethanol. High humidity stress test at 75% RH/RT did not show any evidence of deliquescence.

Figure 65:
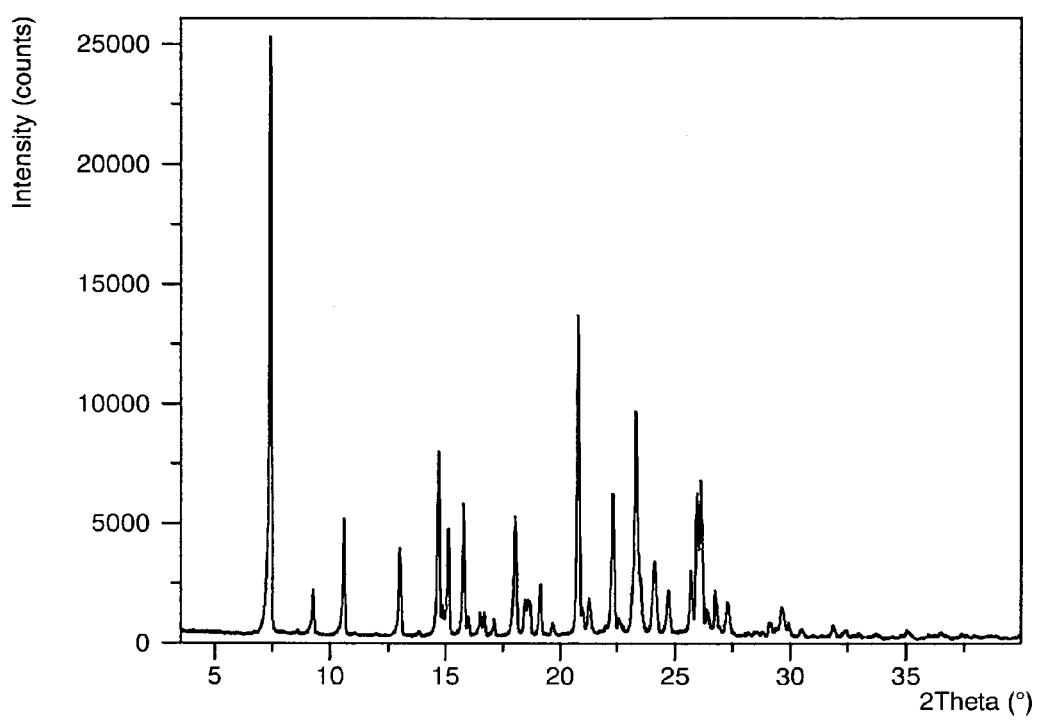
FIG. 65 shows an X-ray powder diffraction (XRPD) of Compound I Glutarate Form I.

3.1.15 Compound I Glutarate Form I 24.9 mg of Compound I was stirred in 550 μL dichloromethane. Glutaric acid (8.0 mg, 1.08 molar equivalents) was dissolved in 40 μL of acetone and charged to the Compound I solution. The sample was dried, then slurried with 200 μL diethyl ether and allowed to evaporate to dryness. The resulting solids afforded a crystalline XRPD pattern (FIG. 65).

Figure 66:
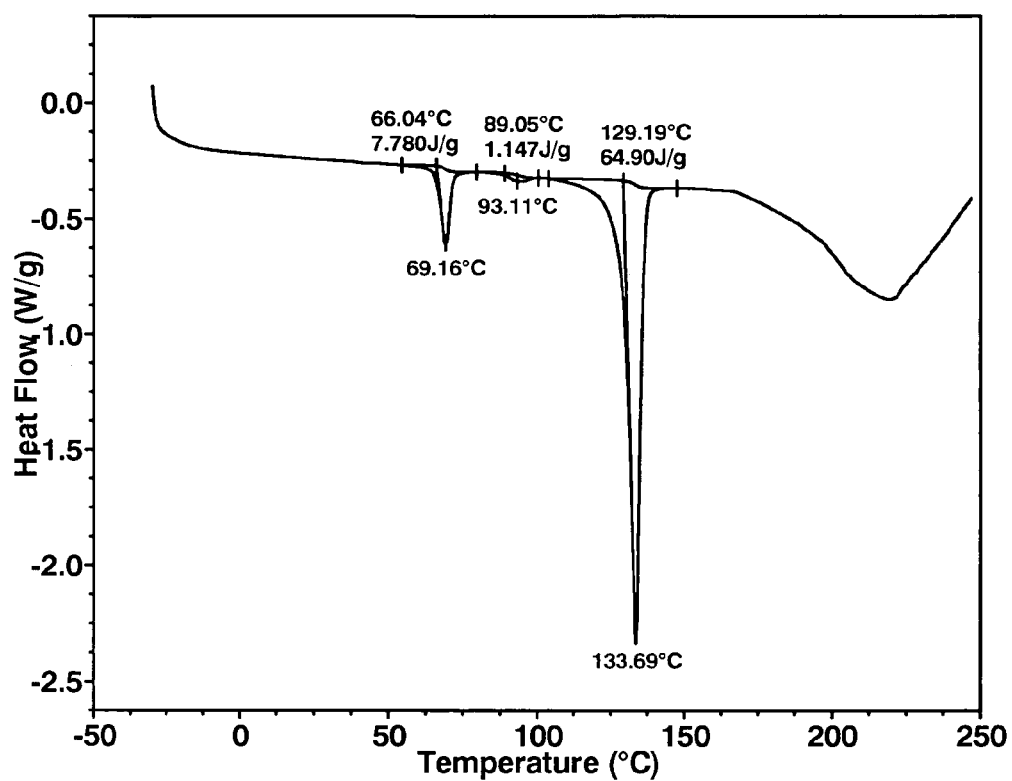
FIG. 66 shows a differential scanning calorimeter (DSC) curve of Compound I Glutarate Form I.
Figure 67:
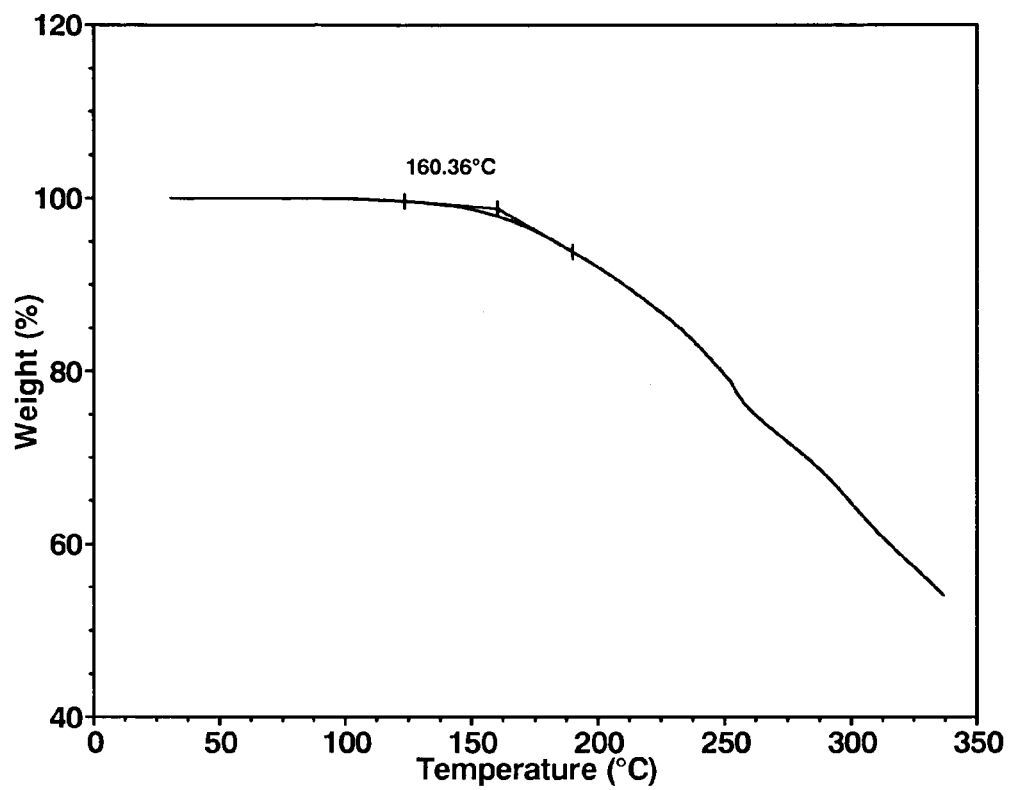
FIG. 67 shows a thermogravimetric analysis (TGA) of Compound I Glutarate Form I.

The DSC thermogram shows a small endotherm with onset at about 66° C., a weak broad endotherm with onset at about 89° C., and a melt with onset at about 129° C. (FIG. 66). The TGA spectrum does not show weight loss below the decomposition at 160° C. (FIG. 67). $^1$H NMR spectrum is consistent with the structure with about a 1:1.2 ratio of Compound I:glutaric acid. High humidity stress test at 75% RH/RT did not show any evidence of deliquescence.

3.1.16 Compound I Glutarate Form II 78.5 mg of Compound I was slurried in 0.75 mL ethanol at approximately 60° C. Then, glutaric acid (50.0 mg, 2 molar equivalents) was slowly added to the mixture, and the sample clarified. The sample was allowed to cool to ambient temperature with stirring. No solids were generated. The sample volume was carefully reduced in vacuo, which resulted in a clear glass. The sample was dried completely and slurried in 400 μL acetonitrile. The resulting solids were collected by vacuum filtration and allowed to dry under ambient conditions. The obtained solids afforded a unique XRPD pattern (FIG. 68) compared to Compound I Glutarate Form I.

Figure 69:
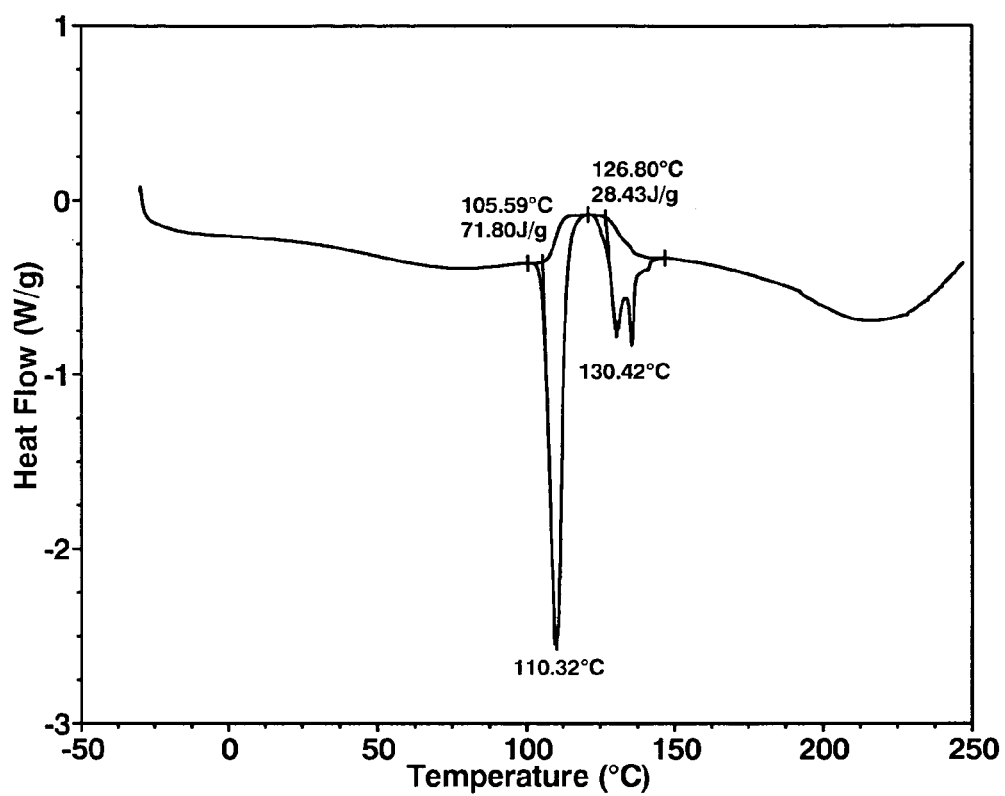
FIG. 69 shows a differential scanning calorimeter (DSC) curve of Compound I Glutarate Form II.
Figure 70:
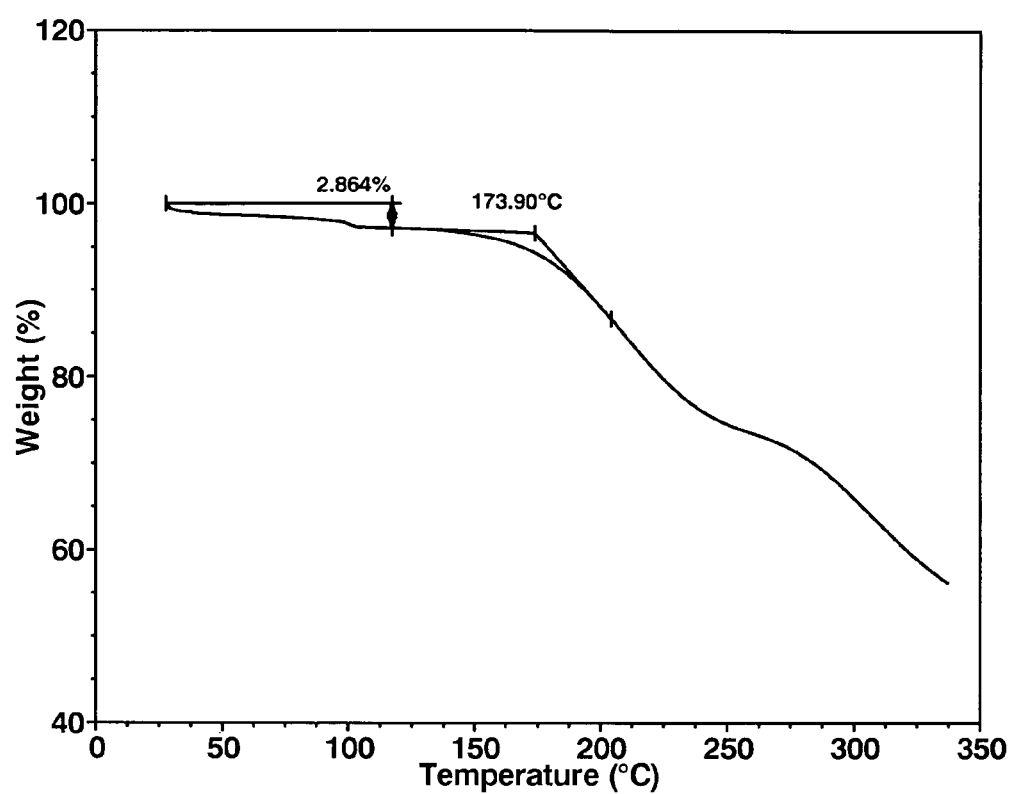
FIG. 70 shows a thermogravimetric analysis (TGA) of Compound I Glutarate Form II.

The DSC thermogram shows a weak broad endotherm below 100° C., followed by a sharp endotherm with onset at about 106° C. and another endotherm with onset at about 127° C. (FIG. 69). The TGA spectrum shows 2.9% weight loss below 120° C. (FIG. 70). The $^1$H NMR spectrum is consistent with the structure with a 1:1 ratio of Compound I:acid. High humidity stress test at 75% RH/RT did not show any evidence of deliquescence.

3.1.17 Compound I L-Tartrate Form I 47.6 mg of Compound I was slurried with 1 mL ethanol at approximately 60° C. Then, L-tartaric acid (16.8 mg, 1.05 molar equivalents) was added and the sample immediately clarified. The sample was allowed to cool to ambient temperature in uncontrolled fashion with stirring. No solids were generated. Sample was then evaporated to dryness. The XRPD pattern of the residual solids is presented in FIG. 71.

Figure 72:
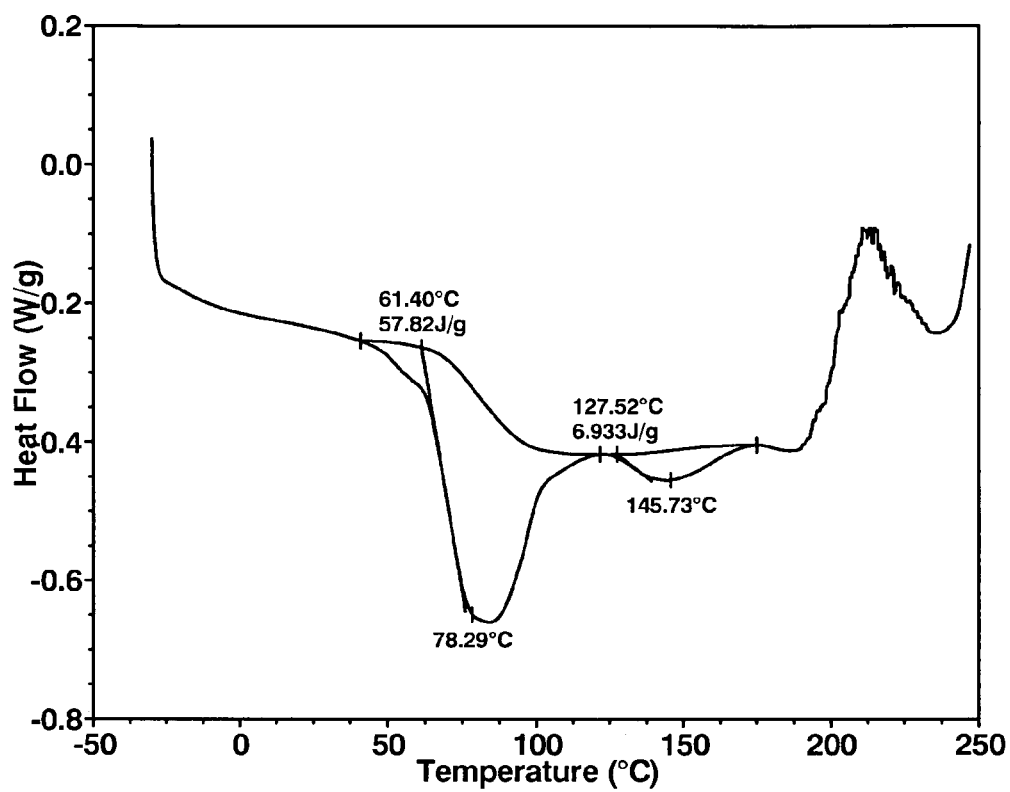
FIG. 72 shows a differential scanning calorimeter (DSC) curve of Compound I L-Tartrate Form I.
Figure 73:
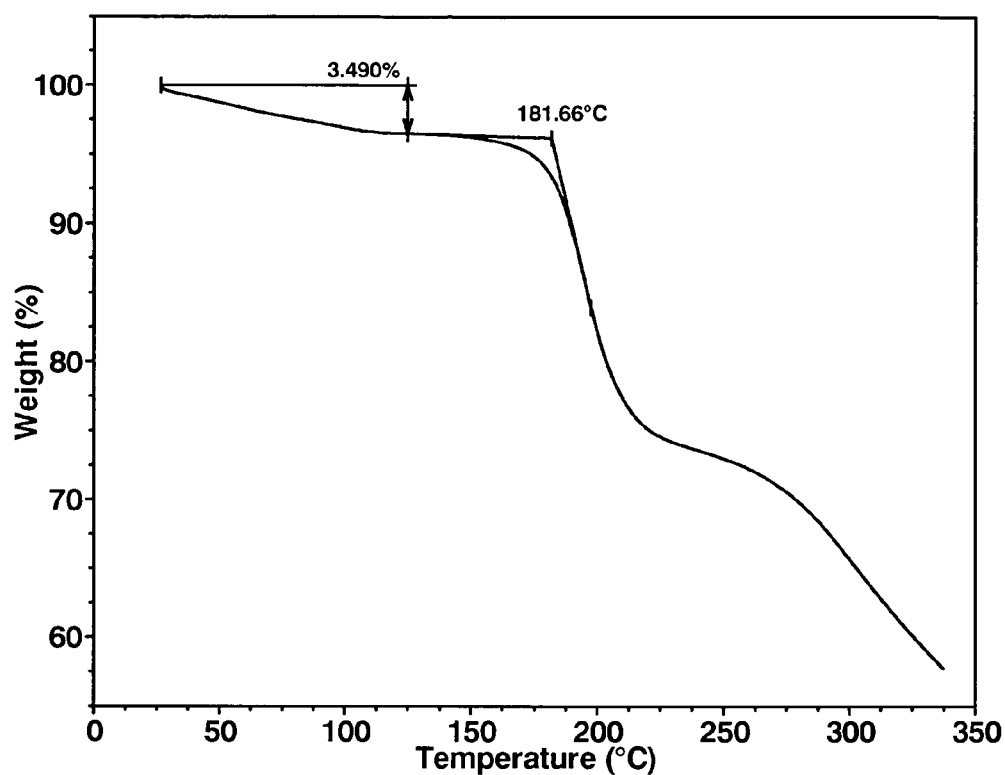
FIG. 73 shows a thermogravimetric analysis (TGA) of Compound I L-Tartrate Form I.

The DSC thermogram shows a broad endotherm with onset at about 61° C. and another small broad endotherm with onset at about 128° C. (FIG. 72). The TGA shows 3.5% weight loss below 120° C. (FIG. 73). The $^1$H NMR spectrum is consistent with the structure with 1:1 ratio of Compound I:acid and trace residual EtOH present. High humidity stress test at 75% RH/RT did not show any evidence of deliquescence.

Figure 74:
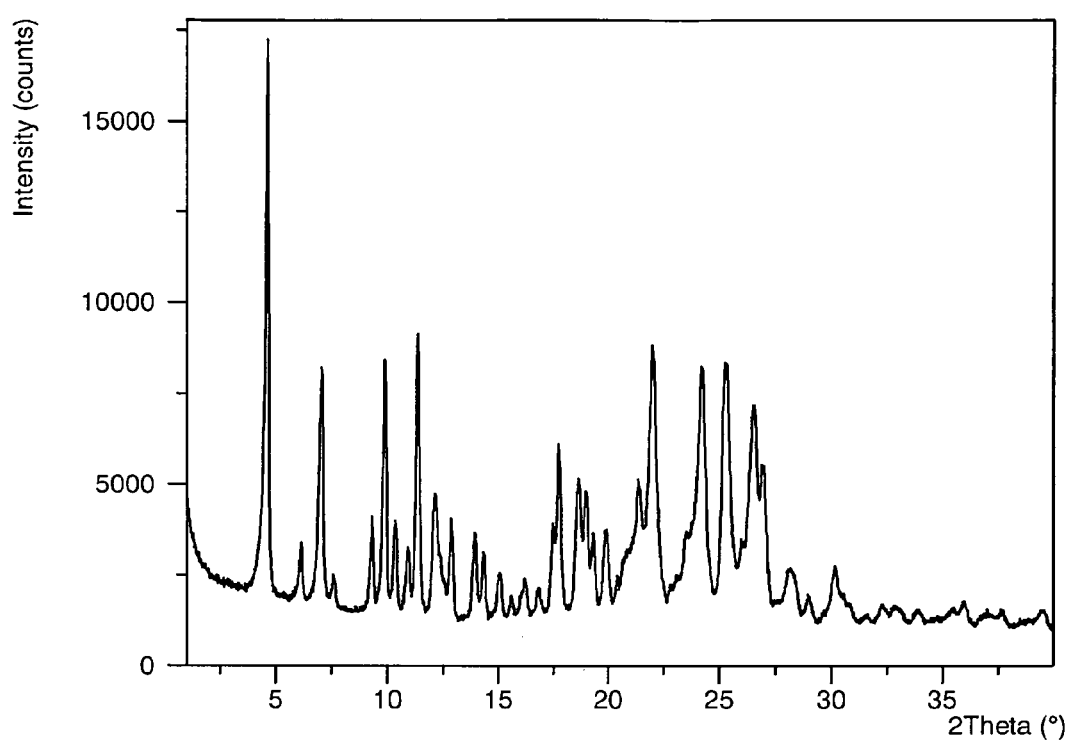
FIG. 74 shows an X-ray powder diffraction (XRPD) of Compound I L-Tartrate Form II.

3.1.18 Compound I L-Tartrate Form II 77.7 mg of Compound I was slurried with 0.5 mL ethanol at approximately 60° C. Then, L-tartaric acid (26.4 mg, 1.01 molar equivalents) was slowly added. The mixture was stirred at elevated temperature for approximately 2 hours. The solution was then allowed to cool to ambient temperature with stirring. No solids resulted, so the sample was evaporated to dryness and then slurried in 2 mL diethyl ether at ambient temperature. Solids were collected by vacuum filtration and left to dry under ambient conditions. The obtained solids afforded a unique XRPD pattern (FIG. 74).

Figure 75:
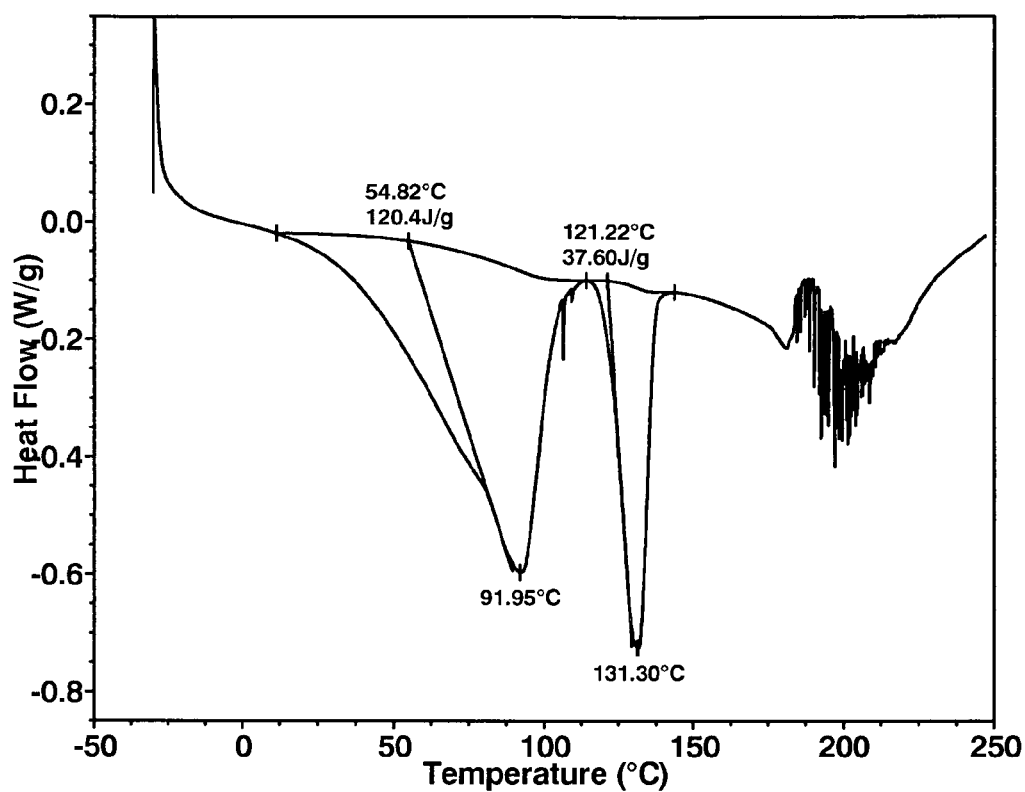
FIG. 75 shows a differential scanning calorimeter (DSC) curve of Compound I L-Tartrate Form II.
Figure 76:
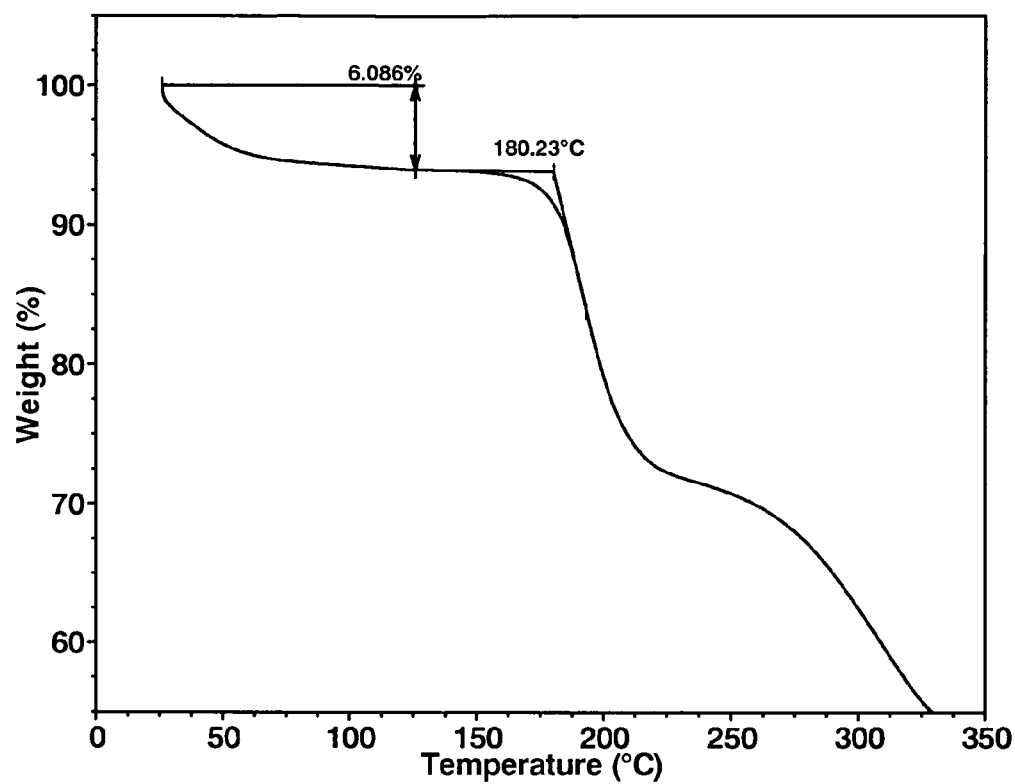
FIG. 76 shows a thermogravimetric analysis (TGA) of Compound I L-Tartrate Form II.

The DSC thermogram shows broad endotherm below 110° C. (with onset at about 55° C.) and another sharp endotherm with onset at about 121° C. (FIG. 75). The TGA shows 6.1% weight loss below 120° C. (FIG. 76). The $^1$H NMR spectrum is consistent with the structure with 1:1 ratio of Compound I:acid and trace residual EtOH present. High humidity stress test at 75% RH/RT did not show any evidence of deliquescence.

3.1.19 Compound I Propyl Gallate Form I 110.3 mg of Compound I was dissolved in 1 mL ethanol at approximately 60° C. The sample was stirred. Propyl gallate (57.3 mg, 1.09 molar equivalents) was dissolved in 0.5 mL ethanol. The solutions were combined at elevated temperature and stirred for approximately 5 minutes. The solution was then allowed to cool to ambient temperature with stirring. The resulting solids were collected by vacuum filtration and dried under ambient conditions. XRPD pattern is presented in FIG. 77.

Figure 78:
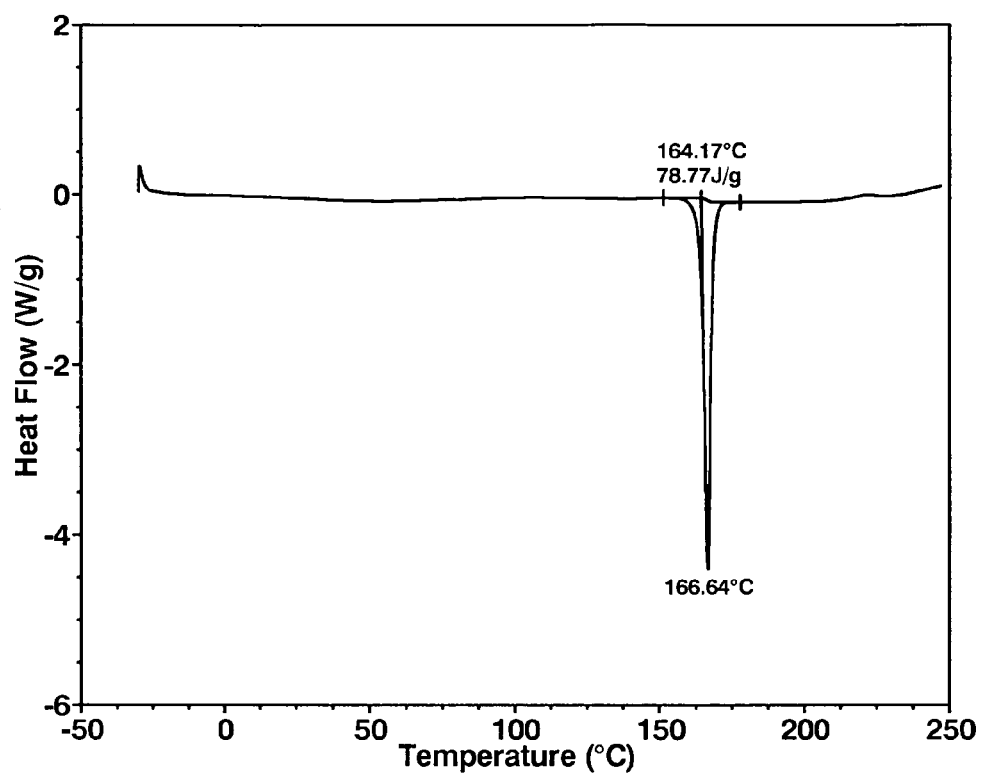
FIG. 78 shows a differential scanning calorimeter (DSC) curve of Compound I Propyl Gallate Form I.
Figure 79:
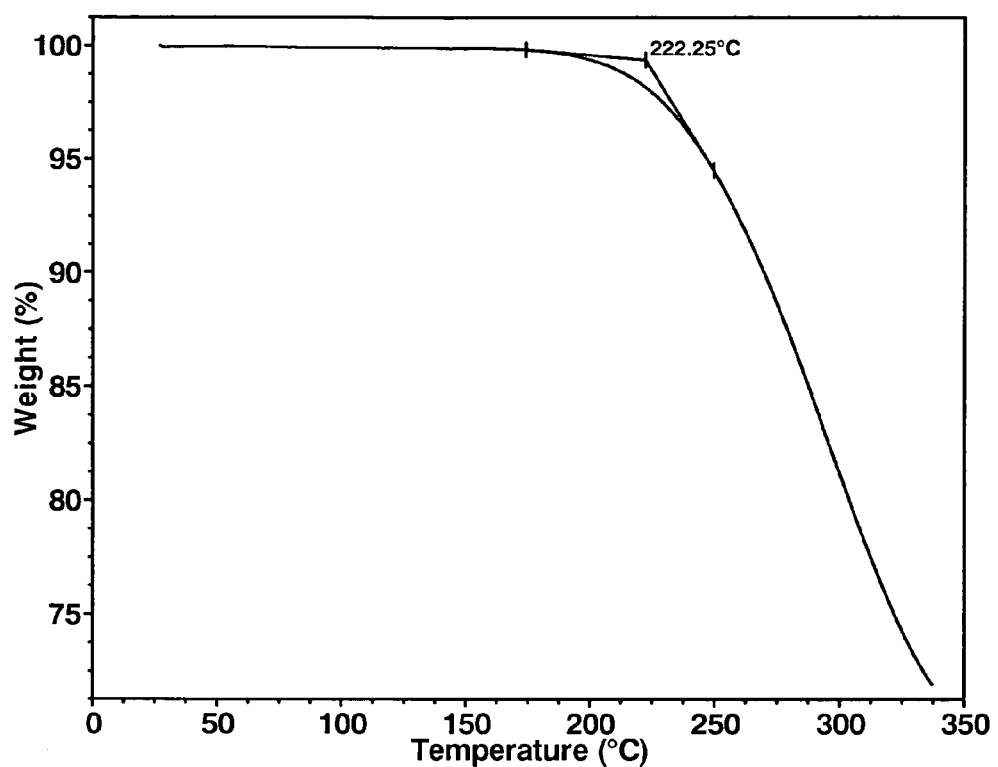
FIG. 79 shows a thermogravimetric analysis (TGA) of Compound I Propyl Gallate Form I.

The DSC thermogram shows weak broad endotherm below 100° C. and sharp endotherm with onset at about 164° C. (FIG. 78). The TGA shows 0.1% weight loss below 100° C. (FIG. 79). The $^1$H NMR spectrum is consistent with the structure with about a 1:1.5 ratio of Compound I:co-former. High humidity stress test at 75% RH/RT did not show any evidence of deliquescence.

3.1.20 Compound I Succinate Form I 106.4 mg of Compound I was slurried with 1 mL acetonitrile. The sample was slurried at approximately 40° C. Succinic acid (27.8 mg, 1 molar equivalent) was added to the solution. Solids persisted in solution. The sample was left overnight at elevated temperature. The sample was moved to an ambient temperature stirrer and left for three days. The solids were collected by vacuum filtration and left to dry under ambient conditions. The XRPD pattern is presented in FIG. 80.

Figure 81:
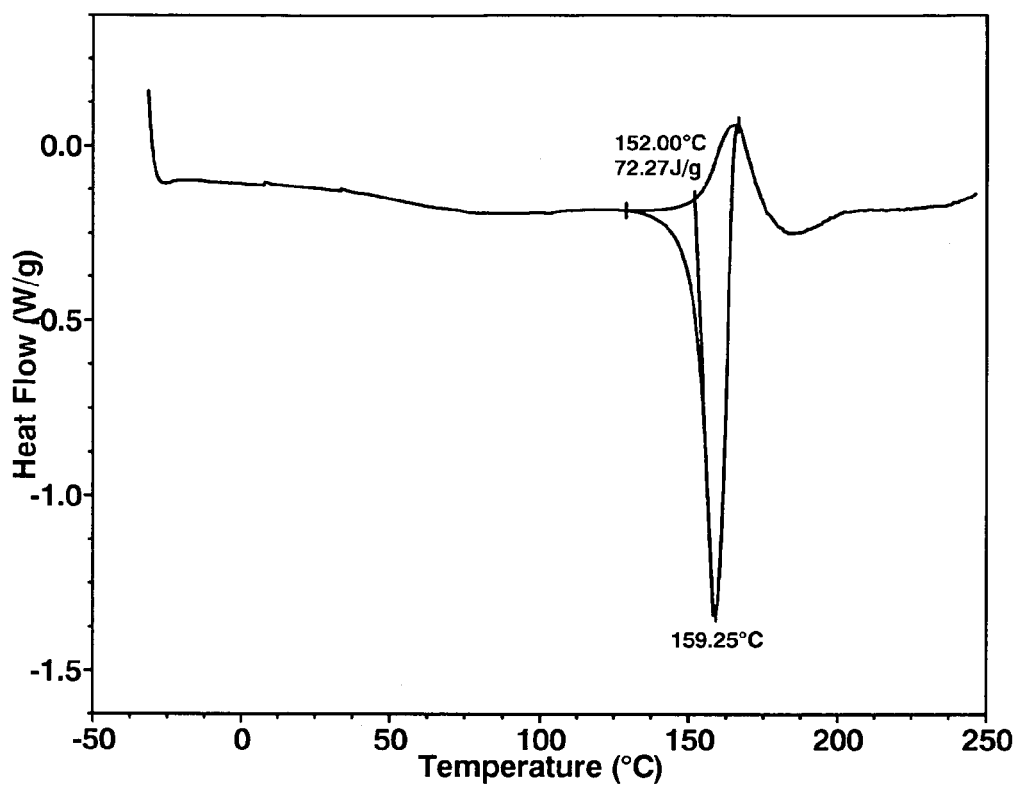
FIG. 81 shows a differential scanning calorimeter (DSC) curve of Compound I Succinate Form I.
Figure 82:
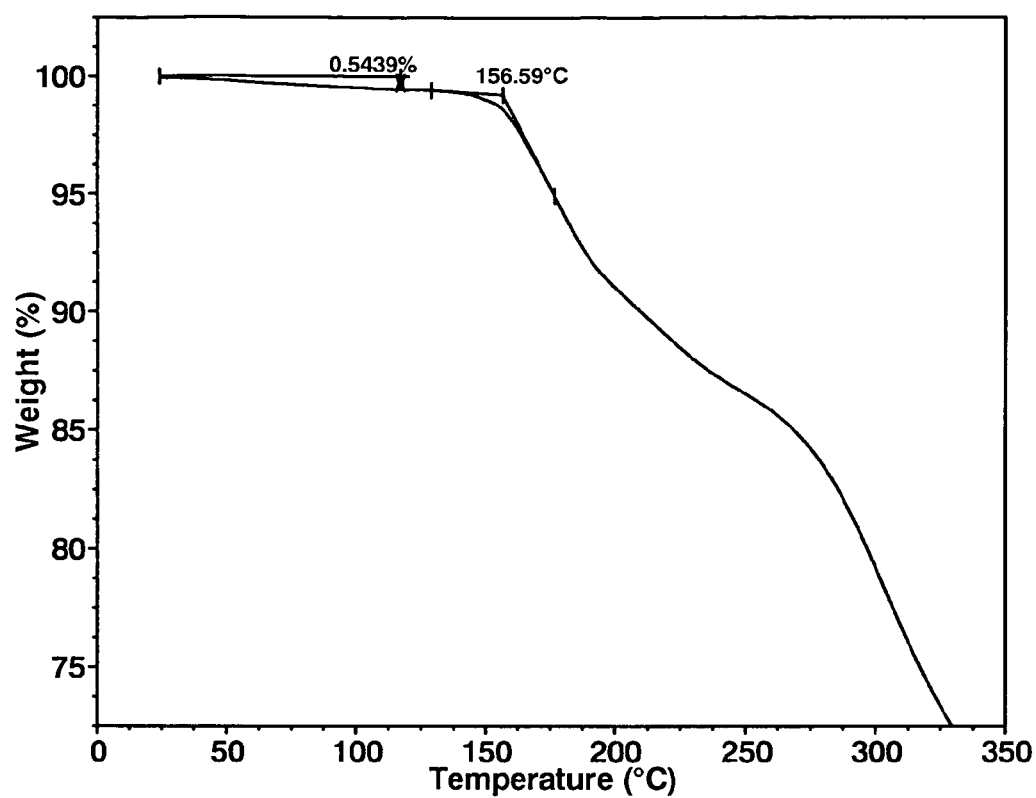
FIG. 82 shows a thermogravimetric analysis (TGA) of Compound I Succinate Form I.

The DSC thermogram shows a weak broad endotherm below about 120° C., followed by an endotherm with onset at about 152° C. (FIG. 81). The TGA shows 0.5% weight loss below 120° C. (FIG. 82). The $^1$H NMR spectrum is consistent with the structure with 1:1 ratio of Compound I:acid with a trace amount of residual EtOH. High humidity stress test at 75% RH/RT did not show any evidence of deliquescence.

3.1.21 Compound I Tosylate Form I 48.3 mg of Compound I was slurried in 1 mL ethanol at approximately 60° C. p-Toluenesulfonic acid (21.3 mg, 1.14 molar equivalents) was slowly added to the mixture, and a solution resulted. The sample was slowly cooled to ambient temperature with stirring. No solids were generated. The sample was reduced in volume until solids were generated. Solids collected by vacuum filtration and allowed to dry under ambient conditions. XRPD pattern is presented in FIG. 83.

Figure 84:
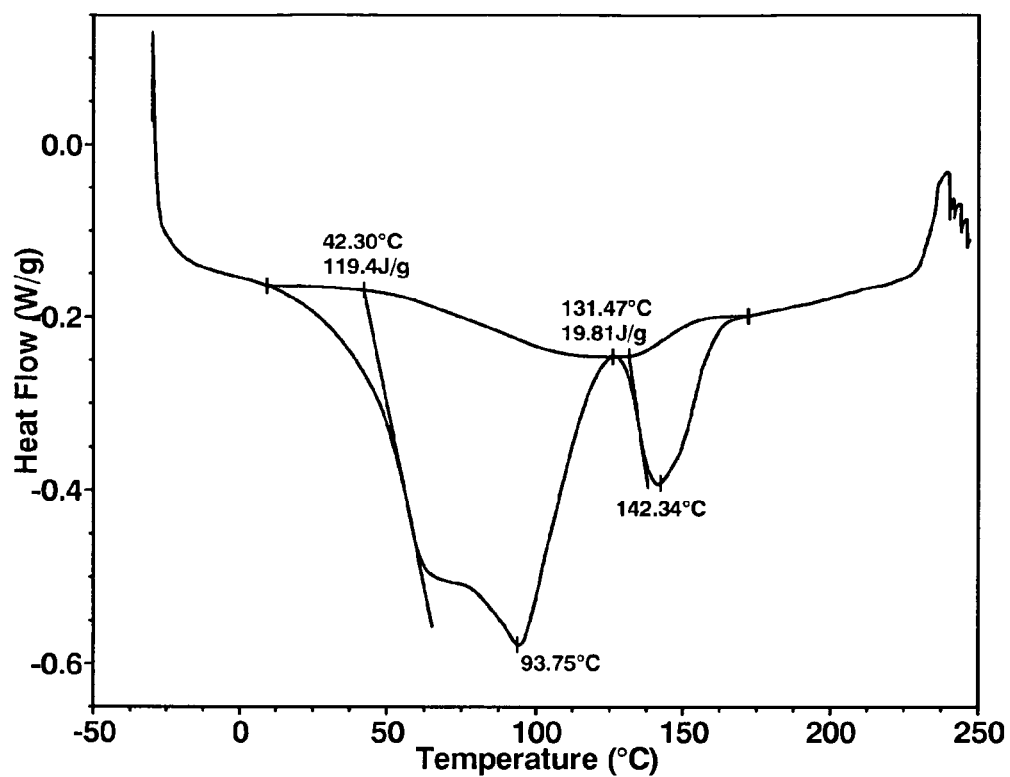
FIG. 84 shows a differential scanning calorimeter (DSC) curve of Compound I Tosylate Form I.
Figure 85:
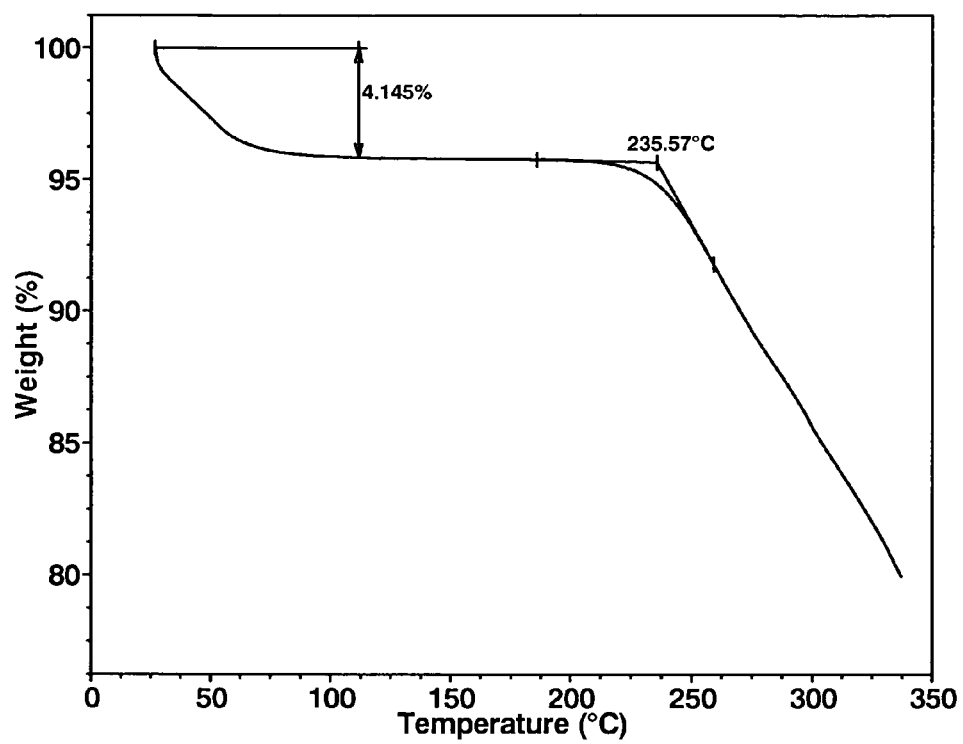
FIG. 85 shows a thermogravimetric analysis (TGA) of Compound I Tosylate Form I.

The DSC thermogram shows a wide broad endotherm below 120° C., followed by an endotherm with onset at about 131° C. (FIG. 84). The TGA shows 4.1% weight loss below 100° C. (FIG. 85). $^1$H NMR spectrum was consistent with the structure with 1:1 ratio of Compound I:acid and 0.5 equivalents of residual EtOH present. High humidity stress test at 75% RH/RT did not show any evidence of deliquescence.

4.1 Compound I for Alcoholic Hepatitis

Hepatic p-p38 expression in alcoholic liver biopsies was quantified based on immunohistochemistry using a rabbit monoclonal antibody against human p-p38. Thresholds for low, medium and high staining and the percentage of cells within each category were determined. Staining intensity was expressed as a Histologic Score (HS) that considers the distribution and intensity of staining (range, 0 to 300). Liver biopsies were also graded according to the Alcoholic Hepatitis Histologic Score (AHHS). Correlations between the intensity of p-p38 expression and clinical and histologic characteristics in alcoholic hepatitis were determined, and compared with patients with NASH (n=60) and primary sclerosing cholangitis (PSC, n=105).

Liver biopsies from 9 alcoholic hepatitis patients were studied (median age, 42 years; 45% male; median Model for End-Stage Liver Disease (MELD), 24 (IQR 23-27); 44% with bridging fibrosis or cirrhosis; and two deaths, 22%). All alcoholic hepatitis biopsies were p-p38-immunoreactive (median HS, 124; range 100154); significantly greater than those observed in patients with non-alcoholic steatohepatitis (13.4 [IQR 4.3-30.3]) and PSC (54.1 [27.1-76.9]; both P<0.001). In alcoholic hepatitis, p-p38 was detected multifocally in hepatocyte clusters. Hepatocyte p-p38 expression was diffusely cytoplasmic and/or strongly nuclear. In ballooned hepatocytes, p-p38 was localized to cytoplasmic aggregates consistent with Mallory bodies. Inflammatory infiltrates staining positive for p-p38 were predominantly macrophages; polymorphonuclear neutrophils (PMNs) did not express p-p38. Reactive bile ducts also contained occasional cytoplasmic and/or nuclear p-p38. p-p38 expression was correlated with MELD ($\rho$=0.67; P=0.047) and hematocrit ($\rho$=0.73; P=0.025), and inversely associated with the serum bicarbonate concentration ($\rho$=−0.69; P=0.038), but not other standard laboratory parameters. p-p38 expression was higher in hepatocellular than canalicular or ductular bilirubinostasis (median HS; 133.5 vs. 103; P=0.020). However, p-p38 staining intensity was not associated with the total AHHS or other histologic variables.

The results show that hepatic expression of p-p38 is correlated with MELD and other markers of alcoholic hepatitis severity, suggesting that ASK1 inhibition may have therapeutic benefit in patients with this disease.

We claim:

1. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form I) characterized by an X-ray powder diffractogram comprising the following peaks: 16.7, 21.3, and 22.8°2θ±0.2°2θ, as determined on a diffractometer using Cu-Kα radiation at a wavelength of 1.5406 Å.

2. Compound I Form I according to claim 1, wherein the diffractogram further comprises peaks at 8.9, 10.0, 13.9, and 29.0°2θ±0.2°2θ.

3. Compound I Form I according to claim 1, wherein the diffractogram is substantially as shown in FIG. 1.

4. Compound I Form I according to claim 1, characterized by a differential scanning calorimetry (DSC) curve that comprises an endotherm at about 202° C.

5. Compound I Form I according to claim 1, wherein the DSC curve is substantially as shown in FIG. 2.

6. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form II) characterized by an X-ray powder diffractogram comprising the following peaks: 11.2, 16.6, and 17.4°2θ±0.2°2θ, as determined on a diffractometer using Cu-Kα radiation at a wavelength of 1.5406 Å.

7. Compound I Form II according to claim 6, wherein the diffractogram further comprises peaks at 4.9, 23.7, and 27.4°2θ±0.2°2θ.

8. Compound I Form II according to claim 6, wherein the diffractogram is substantially as shown in FIG. 4.

9. Compound I Form II according to claim 6, characterized by a differential scanning calorimetry (DSC) curve that comprises an endotherm at about 92° C., an endotherm at about 160° C., an exotherm at about 166° C., and endotherm at about 200° C.

10. Compound I Form II according to claim 6, wherein the DSC curve is substantially as shown in FIG. 5.

11. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form III) characterized by an X-ray powder diffractogram comprising the following peaks: 5.1, 10.2, and 25.3°2θ±0.2°2θ, as determined on a diffractometer using Cu-Kα radiation at a wavelength of 1.5406 Å.

12. Compound I Form III according to claim 11, wherein the diffractogram further comprises peaks at 11.4, 18.4, and 21.9°2θ±0.2°2θ.

13. Compound I Form III according to claim 11, wherein the diffractogram is substantially as shown in FIG. 7.

14. Compound I Form III according to claim 11, characterized by a differential scanning calorimetry (DSC) curve that comprises an endotherm at about 92° C., an exotherm at about 150° C., and an endotherm at about 203° C.

15. Compound I Form III according to claim 11, wherein the DSC curve is substantially as shown in FIG. 8.

16. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form IV) characterized by an X-ray powder diffractogram comprising the following peaks: 7.2, 12.6, and 19.3°2θ±0.2°2θ, as determined on a diffractometer using Cu-Kα radiation at a wavelength of 1.5406 Å.

17. Compound I Form IV according to claim 16, wherein the diffractogram further comprises peaks at 13.8, 25.9, and 28.6°2θ±0.2°2θ.

18. Compound I Form IV according to claim 16, wherein the diffractogram is substantially as shown in FIG. 10.

19. Compound I Form IV according to claim 16, characterized by a differential scanning calorimetry (DSC) curve that comprises an endotherm at about 62° C., an endotherm at about 147° C., an exotherm at about 153° C., and endotherm at about 204° C.

20. Compound I Form IV according to claim 16, wherein the DSC curve is substantially as shown in FIG. 11.

21. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form VI) characterized by an X-ray powder diffractogram comprising the following peaks: 8.8, 23.2, and 23.5°2θ±0.2°2θ, as determined on a diffractometer using Cu-Kα radiation at a wavelength of 1.5406 Å.

22. Compound I Form VI according to claim 21, wherein the diffractogram further comprises peaks at 10.3, 15.2, 18.6, and 28.8°2θ±0.2°2θ.

23. Compound I Form VI according to claim 21, wherein the diffractogram is substantially as shown in FIG. 16.

24. Compound I Form VI according to claim 21, characterized by a differential scanning calorimetry (DSC) curve that comprises an endotherm at about 202° C.

25. Compound I Form VI according to claim 21, wherein the DSC curve is substantially as shown in FIG. 17.

26. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form VII) characterized by an X-ray powder diffractogram comprising the following peaks: 8.2, 14.2, and 22.9°2θ±0.2° 2θ, as determined on a diffractometer using Cu-Kα radiation at a wavelength of 1.5406 Å.

27. Compound I Form VII according to claim 26, wherein the diffractogram further comprises peaks at 18.0 and 21.7°2θ±0.2°2θ.

28. Compound I Form VII according to claim 26, wherein the diffractogram is substantially as shown in FIG. 41.

29. Compound I Form VII according to claim 26, characterized by a differential scanning calorimetry (DSC) curve that comprises an endotherm at about 202° C.

30. Compound I Form VII according to claim 29 characterized by a differential scanning calorimetry (DSC) curve that further comprises an endotherm at about 147° C.

31. Compound I Form VII according to claim 26, wherein the DSC curve is substantially shown as in FIG. 42.

32. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form VIII) characterized by an X-ray powder diffractogram comprising the following peaks: 8.4, 19.3, and 24.3°2θ±0.2°2θ, as determined on a diffractometer using Cu-Kα radiation at a wavelength of 1.5406 Å.

33. Compound I Form VIII according to claim 32, wherein the diffractogram further comprises peaks at 14.6, 15.0, 16.8, and 20.4°2θ±0.2°2θ.

34. Compound I Form VIII according to claim 32, wherein the diffractogram is substantially as shown in FIG. 44.

35. Compound I Form VIII according to claim 32 characterized by a differential scanning calorimetry (DSC) curve that comprises an endotherm at about 203° C.

36. Compound I Form VIII according to claim 35 characterized by a differential scanning calorimetry (DSC) curve that further comprises a small endotherm at about 75° C.

37. Compound I Form VIII according to claim 32, wherein the DSC curve is substantially as shown in FIG. 45.

38. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide (Compound I Form IX) characterized by an X-ray powder diffractogram comprising the following peaks: 6.9, 14.3, 23.7, and 24.8°2θ±0.2°2θ, as determined on a diffractometer using Cu-Kα radiation at a wavelength of 1.5406 Å.

39. Compound I Form IX according to claim 38, wherein the diffractogram further comprises peaks at 10.1, 21.0, 26.9°2θ±0.2°2θ.

40. Compound I Form IX according to claim 38, wherein the diffractogram is substantially as shown in FIG. 47.

41. Compound I Form IX according to claim 38, characterized by a differential scanning calorimetry (DSC) curve that comprises an endotherm at about 91° C.

42. Compound I Form IX according to claim 38, wherein the DSC curve is substantially as shown in FIG. 48.

43. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide esylate (Compound I Esylate Form I) characterized by an X-ray powder diffractogram comprising the following peaks: 8.9, 23.6, and 25.9 °2θ±0.2°2θ, as determined on a diffractometer using Cu-Kα radiation at a wavelength of 1.5406 Å.

44. Compound I Esylate Form I according to claim 43, wherein the diffractogram further comprises peaks at 16.0 and 24.7°2θ±0.2°2θ.

Figure 19:
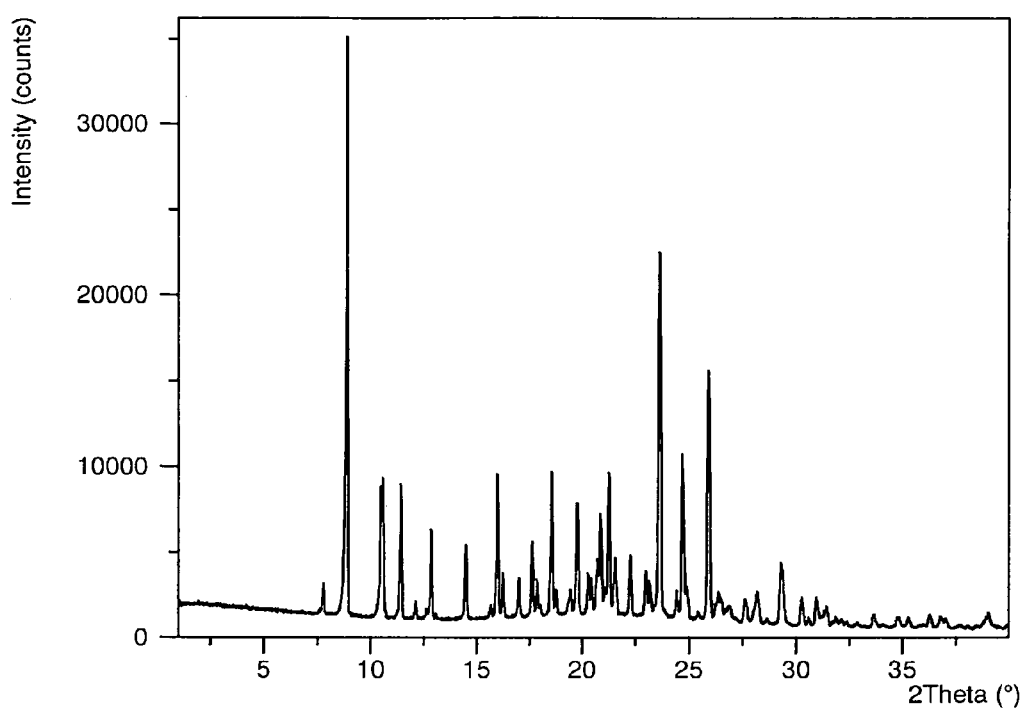
FIG. 19 shows an X-ray powder diffraction (XRPD) of Compound I Esylate Form I.

45. Compound I Esylate Form I according to claim 43, wherein the diffractogram is substantially as shown in FIG. 19.

46. Compound I Esylate Form I according to claim 43, characterized by a differential scanning calorimetry (DSC) curve that comprises an endotherm at about 221° C.

47. Compound I Esylate Form I according to claim 43, wherein the DSC curve is substantially as shown in FIG. 20.

48. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide fumarate (Compound I Fumarate Form I) characterized by an X-ray powder diffractogram comprising the following peaks: 18.9, 23.2, and 25.6°2θ±0.2°2θ, as determined on a diffractometer using Cu-Kα radiation at a wavelength of 1.5406 Å.

49. Compound I Fumarate Form I according to claim 48, wherein the diffractogram further comprises peaks at 7.5 and 26.1°2θ±0.2°2θ.

Figure 22:
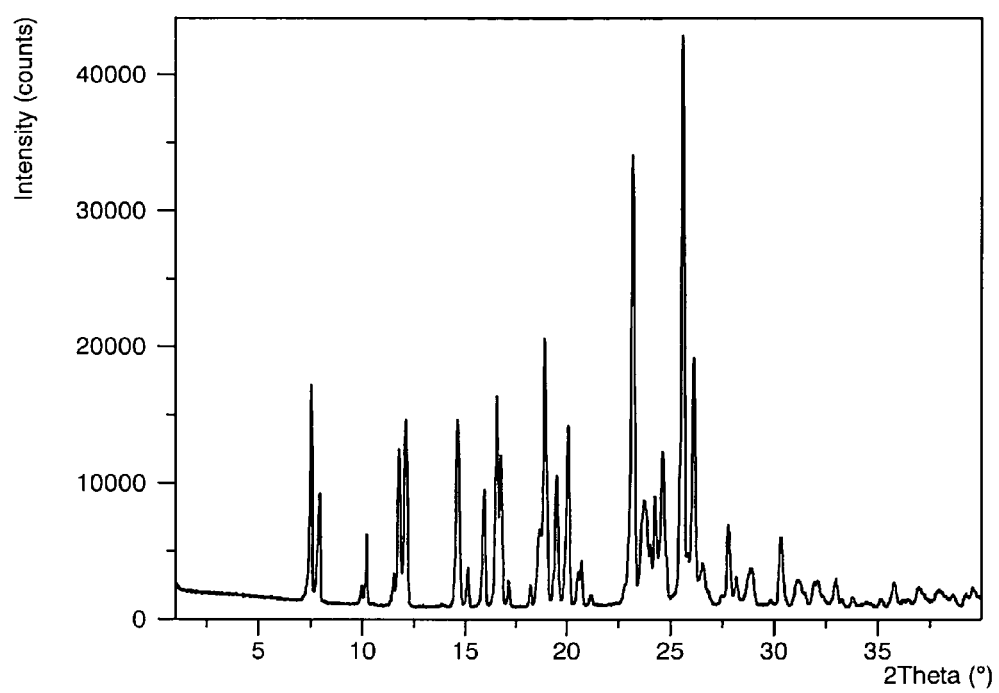
FIG. 22 shows an X-ray powder diffraction (XRPD) of Compound I Fumarate Form I.

50. Compound I Fumarate Form I according to claim 48, wherein the diffractogram is substantially as shown in FIG. 22.

51. Compound I Fumarate Form I according to claim 48, characterized by a differential scanning calorimetry (DSC) curve that comprises an endotherm at about 130° C.

52. Compound I Fumarate Form I according to claim 48, wherein the DSC curve is substantially as shown in FIG. 23.

53. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide glycolate (Compound I Glycolate Form I) characterized by an X-ray powder diffractogram comprising the following peaks: 10.9, 15.1, and 25.2°2θ±0.2°2θ, as determined on a diffractometer using Cu-Kα radiation at a wavelength of 1.5406 Å.

54. Compound I Glycolate Form I according to claim 53, wherein the diffractogram further comprises peaks at 22.2 and 24.6°2θ±0.2°2θ.

Figure 25:
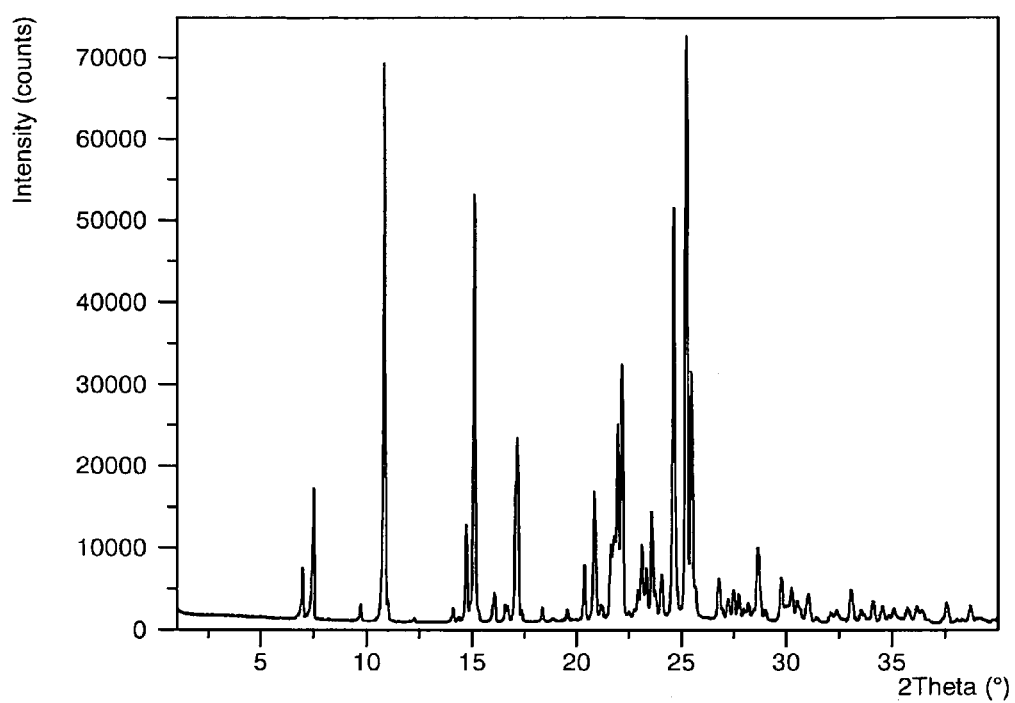
FIG. 25 shows an X-ray powder diffraction (XRPD) of Compound I Glycolate Form I.

55. Compound I Glycolate Form I according to claim 53, wherein the diffractogram is substantially as shown in FIG. 25.

56. Compound I Glycolate Form I according to claim 53, characterized by a differential scanning calorimetry (DSC) curve that comprises an endotherm at about 148° C.

57. Compound I Glycolate Form I according to claim 53, wherein the DSC curve is substantially as shown in FIG. 26.

58. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide hydrochloride (Compound I HCl Form I) characterized by an X-ray powder diffractogram comprising the following peaks: 8.2, 26.0, and 26.1 °2θ±0.2°2θ, as determined on a diffractometer using Cu-Kα radiation at a wavelength of 1.5406 Å.

59. Compound I HCl Form I according to claim 58, wherein the diffractogram further comprises peaks at 12.0 and 19.6°2θ±0.2°2θ.

Figure 28:
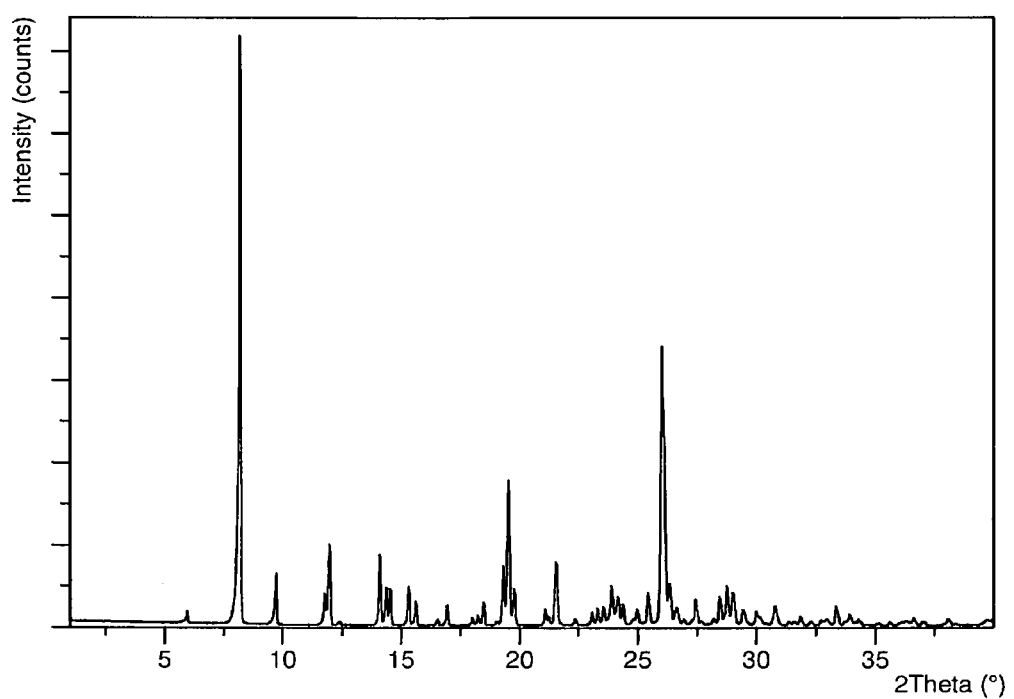
FIG. 28 shows an X-ray powder diffraction (XRPD) of Compound I HCl Form I.

60. Compound I HCl Form I according to claim 58, wherein the diffractogram is substantially as shown in FIG. 28.

61. Compound I HCl Form I according to claim 58, characterized by a differential scanning calorimetry (DSC) curve that comprises an endotherm at about 77° C. and an endotherm at about 191° C.

62. Compound I HCl Form I according to claim 58, wherein the DSC curve is substantially as shown in FIG. 29.

63. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide maleate (Compound I Maleate Form I) characterized by an X-ray powder diffractogram comprising the following peaks: 8.7, 25.7, and 26.5 °2θ±0.2°2θ, as determined on a diffractometer using Cu-Kα radiation at a wavelength of 1.5406Å.

64. Compound I Maleate Form I according to claim 63, wherein the diffractogram further comprises peaks at 17.9 and 26.6°2θ±0.2°2θ.

Figure 31:
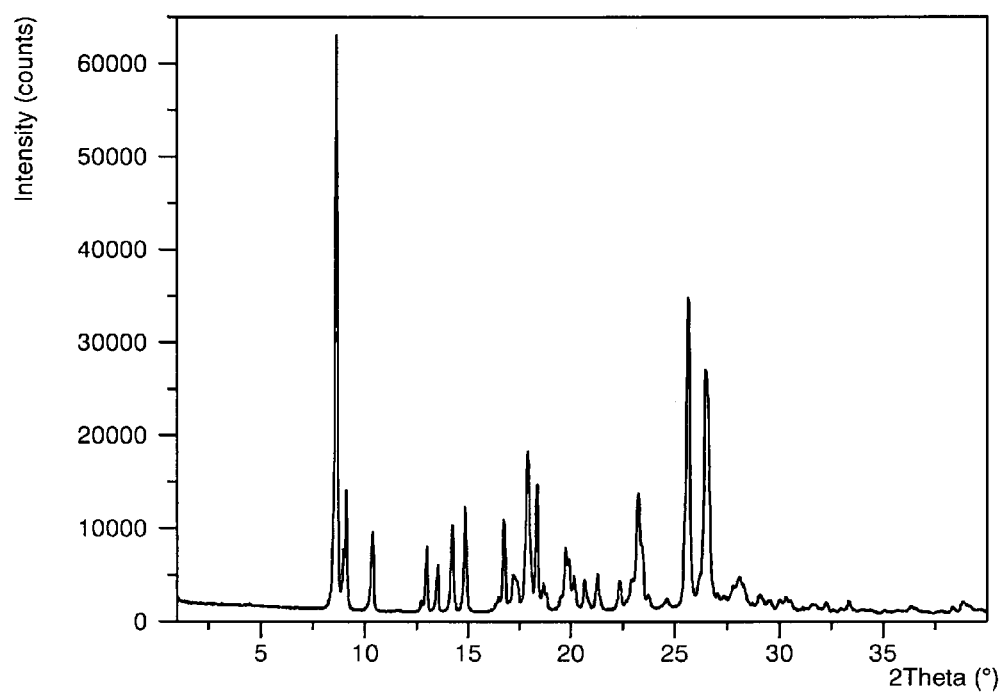
FIG. 31 shows an X-ray powder diffraction (XRPD) of Compound I Maleate Form I.

65. Compound I Maleate Form I according to claim 63, wherein the diffractogram is substantially as shown in FIG. 31.

66. Compound I Maleate Form I according to claim 63, characterized by a differential scanning calorimetry (DSC) curve that comprises an endotherm at about 152° C.

67. Compound I Maleate Form I according to claim 63, wherein the DSC curve is substantially as shown in FIG. 32.

68. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide mesylate (Compound I Mesylate Form I characterized by an X-ray powder diffractogram comprising the following peaks: 8.9, 24.5, and 25.6 °2θ±0.2°2θ, as determined on a diffractometer using Cu-Kα radiation at a wavelength of 1.5406Å.

69. Compound I Mesylate Form I according to claim 68, wherein the diffractogram further comprises peaks at 10.7 and 21.6°2θ±0.2°2θ.

Figure 34:
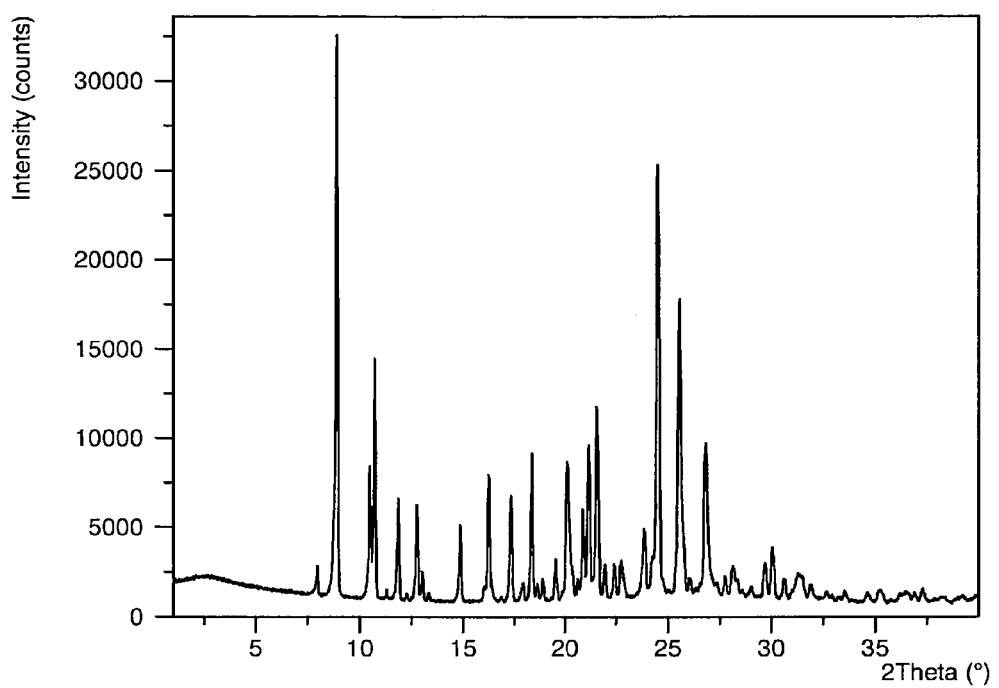
FIG. 34 shows an X-ray powder diffraction (XRPD) of Compound I Mesylate Form I.

70. Compound I Mesylate Form I according to claim 68, wherein the diffractogram is substantially as shown in FIG. 34.

71. Compound I Mesylate Form I according to claim 68, characterized by a differential scanning calorimetry (DSC) curve that comprises an endotherm below 0° C., an endotherm below 100° C., and an endotherm at about 232° C.

72. Compound I Mesylate Form I according to claim 68, wherein the DSC curve is substantially as shown in FIG. 35.

73. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide oxalate (Compound I Oxalate Form I) characterized by an X-ray powder diffractogram comprising the following peaks: 13.3, 13.5, and 26.0°2θ±0.2°2θ, as determined on a diffractometer using Cu-Kα radiation at a wavelength of 1.5406 Å.

74. Compound I Oxalate Form I according to claim 73, wherein the diffractogram further comprises peaks at 7.3 and 24.5°2θ±0.2°2θ.

Figure 37:
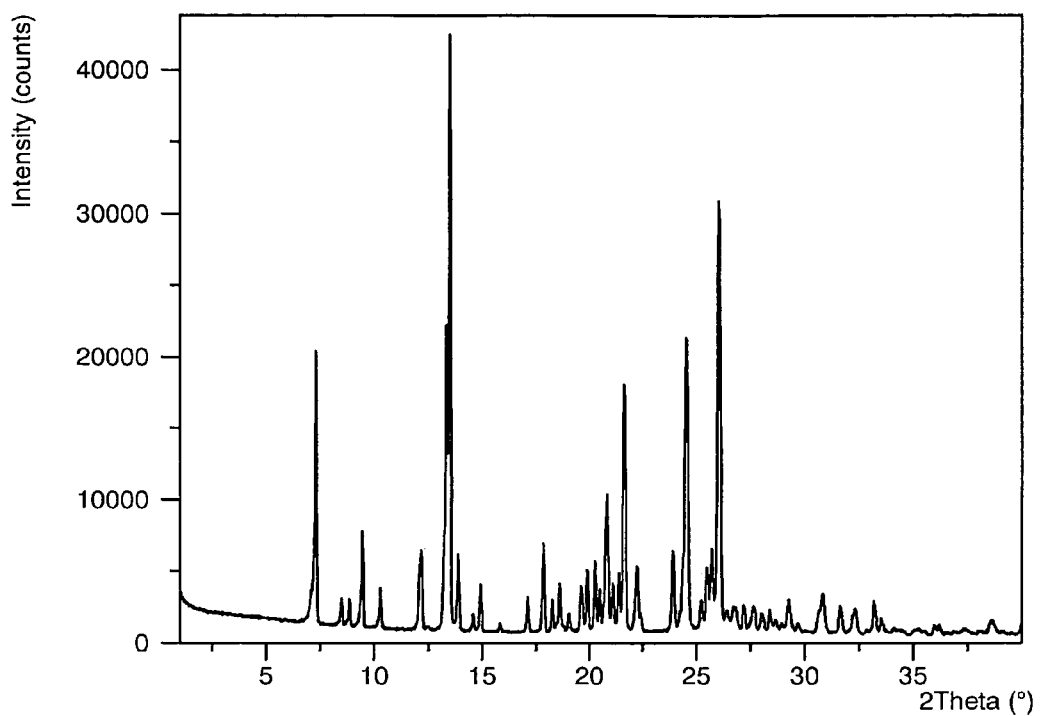
FIG. 37 shows an X-ray powder diffraction (XRPD) of Compound I Oxalate Form I.

75. Compound I Oxalate Form I according to claim 73, wherein the diffractogram is substantially as shown in FIG. 37.

76. Compound I Oxalate Form I according to claim 73, characterized by a differential scanning calorimetry (DSC) curve that comprises an endotherm at about 216° C.

77. Compound I Oxalate Form I according to claim 73, wherein the DSC curve is substantially as shown in FIG. 38.

78. Crystalline 5-(4-cyclopropyl-1H-imidazol-1-yl)-N-(6-(4-isopropyl-4H-1,2,4-triazol-3-yl)pyridin-2-yl)-2-fluoro-4-methylbenzamide sulfate (Compound I Sulfate Form I) characterized by an X-ray powder diffractogram comprising the following peaks: 7.1, 13.8, and 25.5°2θ±0.2°2θ, as determined on a diffractometer using Cu-Kα radiation at a wavelength of 1.5406 Å.

79. Compound I Sulfate Form I according to claim 78, wherein the diffractogram further comprises additional peaks at 17.0 and 21.2°2θ±0.2°2θ.

80. Compound I Sulfate Form I according to claim 78, wherein the diffractogram is substantially shown in FIG. 40.

81. A pharmaceutical composition comprising the form of Compound I of claim 1 and one or more pharmaceutically acceptable carriers.

\* \* \* \* \*

SEQUENCE LISTING

```
<160> NUMBER OF SEQ ID NOS: 2

<210> SEQ ID NO 1
<211> LENGTH: 135
<212> TYPE: PRT
<213> ORGANISM: Mus sp.

<400> SEQUENCE: 1

Met Glu Trp Ser Arg Val Phe Ile Phe Leu Leu Ser Val Thr Ala Gly
1               5                   10                  15

Val His Ser Gln Val Gln Leu Gln Gln Ser Gly Ala Glu Leu Val Arg
            20                  25                  30

Pro Gly Thr Ser Val Lys Val Ser Cys Lys Ala Ser Gly Tyr Ala Phe
        35                  40                  45

Thr Tyr Tyr Leu Ile Glu Trp Val Lys Gln Arg Pro Gly Gln Gly Leu
    50                  55                  60

Glu Trp Ile Gly Val Ile Asn Pro Gly Ser Gly Gly Thr Asn Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Asp Asp Ser Ala Val
            100                 105                 110

Tyr Phe Cys Ala Arg Asn Trp Met Asn Phe Asp Tyr Trp Gly Gln Gly
        115                 120                 125

Thr Thr Leu Thr Val Ser Ser
    130                 135

<210> SEQ ID NO 2
<211> LENGTH: 132
<212> TYPE: PRT
<213> ORGANISM: Mus sp.
```

```
<400> SEQUENCE: 2

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Ser
            20                  25                  30

Val Thr Pro Gly Glu Ser Val Ser Ile Ser Cys Arg Ser Ser Lys Ser
        35                  40                  45

Leu Leu His Ser Asn Gly Asn Thr Tyr Leu Tyr Trp Phe Leu Gln Arg
    50                  55                  60

Pro Gly Gln Ser Pro Gln Phe Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Tyr Thr Phe Gly Gly Gly Thr Lys
        115                 120                 125

Leu Glu Ile Lys
    130
```